US005693650A

United States Patent [19]

Müller et al.

[11] Patent Number: 5,693,650
[45] Date of Patent: Dec. 2, 1997

[54] 4-(QUINOLIN-2-YL-METHOXY)-PHENYL-ACETIC ACID DERIVATIVES

[75] Inventors: Ulrich Müller, Wuppertal, Germany; Richard Connell, Trumbull, Conn.; Siegfried Goldmann; Klaus-Helmut Mohrs, both of Wuppertal, Germany; Rolf Angerbauer, Wuppertal, Germany; Matthias Müller-Gliemann, Solingen, Germany; Ulrich Niewöhner, Wermelskirchen, Germany; Rudi Grützmann, Solingen, Germany; Martin Beuck, Milford, Conn.; Stefan Wohlfeil, Hilden, Germany; Hilmar Bischoff; Dirk Denzer, both of Wuppertal, Germany

[73] Assignee: Bayer Aktiengesellschaft, Leverkusen, Germany

[21] Appl. No.: 567,764

[22] Filed: Dec. 5, 1995

[30] Foreign Application Priority Data

Dec. 9, 1994 [DE] Germany .................. 44 43 892.3

[51] Int. Cl.$^6$ .................... C07D 215/12; A61K 31/47
[52] U.S. Cl. .................... 514/311; 514/307; 546/174; 546/175; 546/139
[58] Field of Search .................... 546/175, 174, 546/139; 514/311, 307

[56] References Cited

U.S. PATENT DOCUMENTS

| | | | |
|---|---|---|---|
| 3,880,919 | 4/1975 | Oediger et al. | 562/444 |
| 3,915,992 | 10/1975 | Baxter-Smallwood et al. | 549/76 |
| 3,976,680 | 8/1976 | Clark et al. | 560/38 |
| 3,988,448 | 10/1976 | Bowman | 514/211 |
| 4,088,815 | 5/1978 | Breuer et al. | 544/26 |
| 4,138,397 | 2/1979 | Bohme | 540/329 |
| 4,216,329 | 8/1980 | Secor | 546/334 |
| 4,474,780 | 10/1984 | Daugherty | 514/209 |
| 4,734,407 | 3/1988 | Schmidt et al. | 514/196 |
| 4,748,163 | 5/1988 | Schmidt et al. | 514/194 |
| 4,929,626 | 5/1990 | Mohrs et al. | 514/311 |
| 4,970,215 | 11/1990 | Mohrs et al. | 514/311 |
| 5,091,392 | 2/1992 | Raddatz et al. | 514/311 |
| 5,126,354 | 6/1992 | Mohrs et al. | 514/311 |
| 5,254,682 | 10/1993 | Dhanoa et al. | 540/451 |
| 5,292,769 | 3/1994 | Mohrs et al. | 514/311 |
| 5,306,820 | 4/1994 | Decker et al. | 546/153 |
| 5,336,805 | 8/1994 | Boesten et al. | 562/444 |
| 5,422,342 | 6/1995 | Henke et al. | 514/18 |
| 5,432,173 | 7/1995 | Husson et al. | 514/230.5 |
| 5,466,699 | 11/1995 | Robertson et al. | 514/323 |

FOREIGN PATENT DOCUMENTS

| | | |
|---|---|---|
| 0344519 | 12/1989 | European Pat. Off. . |
| 0399291 | 11/1990 | European Pat. Off. . |
| 0414076 | 2/1991 | European Pat. Off. . |
| 0499926 | 8/1992 | European Pat. Off. . |
| 0514267 | 11/1992 | European Pat. Off. . |
| 0518672 | 12/1992 | European Pat. Off. . |
| 0529450 | 3/1993 | European Pat. Off. . |
| 0530639 | 3/1993 | European Pat. Off. . |
| 0545170 | 6/1993 | European Pat. Off. . |
| 0545171 | 6/1993 | European Pat. Off. . |
| 0549879 | 7/1993 | European Pat. Off. . |
| 0574774 | 12/1993 | European Pat. Off. . |
| 0582908 | 2/1994 | European Pat. Off. . |
| 0582916 | 2/1994 | European Pat. Off. . |
| 2162717 | 6/1973 | Germany . |
| 2836613 | 3/1980 | Germany . |
| 3900261 | 12/1989 | Germany . |
| 1129029 | 3/1967 | United Kingdom . |
| 1434826 | 5/1976 | United Kingdom . |
| 9118897 | 12/1991 | WIPO . |
| 9410148 | 5/1994 | WIPO . |

OTHER PUBLICATIONS

R. Ross, J. Cell. Biol., vol. 50, pp. 172–186 (1971).
P. Mertes, et al., J. Med. Chem., vol. 12, pp. 342–343, 1969.
R. Williams, J. Org. Chem, vol. 55, pp. 3723–3728, (1990).
G. Schmidt, et al., in "Recent Advances in Chem. therapy", ed. D. Adams, et al., pp 2428–2429, Futruamed Publishers, Munich, Germany, (1992).
M. Hatanaka, et al., J. Med. Chem., vol. 16, No. 9, pp 978–984 (1973).
E. Compere, Jr., et al., Synthesis, pp 852–853 (1977).
J. Knabe, et al., Arch. Pharm., vol. 306, pp. 648–658, (1973).
Y. Oka, et al., Chem. Pharm. Bull., vol 18, No. 3, pp 527–533 (1970).
A. Sonn, et al. Chem. Ber., vol. 66, pp 1900–1903, (1933).
F. Rose–Munch, J. Organomet. Chem., vol. 415, pp 223–255, (1991)
G. Hakimelaki, et al., Can. J. Chem., vol. 57, pp 1932–1938, (1979).
Z. Jedlinski, et al., J. Org. Chem., vol. 52, pp 4601–4602, (1987).
S.J. Daum, et al., Syn. Commun., vol. 11, pp. 1–5, (1981).
H. Boungarten, J. Org. Chem, vol. 31, pp. 3708–3711, (1966).

(List continued on next page.)

Primary Examiner—C. Warren Ivy
Assistant Examiner—D. Margaret M. Mach
Attorney, Agent, or Firm—Sprung Kramer Schaefer & Briscoe

[57] ABSTRACT 4-(Quinolin-2-yl-methoxy)-phenyl-acetic acid derivatives are prepared by reacting quinoline-methoxy-phenyl-acetic acids with the corresponding glycinol derivatives, if appropriate with activation of the carboxylic acid function. The new compounds are suitable as active compounds in medicaments, in particular in antiatherosclerotic medicaments.

10 Claims, No Drawings

OTHER PUBLICATIONS

E. Niemers, et al., Synthesis, pp. 593–595 (1976).
T.P. Sycheva, Chem. Heterocycl. Compounds, pp. 526–531, (1966).
V.M. Aryuzina, et al., Chem. Heterocycl. Compounds, pp 460–464, (1966).
S. Rida, et al., Pharmazie, vol. 41, pp.563–565, (1986).
C. Barney, Tetrahedron Lett., vol. 31, pp. 5547–5550, (1990).
H.V. Secor, J. Org. Chem., vol. 43, No. 12, pp. 2539–2541, (1978).
A.D. Bolat, Khim Farm. Zh., vol. 25, p. 60, (1991).
A.I. Meyers, J. Org. Chem., vol. 43, No. 5, pp 892–898, (1978).
B. Rossiter, et al., Tetrahedron, vol. 49, No. 5, pp. 965–986, (1993).
J. Brittain, et al., Tetrahedron Lett., vol. 34, No. 21, pp. 3363–3366.
G. Bittner, et al., Ann. Chem., vol. 713, pp. 1–11, (1968).
P. Tinapp., Arch. Pharm., vol. 310, pp. 89–94, (1993).
F. Zymalkowski, Arch. Pharm., vol. 291, pp.12–22, (1958).
J. Millen, J. Med. Chem., vol. 28, pp. 12–17, (1985).
D.P. Davis, J. Med. Chem., vol. 24, pp. 12–16, (1981).

4-(QUINOLIN-2-YL-METHOXY)-PHENYL-ACETIC ACID DERIVATIVES

The present invention relates to 4-(quinolin-2-yl-methoxy)-phenyl-acetic acid derivatives, to processes for their preparation and to their use as medicaments, in particular as antiatherosclerotic medicaments.

It is known that increased blood levels of triglycerides (hypertriglyceridaemia) and cholesterol (hypercholesterolaemia) are associated with the origin of atherosclerotic changes to the vascular walls and coronary heart diseases.

There is also a significantly increased risk of the development of coronary heart diseases if these two risk factors occur in combination, which in turn is accompanied by an over-production of apolipoprotein B-100. There is therefore still a great need to provide effective medicaments for combating atherosclerosis and coronary heart diseases.

The compounds 2(R*)- and 2(S*)-2-[4-(quinolin-2-yl-methoxy)phenyl]-2-cyclopentylacetic acid (S)-phenylglycinolamide are known from the publication EP-344 519.

The present invention relates to 4-(quinolin-2-yl-methoxy)-phenyl-acetic acid amides of the general formula (I),

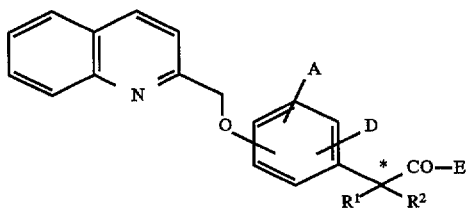

in which

A and D are identical or different and
represent hydrogen, cycloalkyl having 3 to 8 carbon atoms, azido, hydroxyl, halogen, straight-chain or branched alkyl, alkoxy or alkenyl having in each case up to 6 carbon atoms, or a 5- to 6-membered unsaturated or saturated heterocyclic radical having up to 3 heteroatoms from the series consisting of S, N and/or O, $R^1$ represents hydrogen or hydroxyl, or represents straight-chain or branched alkyl having up to 4 carbon atoms, $R^2$ represents hydrogen, hydroxyl, halogen, straight-chain or branched alkenyl or alkoxy having in each case up to 8 carbon atoms or cycloalkyl having 3 to 14 carbon atoms, or
represents straight-chain or branched alkyl having up to 8 carbon atoms, which is optionally substituted by cycloalkyl having 3 to 14 carbon atoms, phenyl or tetrahydropyranyl, which in their turn can be substituted by halogen, or represents the indanyl radical, or $R^1$ and $R^2$ together with the carbon atom form a saturated carbocyclic ring having 5 to 7 carbon atoms, or $R^1$ and $R^2$ together represent a double bond radical of the formula

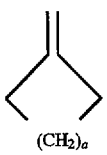

wherein
a denotes the number 2, 3, 4, 5, or 6,
E represents a radical of the formula

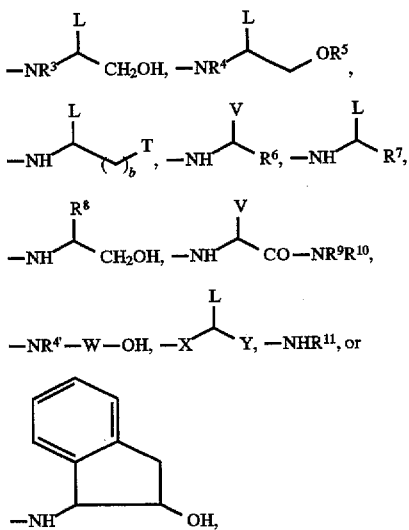

in which
$R^3$ denotes phenyl, methyl or a typical amino-protective group,
$R^4$ and $R^{4'}$ are identical or different and have the above-mentioned meaning of $R^3$ or denote hydrogen,
$R^5$ denotes straight-chain or branched acyl or alkyl having in each case up to 4 carbon atoms,
L denotes phenyl, benzyl or naphthyl, which is optionally substituted up to twice in an identical or different manner by halogen, hydroxyl, pyrrolidinyl, morpholino, amino, trifluoromethyl, trifluoromethoxy, cycloalkyl having 3 to 6 carbon atoms or straight-chain or branched alkyl or alkoxy having in each case up to 6 carbon atoms, which in their turn can be substituted by hydroxyl, or are optionally substituted by phenyl or phenoxy, which in their turn can be substituted up to twice in an identical or different manner by halogen or by straight-chain or branched alkyl having up to 4 carbon atoms, and/or are optionally substituted by a group of the formula $-(O)_c-SO_2R^{12}$,
wherein
c denotes the number 0 or 1 and
$R^{12}$ denotes straight-chain or branched alkyl having up to 4 carbon atoms or phenyl,
b denotes the number 0, 1 or 2.
T denotes a 5- to 7-membered optionally benzo-fused, saturated, partially unsaturated or unsaturated heterocyclic radical having up to 3 heteroatoms from the series consisting of S, N and/or O, wherein both rings are optionally substituted up to three times in an identical or different manner by halogen, hydroxyl, morpholino, amino, cycloalkyl having 3 to 6 carbon atoms, straight-chain or branched alkyl or alkoxy having in each cage up to 6 carbon atoms or phenyl, V has the abovementioned meaning of L or T or denotes a radical of the formula

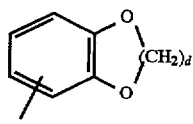

wherein d denotes the number 1, 2 or 3, $R^6$ denotes a radical of the formula $-(CH_2)_e-R^{13}$, wherein e denotes the number 0 or 1, $R^{13}$ denotes hydroxyl, carboxyl or straight-chain or branched alkoxycarbonyl having up to 4 carbon atoms, $R^7$ denotes hydrogen, cyano, trifluoromethyl or straight-chain or branched alkenyl or alkyl having up to 7 carbon atoms, which is optionally substituted up to twice in an identical or different manner by straight-chain or branched alkoxy having up to 4 carbon atoms, or denotes alkoxy having up to 6 carbon atoms, or denotes a group of the formula $-CO-NH-(CH_2)_f-NR^{14}R^{15}$ wherein f denotes the number 1, 2 or 3, $R^{14}$ and $R^{15}$ are identical or different and denote hydrogen, phenyl or straight-chain or branched alkyl having up to 4 carbon atoms, $R^8$ denotes hydrogen, carboxyl, straight-chain or branched alkoxycarbonyl having up to 4 carbon atoms or straight-chain or branched alkyl having up to 5 carbon atoms, which is optionally Substituted by hydroxyl, carboxyl or by straight-chain or branched alkoxycarbonyl having in each case up to 4 carbon atoms or phenyl, $R^9$ and $R^{10}$ are identical or different and denote hydrogen, cycloalkyl having 3 to 6 carbon atoms or phenyl, or denote straight-chain or branched alkyl having up to 6 carbon atoms, which is optionally substituted by phenyl, cycloalkyl having 3 to 6 carbon atoms, hydroxyl, carboxyl, by straight-chain or branched alkoxy or alkoxycarbonyl having in each case up to 4 carbon atoms or by a group of the formula $-NR^{16}R^{17}$ wherein $R^{16}$ and $R^{17}$ are identical or different and denote hydrogen, phenyl or straight-chain or branched alkyl having up to 4 carbon atoms, or $R^9$ and $R^{10}$ together with the nitrogen atom form a heterocyclic radical of the formula

wherein

Z denotes an oxygen atom or the group $-NR^{18}$ or $-CH$, wherein $R^{18}$ denotes hydrogen, acetyl, a typical amino-protective group or a radical of the formula $-SO_2R^{19}$.

wherein $R^{19}$ denotes straight-chain or branched alkyl having up to 4 carbon atoms, benzyl or phenyl, which is optionally substituted by phenyl or tolyl, W denotes straight-chain or branched alkyl having 2 to 7 carbon atoms, which is substituted one to three tunes in an identical or different manner by hydroxyl, pyridyl, norbornyl or phenyl, which in its turn can be substituted by hydroxyl or benzyloxy, or is substituted by a group of the formula $-OR^{20}$ or $-NR^{21}R^{22}$, wherein $R^{20}$ denotes straight-chain or branched alkyl having up to 6 carbon atoms and $R^{21}$ and $R^{22}$ are identical or different and have the abovementioned meaning of $R^{16}$ and $R^{17}$, X denotes an oxygen or sulphur atom, Y denotes formyl or the group $-CHR^{23}R^{24}$, wherein $R^{23}$ denotes hydrogen and $R^{24}$ denotes hydroxyl or straight-chain or branched alkoxy or acyl having in each case up to 4 carbon atoms, or $R^{23}$ and $R^{24}$ are identical or different and denote straight-chain or branched alkoxy having up to 4 carbon atoms, $R^{11}$ denotes a radical of the formula

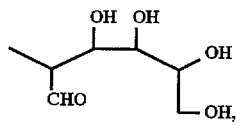

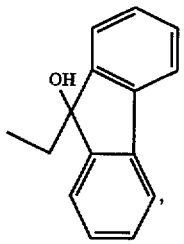

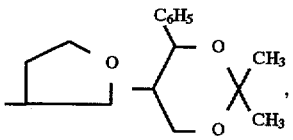

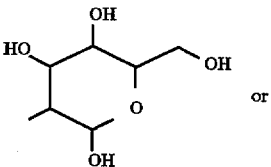

or phenyl which is optionally substituted up to twice in an identical or different manner by halogen, carboxyl or straight-chain or branched alkoxycarbonyl having up to 5 carbon atoms, denotes straight-chain or branched alkyl having up to 6 carbon atoms, which is optionally substituted up to twice in an identical or different manner by hydroxyl, carboxyl, halogen or by straight-chain or branched alkoxycarbonyl having up to 5 carbon atoms, and salts thereof, 2-[4-(quinolin-2-yl-methoxy)phenyl]-2-cyclopentyl-acetic acid metahyloxycarbonylmethylamide, 2-[4-(quinolin-2-yl-methoxy)phenyl]-2-cyclopentyl-acetic acid carboxymethylamide, N-methyl-2-[3-isobutyl-4-(quinolin-2-yl-methoxy)phenyl]-2-cycloheptylacetamide, N-methyl-2-[4-(quinolin-2-yl-methoxy)phenyl]-2-cycloheptyl-acetic acid amide, N-ethyl-2-[4-(quinolin-2-yl-methoxy)phenyl]-2-cyclopentyl-acetic acid amide and N-ethyl-2-[4-(quinolin-2-yl-methoxy)phenyl]-2-cyclohexyl-acetic acid amide being excluded.

The substituted 4-(quinolin-2-yl-methoxy-phenyl)-acetic acid derivatives according to the invention can also be in the form of their salts. Salts with organic or inorganic bases or acids may in general be mentioned here.

Physiologically acceptable salts are preferred in the context of the present invention. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal salts or ammonium salts of the compounds according to the invention which have a free carboxyl group or a tetrazolyl radical. Particularly preferred salts are, for example sodium potassium, magnesium or calcium salts, as well as ammunonium salts, which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

A heterocyclic radical in general is a 5- to 6-membered, saturated, partially unsaturated or unsaturated ring which can contain up to 3 oxygen, sulphur and/or nitrogen atoms as heteroatoms. Preferred rings are 5and 6-membered rings with one oxygen, sulphur and/or up to 2 nitrogen atoms. Rings which are mentioned as preferred are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl, piperazinyl.

A 5- to 6-membered saturated heterocyclic radical which can also contain up to 3 oxygen, sulphur and/or nitrogen atoms as heteroatoms is in general piperidyl, morpholinyl, piperazinyl or pyrrolidyl. Morpholinyl is preferred.

A carbocyclic radical in general is a 3- to 7-membered, preferably 5- to 7-membered, saturated hydrocarbon ring. Cyclopentyl, cyclohexyl or cycloheptyl are mentioned as preferred.

A hydroxy-protective group in the context of the above-mentioned definition is in general a protective group from the series consisting of: tert-butoxydiphenylsilyl, trimethylsilyl, triethylsilyl, triisopropylsilyl, tert-butyl-dimethylsilyl, tert-butyl-diphenylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert-butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxymethyl, 2,4-dimethoxybenzyloxycarbonyl, methylthiomethyl, methoxyethoxymethyl, [2-(trimethylsilyl)ethoxy]methyl, 2-(methylthiomethoxy) ethoxycarbonyl, benzoyl, 4-methylbenzoyl, 4-nitrobenzoyl, 4-fluorobenzoyl, 4-chlorobenzoyl or 4-methoxybenzoyl. Acetyl, benzoyl, benzoyl, or methylbenzyl are preferred.

Amino-protective groups in the context of the invention are the customary amino-protective groups used in peptide chemistry.

These include, preferably: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxylbenzyloxycarbonyl, cyclohexoxycarbonyl, 1,1-dimethylethoxycarbonyl, adamantylcarbonyl, phthaloyl, 2,2,2-trichloroethoxycarbonyl, 2,,2,2-trichloro-tert-butoxycarbonyl, methyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

The compounds according to the invention can exist in stereoisomeric forms which either behave as mirror images (enantiomers) or do not behave as mirror images (diastereomers). The invention relates to both the enantiomers or diastereomers or the particular mixtures thereof. These mixtures of the enantiomers and diastereomers can be separated into the stereoisomerically uniform constituents in a known manner.

Diastereomers can be represented, for example, by the following formulae:

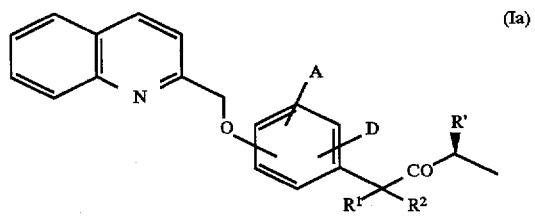

(Ia)

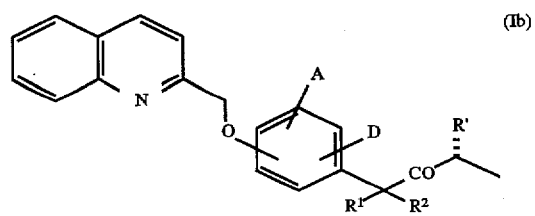

(Ib)

Preferred compounds of the general formula (I) are those in which

A and D are identical or different and represent hydrogen, cyclopropyl, cyclopentyl, cyclohexyl, azido, hydroxyl, fluorine, chlorine, bromine, straight-chain or branched alkyl, alkoxy or alkenyl having in each case up to 5 carbon atoms, pyrryl or imidazolyl, $R^1$ represents hydrogen or hydroxyl or represents straight-chain or branched alkyl having up to 3 carbon atoms, $R^2$ represents hydrogen, hydroxyl, fluorine, chlorine, bromine, straight-chain or branched alkenyl or alkoxy having in each case up to 7 carbon atoms, cyclopentyl, cyclohexyl, cycloheptyl, cyclooctyl, cyclononyl, cyclodecyl, cycloundecyl or cyclododecyl, or represents straight-chain or branched alkyl having up to 7 carbon atoms, which is optionally substituted by cyclopentyl, cyclohexyl, cycloheptyl, cyclooctyl, cyclononyl, cyclodecyl, cycloundecyl or cycloclodecyl, phenyl or tetrahydropyranyl, which in their turn can be substituted by fluorine, chlorine or bromine, or represents the indanyl radical, or $R^1$ and $R^2$ together with the carbon atom form a cyclopentyl, cyclohexyl or cycloheptyl ring, or $R^1$ and R2 together represent a double bond radical of the formula

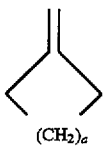

(CH$_2$)$_a$ wherein a denotes the number 2, 3, 4 or 5,

E represents a radical of the formula

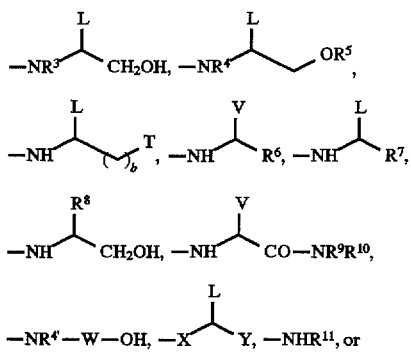

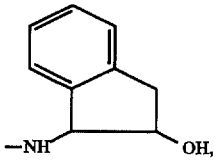

in which $R^3$ denotes phenyl, methyl, acetyl or tert-butoxycarbonyl (Boc), $R^4$ and $R^{4'}$ are identical or different and have the above-mentioned meaning of $R^3$ or denote hydrogen.

$R^5$ denotes straight-chain or branched acyl or alkyl having in each case up to 3 carbon atoms, L denotes phenyl, benzyl or naphthyl, which are optionally substituted up to twice in an identical or different manner by fluorine, chlorine, bromine, iodine, hydroxyl, pyrrolidinyl, morpholino, amino, trifluoromethyl, trifluoromethoxy, cyclopropyl, cyclopentyl, cyclohexyl or straight-chain or branched alkyl or alkoxy having in each case up to 6 carbon atoms, which in their turn can be substituted by hydroxyl or are optionally substituted by phenyl or phenoxy, which in their turn can be substituted up to twice in an identical or different manner by fluorine, chlorine, bromine or by straight-chain or branched alkyl having up to 3 carbon atoms, and/or are optionally substituted by a group of the formula —(O)$_c$SO$_2$—$R^{12}$, wherein c denotes the number 0 or 1, and $R^{12}$ denotes straight-chain or branched alkyl having up to 4 carbon atoms or phenyl, b denotes the number 0 or 1, T denotes a heterocyclic radical of the formula

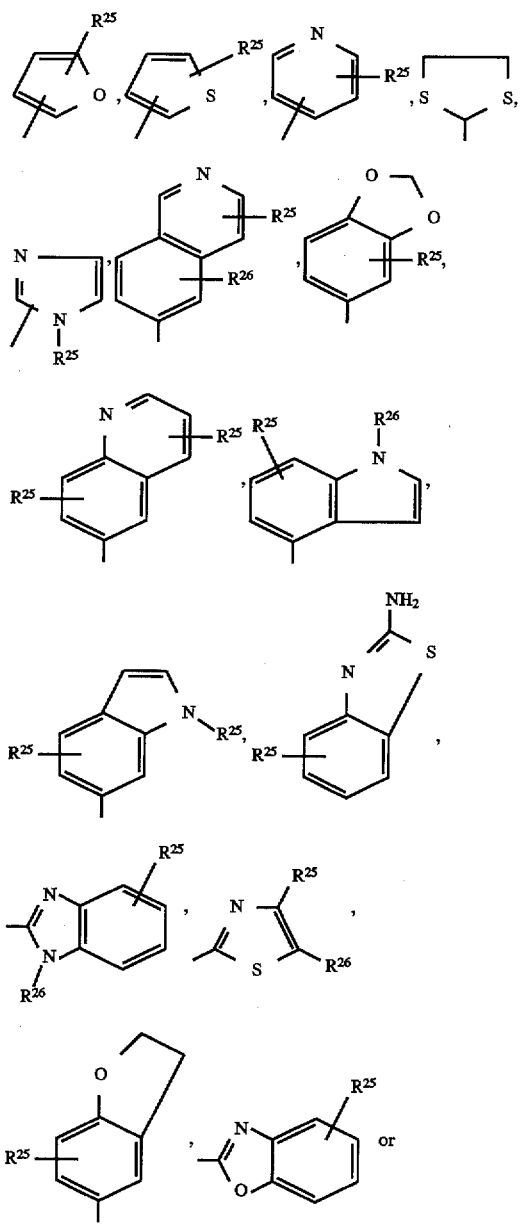

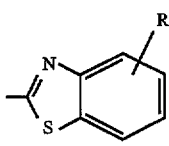

wherein
R$^{25}$ and R$^{26}$ are identical or different and denote hydrogen, straight-chain or branched alkyl having up to 4 carbon atoms or amino, V has the abovementioned meaning of L or T or denotes a radical of the formula

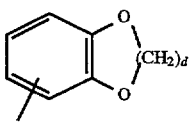

wherein
d denotes the number 1 or 2,
R$^6$ denotes a radical of the formula —(CH$_2$)$_e$—R$^{13}$,
wherein
e denotes the number 0 or 1,
R$^{13}$ denotes hydroxyl, carboxyl or straight-chain or branched alkoxycarbonyl having up to 3 carbon atoms,
R$^7$ denotes hydrogen, cyano, trifluoromethyl, vinyl or straight-chain or branched alkyl having up to 6 carbon atoms, which is optionally substituted up to twice in an identical or different manner by straight-chain or branched alkoxy having up to 3 carbon atoms, or denotes alkoxy having up to 5 carbon atoms, or denotes a group of the formula —CO—NH—(CH$_2$)$_f$—NR$^{14}$R$^{15}$
wherein
f denotes the number 1, 2 or 3,
R$^{14}$ and R$^{15}$ are identical or different and denote hydrogen, phenyl or straight-chain or branched alkyl having up to 3 carbon atoms,
R$^8$ denotes hydrogen, carboxyl, straight-chain or branched alkoxycarbonyl having up to 3 carbon atoms or straight-chain or branched alkyl having up to 5 carbon atoms, which is optionally substituted by hydroxyl, carboxyl or by straight-chain or branched alkoxycarbonyl having in each case up to 3 carbon atoms or phenyl,
R$^9$ and R$^{10}$ are identical or different and
denote hydrogen, cyclopropyl, cyclopentyl cyclohexyl or phenyl, or denote straight-chain or branched alkyl having up to 5 carbon atoms, which is optionally substituted by phenyl, cyclopropyl, cyclopentyl, cyclohexyl, hydroxyl, carboxyl, by straight-chain or branched alkoxy or alkoxycarbonyl having in each case up to 3 carbon atoms or by a group of the formula —NR$^{16}$R$^{17}$,
wherein
R$^{16}$ and R$^{17}$ identical or different and denote hydrogen, phenyl or straight-chain or branched alkyl having up to 3 carbon atoms, or
R$^9$ and R$^{10}$ together with the nitrogen atom form a heterocyclic radical of the formula

wherein
Z denotes an oxygen atom or the group —NR$^{18}$ or —CH,
wherein
R$^{18}$ denotes hydrogen, acetyl, tert-butoxycarbonyl or a radical of the formula —SO$_2$R$^{19}$,
wherein
R$^{19}$ denotes straight-chain or branched alkyl having up to 3 carbon atoms, benzyl or phenyl, which is optionally substituted by phenyl or tolyl,
W denotes straight-chain or branch alkyl having 2 to 7 carbon atoms, which is substituted 1 to 3 times in an identical or different manner by _ hydroxyl, pyridyl, norbornyl or phenyl, which in its turn can be substituted by hydroxyl or benzyloxy, or is substituted by a group of the formula —OR$^{20}$ or —NR$^{21}$R$^{22}$,
wherein
R$^{20}$ denotes straight-chain or branched alkyl having up to 5 carbon atoms and
R$^{21}$ and R$^{22}$ are identical or different and have the abovementioned meaning of R$^{16}$ and R$^{17}$,
X denotes an oxygen or sulphur atom,
Y denotes formyl or the group —CHR$^{23}$R$^{24}$,
wherein
R$^{23}$ denotes hydrogen,
R$^{24}$ denotes hydroxyl or straight-chain or branched alkoxy or acyl having in each case up to 3 carbon atoms,
or
R$^{23}$ and R$^{24}$ are identical or different and denote straight-chain or branched alkoxy having up to 3 carbon atoms,
R$^{11}$ denotes a radical of the formula

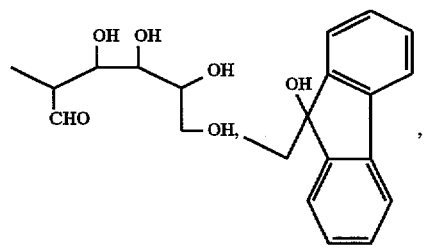

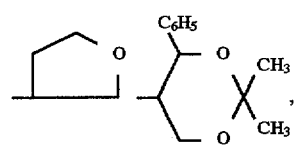

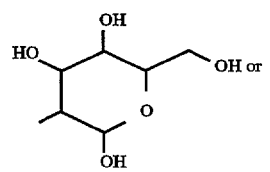

phenyl, which is optionally substituted up to twice in an identical or different manner by fluorine, chlorine, bromine, carboxyl or straight-chain or branched alkoxycarbonyl having up to 4 carbon atoms, or denotes straight-chain or branched alkyl having up to 5 carbon atoms, which is optionally substituted up to twice in an identical or different manner by hydroxyl, carboxyl, fluorine, chlorine, bromine or by straight-chain or branched alkoxycarbonyl having up to 4 carbon atoms, and salts thereof, 2-[4-(quinolin-2-yl-methoxy)phenyl]-2-cyclopentyl-acetic acid methyloxycarbonyl-methylamide, 2-[4-(quinolin-2-yl-methoxy)phenyl]-2-cyclopentyl-acetic acid carboxymethylamide, N-methyl-2-[3-isobutyl-4-(quinolin-2-yl-methoxy)phenyl]-2-cycloheptylacetamide, N-methyl-2-[4-(quinolin-2-yl-methoxy)phenyl]-2-cycloheptyl-acetic acid amide, N-ethyl-2-[4-(quinolin-2-yl-methoxy)phenyl]-2-cyclopentyl-acetic acid amide and N-ethyl-2-[4-(quinolin-2-yl-methoxy)phenyl]-2-cyclohexyl-acetic acid amide being excluded.

Particularly preferred compounds of the general formula (I) are those in which

A and D are identical or different and
represent hydrogen, cyclopropyl, cyclopentyl, cyclohexyl, azido, hydroxyl, fluorine, chlorine, bromine, straight-chain or branched alkyl, alkoxy or alkenyl having in each case up to 4 carbon atoms, imidazolyl or pyrryl, $R^1$ represents hydrogen, hydroxyl or straight-chain or branched alkyl having up to 3 carbon atoms, $R^2$ represents hydrogen, hydroxyl, fluorine, chlorine, straight-chain or branched alkenyl or alkoxy having in each case up to 5 carbon atoms, cyclopentyl, cyclohexyl, cycloheptyl, cyclooctyl, cyclononyl, cyclodecyl or cycloundecyl or represents straight-chain or branched alkyl having up to 6 carbon atoms, which is optionally substituted by cyclopentyl, cyclohexyl, cycloheptyl, cyclooctyl, cyclononyl, cycloundecyl, phenyl or tetrahydropyranyl, which in their turn can be substituted by fluorine, chlorine or bromine, or represents the indanyl radical, $R^1$ and $R^2$ together with the carbon atom form a cyclopentyl, cyclohexyl or cycloheptyl ring, E represents a radical of the formula

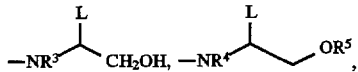

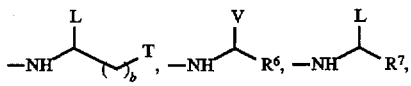

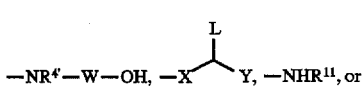

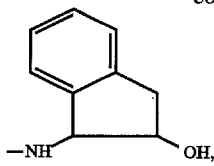

in which $R^3$ denotes phenyl, methyl, acetyl or tert-butoxycarbonyl (Boc), $R^4$ and $R^{4'}$ are identical or different and have the above-mentioned meaning of $R^3$ or denote hydrogen, $R^5$ denotes straight-chain or branched acyl or alkyl having in each case up to 3 carbon atoms, L denotes phenyl, benzyl or naphthyl, which are optionally substituted up to twice in an identical or different manner by fluorine, chlorine, bromine, iodine, hydroxyl, pyrrolidinyl, morpholino, trifluoromethoxy, trifluoromethyl, amino, cyclopropyl, cyclopentyl, cyclohexyl or straight-chain or branched alkyl or alkoxy having in each case up to 6 carbon atoms, which in their turn can be substituted by hydroxyl, or are optionally substituted by phenyl or phenoxy, which in their turn can be substituted up to twice in an identical or different manner by fluorine, chlorine or by straight-chain or branched alkyl having up to 3 carbon atoms, and/or are optionally substituted by a group of the formula $—(O)_cSO_2—R^{12}$, wherein c denotes the number 0 or 1, and $R^{12}$ denotes straight-chain or branched alkyl having up to 3 carbon atoms or phenyl, b denotes the number 0 or 1, T denotes a heterocyclic radical of the formula

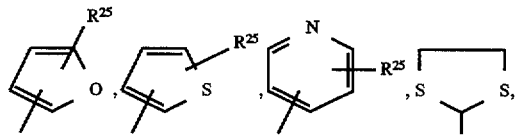

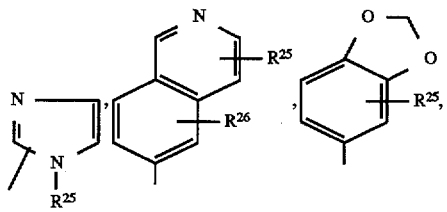

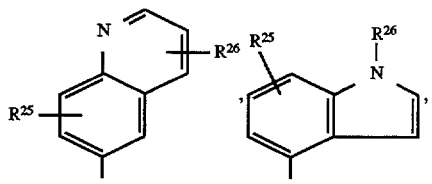

-continued

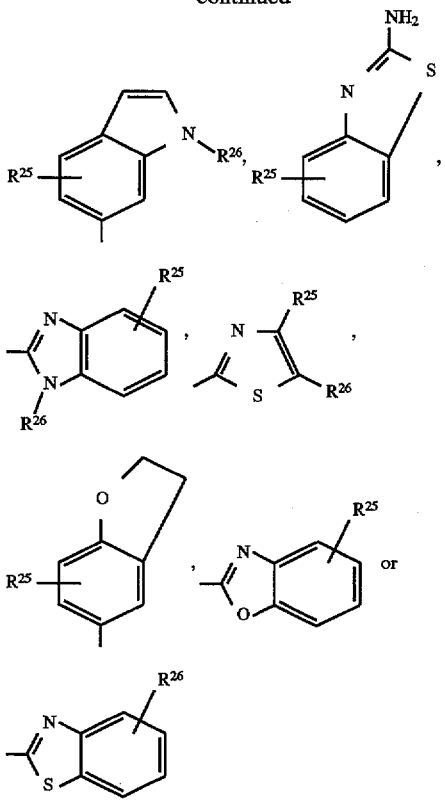

wherein
R²⁵ and R²⁶ are identical or different and denote hydrogen, straight-chain or branched alkyl having up to 4 carbon atoms or amino,
V has the abovementioned meaning of L or T or denotes a radical of the formula

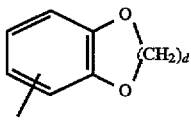

wherein
d denotes the number 1 or 2,
R⁶ denotes a radical of the formula —(CH₂)ₑ—R¹³,
wherein
e denotes the number 0 or 1,
R¹³ denotes hydroxyl, carboxyl or straight-chain or branched alkoxycarbonyl having up to 3 carbon atoms,
wherein
R⁷ denotes hydrogen, cyano, trifluoromethyl, vinyl or straight-chain or branched alkyl having up to 5 carbon atoms, which is optionally substituted up to twice in an identical or different manner by straight-chain or branched alkoxy having up to 3 carbon atoms, or denotes alkoxy having up to 3 carbon atoms, or denotes a group of the formula —CO—NH—(CH₂)_f—NR¹⁴R¹⁵,
wherein
f denotes the number 1, 2 or 3,
R¹⁴ and R¹⁵ are identical or different and denote hydrogen, phenyl or straight-chain or branched alkyl having up to 3 carbon atom R⁸ denotes hydrogen, carboxyl, straight-chain or branched alkoxycarbonyl having up to 3 carbon atoms or straight-chain or branched alkyl having up to 4 carbon atoms, which is optionally substituted by hydroxyl, carboxyl or by straight-chain or branched alkoxycarbonyl having in each case up to 3 carbon atoms or phenyl, R⁹ and R¹⁰ are identical or different and
denote hydrogen, cyclopropyl, cyclopentyl, cyclohexyl or phenyl, or denote straight-chain or branched alkyl having up to 5 carbon atoms, which is optionally substituted by phenyl, cyclopropyl, cyclopentyl cyclohexyl, hydroxyl, carboxyl, by straight-chain or branched alkoxy or alkoxycarbonyl having in each case up to 3 carbon atoms or by a group of the formula —NR¹⁶R¹⁷,
wherein
R¹⁶ and R¹⁷ are identical or different and denote hydrogen, phenyl or straight-chain or branched alkyl having up to 3 carbon atoms, or R⁹ and R¹⁰ together with the nitrogen atom form a heterocyclic radical of the formula

wherein
Z denotes an oxygen atom or the group —NR¹⁸ or —CH,
wherein
R¹⁸ denotes hydrogen, acetyl, tert-butoxycarbonyl or a radical of the formula —SO₂R¹⁹,
w.herein
R¹⁹ denotes straight-chain or branched alkyl having up to 3 carbon atoms, benzyl or phenyl, which is optionally substituted by phenyl or tolyl, W denotes straight-chain or branched alkyl having 2 to 7 carbon atoms, which is substituted 1 to 3 times in an identical or different manner by hydroxyl, pyridyl, norbornyl or phenyl, which in its turn can be substituted by hydroxyl or benzyloxy, or is substituted by a group of the formula —OR²⁰ or —NR²¹R²²,
wherein
R²⁰ denotes straight-chain or branched alkyl having up to 4 carbon atoms and
R²¹ and R²² are identical or different and have the abovementioned meaning of R¹⁶ and R¹⁷,
X denotes an oxygen or sulphur atom,
Y denotes formyl or the group —CHR²³R²⁴,
wherein
R²³ denotes hydrogen,
R²⁴ denotes hydroxyl or straight-chain or branched alkoxy or acyl having in each case up to 3 carbon atoms,
or
R²³ and R²⁴ are identical or different and denote straight-chain or branched alkoxy having up to 3 carbon atoms, $R^{11}$ denotes a radical of the formula

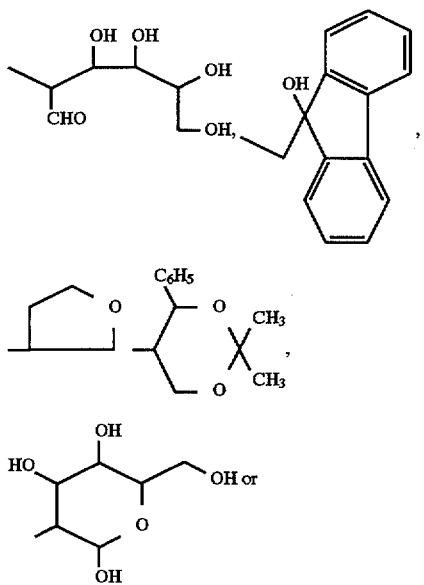

phenyl, which is optionally substituted up to twice in an identical or different manner by fluorine, chlorine, bromine, carboxyl or straight-chain or branched alkoxycarbonyl having up to 3 carbon atoms, or denotes straight-chain or branched alkyl having up to 5 carbon atoms, which is optionally substituted up to twice in an identical or different manner by hydroxyl, carboxyl, fluorine, chlorine, bromine or by straight-chain or branched alkoxycarbonyl having up to 3 carbon atoms.

and salts thereof,

2-[4-(quinolin-2-yl-methoxy)phenyl]-2-cyclopentyl-acetic acid methyloxycarbonylmethylamide, 2-[4(quinolin-2-yl-methoxy)phenyl]-2-cyclopentyl-acetic acid carboxymethylamide, N-methyl-2-[3-isobutyl-4-(quinolin-2-yl-methoxy)phenyl]-2-cycloheptylacetamide, N-methyl-2-[4-(quinolin-2-yl-methoxy)phenyl]-2-cycloheptyl-acetic acid amide, N-ethyl-2-[4-(quinolin-2-yl-methoxy)phenyl]-2-cyclopentyl-acetic acid amide and N-ethyl-2-[4-(quinolin-2-yl-methoxy)phenyl]-2-cyclohexyl-acetic acid amide being excluded.

Processes have also been found for the preparation of the compounds of the general formula (I) according to the invention, characterized in that

[A] in the case where E does not represent the radical of the formula

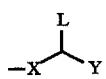

carboxylic acids of the general formula (II)

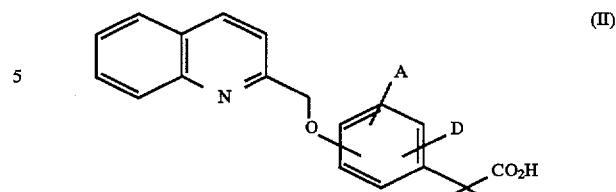

in which

A, D, $R^1$ and $R^2$ have the meaning given, if appropriate with prior activation of the carboxylic acid function, are reacted with glycinols or esters thereof of the general formula (III)

in which $R^{27}$ has the abovementioned scope of meaning of L, V, W and $R^8$ and $R^{28}$ represents —$CH_2$—OH or represents ($C_1$–$C_8$)-alkoxycarbonyl in inert solvents, in the presence of a base and if appropriate of an auxiliary, and

[B] in the case where E represents the radical of the group

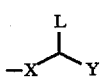

the carboxylic acids of the general formula (II), after prior activation of the carboxylic acid function, are reacted with compounds of the general formula (IV)

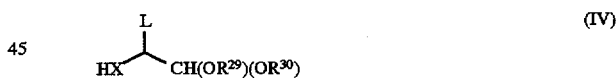

in which

X and L have the abovementioned meaning and $R^{29}$ and $R^{30}$ are identical or different and denote $C_1$–$C_6$-alkyl, in inert solvents, if appropriate in the presence of a base and/or auxiliary, and in the case where Y=CHO, oxidation follows, and, depending on the particular definition of the abovementioned substituent E, if appropriate an acylation, reduction, hydrolysis, amidation, alkylation, sulphoamidation and/or elimination is carried out by customary methods.

The process according to the invention can be illustrated by way of example by the following equation:

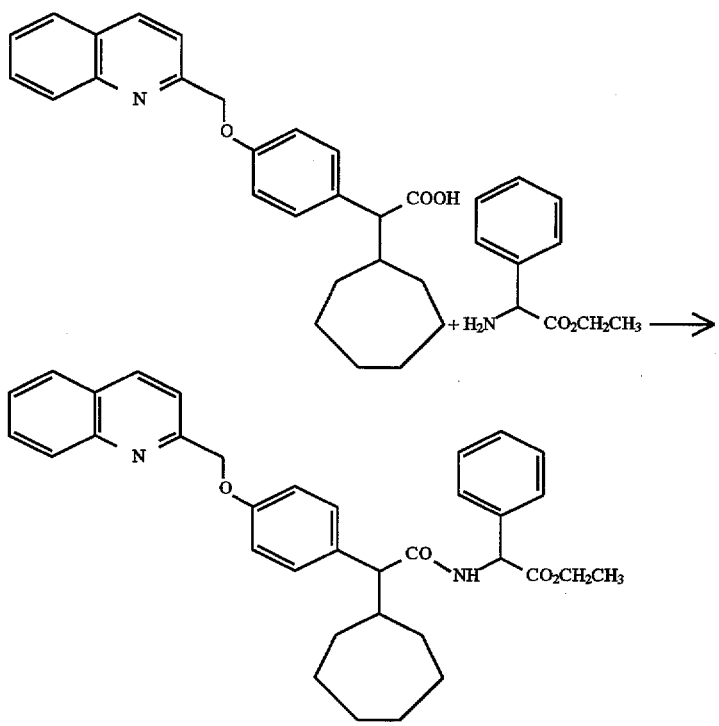

Suitable solvents here are inert organic solvents which do not change under the reaction conditions. These include ethers, such as diethyl ether or tetrahydrofuran, halogenated hydrocarbons, such as methylene chloride, chloroform, carbon tetrachloride, 1,2-dichloroethane, trichloroethane, tetachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Methylene chloride, tetrahydrofuran, acetone or dimethylformamide are particularly preferred.

Suitable bases are the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholates such as, for example, sodium ethanolate or potassium ethanolate or sodium methanolate or potassium methanolate, or organic amines, such as triethylamine, picoline or N-methylpiperidine, or amides, such as sodium amide or lithium diisopropylamide, or organometallic compounds, such as butyllithium or phenyllithium. Sodium carbonate and potassium carbonate and triethylamine are preferred.

The base is employed in an amount of 0.6 mol to 5 mol, preferably 0.7 mol to 2 mol, per mole of the compound of the general formula (II).

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Compounds which are suitable for activation of the carboxylic acid function are in general bases and/or dehydrating reagents, such as, for example, diisopropylcarbodiimide, dicyclohexylcarbodiimide or N-(3-dimethylammopropyl)- N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphoric acid anhydride or isobutyl chloroformate or benzotriazolyloxy-tris-(dimethylamino)phosphonium hexafluorophosphate or phosphonic acid diphenyl ester amide or methanesulphonyl chloride, if appropriate in the presence of bases, such as triethylamine or N-ethylmorpholine or N-methylpiperidine or dicyclohexylcarbodiimide and N-hydroxysuccinimide.

The acid-binding agents and dehydrating reagents are in general employed in an amount of 0.5 to 3 mol, preferably 1 to 1.5 mol, per mole of the corresponding carboxylic acids.

The carboxylic acid function is in general activated in a temperature range from 0° C. to 150° C., preferably from 0° C. to 80° C., end if appropriate under an inert gas atmosphere.

The alkylation is in general carried out with alkylating agents, such as, for example, $(C_1-C_8)$-alkyl halides, sulphonic acid esters or substituted or unsubstituted $(C_1-C_8)$-dialkyl- or $(C_1-C_8)$-diarylsulphonates, preferably methyl iodide or dimethyl sulphate.

The alkylation is in general carried out in one of the abovementioned solvents, preferably in dimethylformamide, in a temperature range from 0° C. to +70° C., preferably from 0° C. to +30° C., under normal pressure.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate, or alkali metal alcoholates, such as sodium methanolate, sodium ethanolate, potassium methanolate, potassium ethanolate or potassium tert-butanolate. Sodium hydroxide or potassium hydroxide are particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide, or dimethyl sulphoxide. Alcohols, such as methanol, ethanol, propanol or isopropanol, are particularly preferably used. It is also possible to employ mixtures of the solvents mentioned.

If appropriate, the hydrolysis can also be carried out with acids, such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or finder increased pressure (for example from 0.5 to 5 bar).

In carrying out the hydrolysis, the base is in general employed in an amount of 1 to 3 mol, preferably 1 to 1.5 mol, per mole of the ester. Molar amounts of the reactants are particularly preferably used.

The hydrolysis of tert-butyl esters is in general carried out with acids, such as, for example, hydrochloric acid or trifluoroacetic acid, in the presence of one of the abovementioned solvents and/or water or mixtures thereof, preferably with dioxane or tetrahydrofuran.

The oxidation in the case where Y=CHO is in general carried out in one of the abovementioned ethers, preferably dioxane, and in the presence of an acid. Acids include, preferably, inorganic acids, such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids with $C_1$–$C_4$-alkyl radicals or aryl radicals, such as, for example, methanesulphonic acid, ethanesulphonic acid, benzenesulphonic acid or toluenesulphonic acid. Hydrochloric acid is preferred.

The oxidation is in general carried out in a temperature range from 0° C. to +100° C., preferably from +20° C. to +80° C.

The oxidation is in general carried out under normal pressure. However, it is also possible to carry out the oxidation under reduced pressure or under increased pressure (for example from 0.5 to 5 bar).

The amidation and the sulphonamidation are in general carried out in one of the abovementioned solvents, preferably in tetrahydrofuran or methylene chloride.

If appropriate, the amidation and the sulphonamidation can proceed via the activated state of the acid halides, which can be prepared from the corresponding acids by reaction with thionyl chloride, phosphorus trichloride, phosphorus pentachloride, phosphorus tribromide or oxalyl chloride.

The amidation and the sulphonamidation are in general carried out in a temperature range from −20° C. to +80° C., preferably from −10° C. to +30° C., under normal pressure.

Suitable bases for this are, in addition to the abovementioned bases, preferably triethylamine and/or dimethylaminopyridine, DBU or DABCO.

The base is employed in an amount of 0.5 mol to 10 mol, preferably 1 mol to 2 mol, per mole of the corresponding acid or ester.

Acid-binding agents which can be employed for the sulphonamidation are alkali metal or alkaline earth metal carbonates, such as sodium carbonate or potassium carbonate, alkali metal or alkaline earth metal hydroxides, such as, for example, sodium hydroxide or potassium hydroxide, or organic bases, such as pyridine, triethylamine, N-methylpiperidine or bicyclic amidines, such as 1,5-diazabicyclo[3.4.0]-non-5-ene (DBN) or 1,5-diazabicyclo[3.4.0]-undec-5-ene (DBU). Potassium carbonate is preferred.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride or carbonyl compounds, such as carbonyldiimidazole, or 1,2-oxazolium compounds, such as 2-ethyl-5-phenyl-1,2-oxazolium-3-sulphonate or propanephosphoric acid anhydride or isobutylchloroformate or benzotriazolyloxy-tris-(dimethylamino)phosphonium hexafluorophosphate or phosphonic acid diphenyl esteramide or methanesulphonyl chloride, if appropriate in the presence of bases, such as triethylamine or N-ethylmorpholine or N-methylpiperidine or dicyclohexylcarbodiimide or N-hydroxysuccinimide.

The acid-binding agents and dehydrating reagents are in general employed in an amount of 0.5 to 3 mol, preferably 1 to 1.5 mol, per mole of the corresponding carboxylic acids.

Suitable solvents here are all the inert solvents which do not change under the reaction conditions. These include, preferably, alcohols, such as methanol, ethanol, propanol or isopropanol, or ethers, such as diethylene glycol dimethyl ether, or amides, such as hexamethylphosphoric acid triamide or dimethylformamide, or acetic acid. It is also possible to use mixtures of the solvents mentioned.

The reductions can in general be carried out by hydrogen in water or in inert organic solvents, such as alcohols, ethers or halogenated hydrocarbons, or mixtures thereof, with catalysts, such as Raney nickel, palladium, palladium-on-animal charcoal or platinum, or with hydrides or boranes in inert solvents, if appropriate in the presence of a catalyst.

The reaction is preferably carried out with hydrides, such as complex borohydrides or aluminium hydrides. Sodium borohydride, lithium aluminium hydride or sodium cyanoborohydride are particularly preferably employed here.

The reaction is in general carried out in a temperature range from 0° C. to 150° C., preferably from +20° C. to +110° C.

The reaction can be carried out under normal, increased or reduced pressure (for example 0.5 to 5 bar). The reaction is in general carried out under normal pressure.

The acylation is in general carried out in one of the abovementioned solvents, preferably methylene chloride, and in the presence of a typical acylating agent such as, for example, acetyl chloride.

The acylation is in general carried out in a temperature range from 0° C. to 150° C., preferably from +20° C. to +110° C.

The acylation can be carried out under normal, increased or reduced pressure (for example 0.5 to 5 bar). It is in general carried out under normal pressure.

The elimination is in general carried out in one of the abovementioned solvents, in the presence of a base and an auxiliary. Diethylformamide, methyl chloride and triethylamine are preferred.

The elimination is in general carried out in a temperature range from 0° C. to 150° C., preferably from +20° C. to +110° C.

The elimination can be carried out under normal, increased or reduced pressure (for example 0.5 to 5 bar). The elimination is in general carried out under normal pressure.

The compounds of the general formula (II) are known (cf. U.S. Pat. Nos. 4,929,629, 4,970,215, 5,091,392, 5,126,354, EP 414 078, 529 450) or they can be prepared by a process in which compounds of the general formula (V)

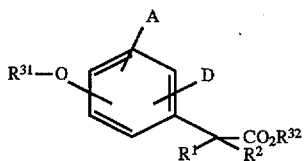

in which

A, D, $R^1$ and $R^2$ have the abovementioned meaning $R^{31}$ represents a typical hydroxy-protective group, preferably benzyl or tert-butyl, and $R^{32}$ represents hydrogen or represents $(C_1-C_4)$-alkyl, after this protective group has been split off by customary methods, are reacted with compounds of the general formula (VI)

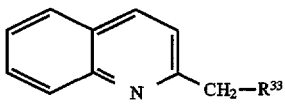

in which $R^{33}$ represents halogen, preferably bromine, in inert solvents, if appropriate in the presence of a base, and in the case of the acids the esters are hydrolysed.

Solvents for the etherification can be inert organic solvents which do not change under the reaction conditions. These include, preferably, ethers, such as, for example, dioxane, tetrahydrofuran or diethyl ether, halogenated hydrocarbons, such as methylene chloride, chloroform, carbon tetrachloride, 1,2-dichloroethane or trichloroethylene, hydrocarbons, such as benzene, xylene, toluene, hexane, cyclohexane or petroleum fractions, nitromethane, dimethylformamide, acetonitrile, acetone or hexamethylphosphoric acid triamide. It is also possible to employ mixtures of these solvents.

Bases which can be employed for the etherification are inorganic or organic bases. These include, preferably, alkali metal hydroxides, such as, for example, sodium hydroxide or potassium hydroxide, alkaline earth metal hydroxide, such as, for example, barium hydroxide, alkali metal carbonates, such as sodium carbonate or potassium carbonate, alkaline earth metal carbonates, such as calcium carbonate, or organic amines (trialkyl($C_1-C_6$)-amines), such as triethylamine, or heterocyclic bases, such as pyridine, methylpiperidine, piperidine or morpholine.

It is also possible to employ alkali metals, such as sodium, and hydrides thereof, such as sodium hydride, as bases.

The etherification is in general carried out in a temperature range from 0° C. to +150° C., preferably from +10° C. to +100° C.

The etherification is in general carried out under normal pressure. However, it is also possible to carry out the process under reduced pressure or increased pressure (for example in a range from 0.5 to 5 bar).

In general, 0.5 to 5, preferably 1 to 2, mol of halide are employed per mole of the reaction partner. The base is in general employed in an amount of 0.5 to 5 mol, preferably 1 to 3 mol, based on the halide.

The hydrolysis of the carboxylic acid esters is carried out by customary methods, by treating the esters with customary bases in inert solvents.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate. Sodium hydroxide or potassium hydroxide are particularly preferably employed.

Suitable solvents for the hydrolysis are water or the organic solvents customary for a hydrolysis. They include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

In general the hydrolysis is carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mole of the ester. Molar amounts of the reactants are particularly preferably used.

The compounds of the general formula (III) and (IV) are known.

The compounds of the general formulae (V) and (VI) are known.

The compounds of the general formula (I) according to the invention have an unforeseeable pharmacological action spectrum.

They can be used as active compounds in medicaments for reducing changes to vascular walls and for treatment of coronary heart diseases, cardiac insufficiency, disturbances in cerebral performance, ischaemic cerebral diseases, apoplexy, circulatory disturbances, disturbances in microcirculation and thromboses.

The proliferation of smooth muscle cells also plays a decisive role in the occlusion of vessels. The compounds according to the invention are capable of inhibiting this proliferation and therefore of preventing atherosclerotic processes.

The compounds according to the invention are distinguished by a reduction in the ApoB-100 associated lipoproteins (VLDL and its breakdown products, such as, for example, LDL), of ApoB-100 of triglycerides and of cholesterol. They therefore have valuable pharmacological properties which are superior compared with the prior art.

Surprisingly, the action of the compounds according to the invention comprises initially a reduction or complete inhibition of the formation and/or release of ApoB-100-associated lipoproteins from liver cells, which results in a reduction of the plasma VLDL level. This action in VLDL must be accompanied by a reduction in the plasma level of ApoB-100, LDL, triglycerides and cholesterol; several of the abovementioned risk factors which participate in changes to vascular walls are thus reduced at the same time.

The compounds according to the invention can therefore be employed for prevention and treatment of atherosclerosis, obesity, pancreatitis and constipation.

The invention also relates to a combination of oxyphenyl (phenyl)glycinol amides containing heterocyclic substituents of the general formula (I) with a glucosidase and/or amylase inhibitor for the treatment of familial hyperlipidemia, obesity (adipositas) and diabetes mellitus. Glucosidase and/or amylase inhibitors in the context of the invention are for example Acarbose, Adiposine, Voglibose (AQ-128), Miglitol, Emiglitate, MDL-25637, Camiglibose (MDL-73945), Tendamistate, A1-3688, Treslatin, Pradimicin-Q and Salboslatin. A combination of Acarbose, Miglitol, Emiglitate or Voglibose with one of the above-mentioned compounds of the general formula (I) is preferred.

I. Inhibition of the release of ApoB-100-associated lipoproteins

The test for detection of the inhibition of the release of ApoB-100-associated lipoproteins from liver cells was carried out in vitro with cultured liver cells, preferably with cells of the human line HepG2. These cells are grown under standard conditions in a medium for culture of eukaryotic cells, preferably in RPMI 1640, with 10% of foetal calf serum. HepG2 cells synthesize and secrete into the culture supernatant ApoB-100-associated lipoprotein particles, which in principle are built up in a similar manner to the VLDL and LDL particles which are to be found in the plasma.

These particles can be detected with an immunoassay for human LDL. This immunoassay is carried out with antibodies which have been induced against human LDL in the rabbit under standard conditions. The anti-LDL antibodies (rab-anti-LDL-ab) were purified by affinity chromatography on an immunosorbent with human LDL. These purified rab-anti-LDL-ab are adsorbed onto the surface of plastic. This adsorption is expediently carried out on the plastic surface of microtiter plates having 96 wells, preferably on MaxiSorp plates (Nunc). If ApoB-100-associated particles are present in the supernatant of HepG2 cells, these can bind to the insolubilized rab-anti-LDL-ab, and an immune complex which is bonded to the plastic surface is formed. Non-bonded proteins are removed by washing. The immune complex on the plastic surface is detected with monoclonal antibodies, which had been induced against human LDL according to standard conditions and purified. These antibodies were conjugated with the enzyme peroxidase (Boehringer, Mannheim). Peroxidase converts the colourless substrate TMB (Kirkegaard and Perry) into a coloured product in the presence of $H_2O_2$. After acidification of the reaction mixture with $H_2SO_4$, the specific light adsorption at 450 nm, which is a measure of the amount of ApoB-100-associated particles which had been secreted into the culture supernatant by the HepG2 cells, is determined.

Surprisingly, the compounds according to the invention inhibit the release of ApoB-100-associated particles. The $IC_{50}$ value indicates the concentration of substance at which the light adsorption is inhibited by 50% in comparison with the control (solvent control without substance).

TABLE

| Example No. | $IC_{50}[nM]$ |
| --- | --- |
| 15 | 500 |
| 53 | 250 |
| 127 | 130 |
| 141 | 20 |

2. Investigation of the inhibition of the proliferation of smooth muscle cells

The antiproliferative action of the compounds is determined using smooth muscle cells which are obtained from the aortas of rats by the media explant technique [R. Ross, J. Cell. Biol. 50, 172, 1971]. The cells are sown in suitable culture dishes, generally 96-well plates, and are cultured for 2–3 days in medium 199 with 7.5% of FCS and 7.5% of NCS, 2 mM L-glutamine and 15 mM HEPES, pH 7.4, in 5% of $CO_2$ at 37° C. Thereafter, the cells are synchronized by withdrawal of serum for 2–3 days and are then stimulated to growth with serum or other factors. At the same time, test compounds are added. After 16–20 hours, 1 µCi of $^3$H-thymidine is added, and after a further 4 hours the incorporation of this substance into the DNA of the cells which can be precipitated with TCA is determined. To determine the $IC_{50}$ values, the active compound concentration which, on sequential diluent of the active compound, causes half the maximum inhibition of the thymidine incorporation caused by 10% of FCS.

3. Determination of VLDL secretion in vivo on the hamster

The effect of the test substances on VLDL secretion in vivo is investigated on the hamster. For this purpose, golden hamsters are premedicated with atropine (83 mg/kg s.c.) and anaesthetized with Ketavet (83 mg/kg s.c.) and Nembutal (50 mg/kg i.p.). When the animals have become free tom reflexes, the v. jugularis is exposed and a cannula is inserted. 0.25 ml/kg of a 20% strength solution of Triton WR-1339 in physiological saline solution is then administered. This detergent inhibits the lipoprotein lipase and thus leads to an increase in the triglyceride level because of an absence of catabolism of secreted VLDL particles. This increase in triglycerides can be used as a measure of the rate of VLDL secretion. Blood is taken from the animals by puncture of the retroorbital venous plexus before and one and two hours after administration of the detergent. The blood is incubated at room temperature for two hours and then at 4° C. overnight in order to conclude the coagulation completely. Thereafter, it is centrifuged at 10,000 g for 5 minutes. The triglyceride concentration in the serum thus obtained is determined with the aid of a modified commercially obtainable enzyme test (Merckotest® Triglyceride No. 14354). 100 µl of test reagent are added to 100 µl of serum in 96-well plates and the mixtures are incubated at room temperature for 10 minutes. The optical density is then determined at a wavelength of 492 nm in an automatic plate reader (SLT-Spectra). Serum samples with too high a triglyceride concentration are diluted with physiological saline solution. The triglyceride concentration contained in the samples is determined with the aid of a standard curve measured in parallel. In this model test substances are administered either intravenously, immediately before administration of the detergent or orally or subcutaneously before initiation of the anaesthesia.

4. Inhibition of the intestinal absorption of triglycerides in vivo (rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before administration of the substance, and their food is then withdrawn. Drinking water is available to the animals ad libitum. The animals of the control group are given an aqueous tragacanth suspension or a tragacanth suspension which contains olive oil. The tragacanth-olive oil suspension is prepared with an Ultra-Turrax. The substances to be investigated are suspended in a corresponding tragacanth-olive oil suspension, likewise with the Ultra-Turrax, directly before administration of the substance.

Blood is taken from each rat by puncture of the retroorbital venous plexus before application of the stomach tube in order to determine basal serum triglyceride content. The tragacanth suspensions, tragacanth-olive oil suspensions without a substance (control animals) and the substances suspended in a corresponding tragacanth-olive oil suspension, are then administered to the fasting animals with a stomach tube. Further blood is taken for determination of the postprandial increase in serum triglycerides as a rule 1, 2 and 3 hours after application of the stomach tube.

The blood samples are centrifuged and, after isolation of the serum, the triglycerides are determined photometrically with an EPOS analyser 5060 (Eppendorf Gerätebau, Netlacier & Hinz GmbH, Hamburg). The triglycerides are determined completely enzymatically with a commercially available UV test.

The postprandial increase in serum triglycerides is determined by subtraction of the triglyceride pre-value of each animal from its corresponding postprandial triglyceride concentrations (1, 2 and 3 hours after administration).

The differences (in mmol/l) at each point in time (1, 2 and 3 hours) are averaged in the groups, and the means of the increase in serum triglycerides (ΔTG) of the animals treated with the substances are compared with those of the animals which were given only the tragacanth-oil suspension.

The course of the serum triglycerides of the control animals which were given only tragacanth is also calculated. The effect of the substance at each point in time (1, 2 or 3 hours) is determined as follows and stated in Δ% of the oil-loaded control.

$$\Delta\% \text{ Triglycerides} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the increase in triglycerides (Δ%) 2 h after a triglyceride loading in the serum of fasting rats. The increase in serum triglycerides of fat-loaded control animals based on the serum triglyceride level of tragacanth control animals corresponds to 100%. n=6 animals per group.

Statistical analysis is by the Student t-test after first checking the variances for homogeneity.

Substances which statistically significantly ($p < 0.05$) reduce the postprandial increase in serum triglycerides by at least 30% at a point in time, compared with that of the untreated control group, are regarded as pharmacologically active.

5. Inhibition of VLDL secretion in vivo (rat)

The action of the test substances on VLDL secretion is also investigated in the rat. For this, 500 mg/kg of body weight (2.5 mg/kg) of Triton WR-1339, dissolved in physiological saline solution, are administered intravenously into the tail vein of rats. Triton WR-1339 inhibits the lipoprotein lipase and thus leads to an increase in the triglyceride and cholesterol level by inhibition of VLDL catabolism. These increases can be used as a measure of the rate of VLDL secretion.

Blood is taken from the animals by puncture of the retroorbital venus plexus before and one and two hours after administration of the detergent. The blood is incubated at room temperature for 1 h for coagulation and the serum is isolated by centrifugation at 10,000 g for 20 s. The triglycerides are then determined photometrically at a wavelength of 540 nm with a commercially available coupled enzyme test (Sigma Diagnostics®, No. 339). The measurement is made at a wavelength of 546 nm with the aid of an enzyme test which is likewise coupled (Boehringer Mannheim®, No. 1442350). Samples with triglyceride or cholesterol concentrations which exceed the measurement range of the methods are diluted with physiological saline solution. The particular serum concentrations are determined with the aid of standard series measured in parallel. The test substances are administered orally, intravenously or subcutaneously immediately after the Triton injection.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, i.e. in amounts which are sufficient to achieve the stated dosage range.

The formulations are prepared, for example, by extending the active compounds with solvents and/or excipients, if appropriate using emulsifying agents and/or dispersing agents, and in the case of the use of water as a diluent, for example, organic solvents can be used as auxiliary solvents if appropriate.

The administration is carried out in the customary manner, preferably orally or parenterally, in particular perlingually or intravenously.

In the case of parenteral use, solutions of the active compound can be employed, using suitable liquid carrier materials.

In general, it has proved advantageous in the case of intravenous administration to administer amounts of about 0.001 to 1 mg/kg, preferably about 0.01 to 0.5 mg/kg of body weight, in order to achieve effective results, and in the case of oral administration the dosage is about 0.01 to 20 mg/kg preferably 0.1 to 10 mg/kg of body weight.

Nevertheless, it may be necessary to deviate from the amounts mentioned, and in particular as a function of the body weight or the nature of the administration route, of the behaviour of the individual towards the medicament, the nature of the formulation thereof and the time or interval at which administration takes place. Thus, in some cases it may be sufficient to manage with less than the abovementioned minimum amount, while in other cases the upper limit mentioned must be exceeded. In the event of administration of relatively large amounts, it may be advisable to distribute these into several individual doses over the day.

Definition of the isomer types:

4 dia=mixture of the four possible diastereomers with two centres of asymmetry in the molecule dia A=diastereomer having the higher $R_f$ value dia B=diastereomer having the lower $R_f$ value ent=enantiomer p1 2 ent dia=mixture of two enantiomerically pure diastereomers ent dia A=enantiomerically pure diastereomer having the higher $R_f$ value ent dia B=enantiomerically pure diastereomer having the lower $R_f$ value R=R enantiomer rac=racemate rac dia A=racemic diastereomer having the higher $R_f$ value rac dia B=racemic diastereomer having the lower $R_f$ value S=S enantiomer Abbreviations used:

Ac=acetyl

Bn=benzyl

Bz=benzoyl iBu=iso-butyl nBu=normal butyl sBu=secondary butyl tBu=tertiary butyl cDec=cyclo decyl DMF=N,N,-dimethylformamide
DMSO=dimethyl sulphoxide
cDodec=cyclo-dodecyl
Et=ethyl
cHept=cyclo-heptyl
cHex=cyclo-hexyl
HOBT=1-hydroxy-1H-benzotriazole
Me=methyl
Mes=mesyl
cNon=cyclo-nonyl
cOct=cyclo-octyl
cPent=cyclo-pentyl
nPent=normal pentyl
Ph=phenyl
cPr=cyclo-propyl
nPr=normal propyl
iPr=iso-propyl
THF=tetrahydrofuran
TMS=tetramethylsilane
pTol=para-tolyl
pTos=para-tosyl
cUndec=cyclo-undecyl

Solvent mixtures used

| Designation | Mobile phase | Ratio |
|---|---|---|
| A | methylene chloride:ethyl acetate | 1:1 |
| B | methylene chloride:methanol | 10:1 |
| C | methylene chloride:methanol | 20:1 |
| D | methylene chloride:methanol | 50:1 |
| E | methylene chloride:methanol | 25:1 |
| F | methylene chloride:ethanol | 20:1 |
| G | methylene chloride:methanol | 100:1 |
| H | petroleum ether:ethyl acetate | 2:1 |
| I | toluene:ethyl acetate | 4:1 |
| J | petroleum ether:acetone | 2:1 |
| K | methylene chloride:ethyl acetate | 5:1 |
| L | petroleum ether:acetone | 1:1 |
| M | methylene chloride:ethyl acetate | 4:1 |
| N | toluene:ethyl acetate | 1:1 |
| O | petroleum ether:ethyl acetate | 1:1 |
| P | petroleum ether:acetone | 3:1 |
| Q | toluene:ethyl acetate | 2:3 |
| R | toluene:ethyl acetate | 2:1 |
| S | methylene chloride:ethyl acetate | 10:1 |
| T | petroleum ether:ethyl acetate | 5:1 |
| U | methylene chloride:methanol | 5:1 |
| V | petroleum ether:ethyl acetate | 4:1 |
| W | ethyl acetate | |
| X | petroleum ether:ethyl acetate | 3:2 |
| Y | methylene chloride:ethanol | 50:1 |
| Z | methylene chloride:methanol | 19:1 |
| AA | toluene:ethanol | 30:1 |

Solvent mixtures used (continued)

| Designation | Mobile phase | Ratio |
|---|---|---|
| AB | toluene:ethanol | 15:1 |
| AC | methylene chloride:methanol:ethyl acetate | 90:10:1 |
| AD | methylene chloride:methanol:concentrated aqueous ammonia | 90:10:1 |
| AE | petroleum ether:ethyl acetate | 3:7 |
| AF | petroleum ether:ethyl acetate | 7:3 |
| AG | petroleum ether:ethyl acetate | 1:2 |
| AH | petroleum ether:ethyl acetate | 2:3 |
| AI | petroleum ether:ethyl acetate | 1:4 |
| AJ | methylene chloride:methanol | 9:1 |
| AK | toluene:acetone | 10:1 |
| AL | toluene:acetone | 40:1 |

Preparation instruction for the TLC mobile phase BABA 87.9 ml of an aqueous 0.06667 molar potassium dihydrogen phosphate solution and 12.1 ml of an aqueous 0.06667 molar disodium hydrogen phosphate solution are mixed. 60 ml of the solution thus prepared are shaken with 200 ml of n-butyl acetate, 36 ml of n-butanol and 100 ml of glacial acetic acid and the aqueous phase is removed. The organic phase is the mobile phase BABA.

Starting compounds

EXAMPLE 1

Methyl 2-amino-2-[2'-(1',3'-dithiolano)]acetate hydrochloride

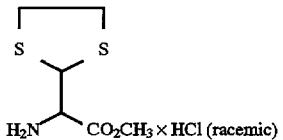

0.5 g (2.8 mmol) of 2-amino-2-[2'-(1',3'-dithiolano)]acetic acid (synthesis: M. P. Mertes. and A. A. Ramsey J. Med. Chem. 12, 342 (1969).) are reacted with 0.4 ml (5.6 mmol of thionyl chloride in 10 ml of methanol under reflux. After 8 hours, the mixture is cooled and evaporated to dryness in vacuo in a rotary evaporator, and residual solvent and excess reagents are then removed under a high vacuum over phosphorus pentoxide and solid sodium hydroxide.

Yield: 0.62 g $R_f$=0.32 (BABA) characteristic $^1$H-NMR signals (CD$_3$OD, 200 MHz, the solvent as the standard at 3.25 ppm): δ=4.36 (d, 1H); 5.17 (d, 1H) ppm.

The following compounds are obtained analogously to Example 1:

TABLE I $$\text{H}_2\text{N}-\underset{\text{L}}{\text{CH}}-\text{CO}_2\text{CH}_3 \times \text{HCl}$$

| Example No. | L/hydrochloride | $R_f$/solvent | Literature/distributor of the starting material |
|---|---|---|---|
| II | 2-hydroxyphenyl | 0.39/BABA | Precursor = acetamido lactone derivative; DE 21 62 717 |
| III | 4-cyclopropylphenyl | 0.01/AH | |
| IV | 4-biphenyl (Ph) | 0.01/AH | |
| V | 2-naphthyl | 0.01/AH | Precursor = H₂N–CH(COOH)–(2-naphthyl); US 4 474 780 |
| VI | 4-(morpholin-4-yl)phenyl, H₂H–CH–CO₂CH₃ | 0.21/E | Precursor = 4-(morpholin-4-yl)phenyl, H₂N–CH–COOH; DE 28 36 613 |
| VII | 5-methylfuran-2-yl | 0.27/BABA | Precursor = 5-methylfuran-2-yl, H₂N–CH–COOH; R. M. Williams et al., J. Org. Chem. 55, 3723 (1990). |

TABLE I-continued $$\underset{H_2N}{\overset{L}{\underset{|}{C}}}\underset{CO_2CH_3 \times HCl}{}$$

| Example No. | L/hydrochloride | $R_f$/solvent | Literature/distributor of the starting material |
|---|---|---|---|
| VIII | 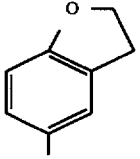 | 0.46/BABA | Precursor = 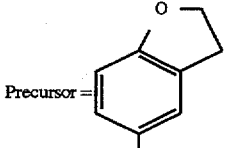<br>US 4 138 397 |
| IX | 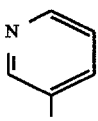 | 0.17/BABA | Precursor = 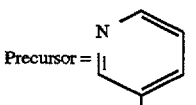<br>DE 25 40 804 |
| X | 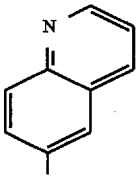 | 0.20/BABA | Precursor = 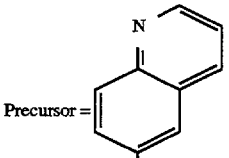<br>US 4 734 407 |
| XI | 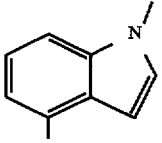 | 0.45/BABA | Precursor = 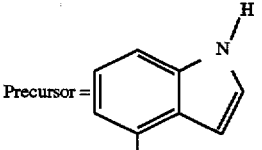<br>US 4 734 407 |
| XII | 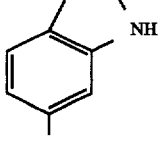 | 0.58/BABA | Precursor = 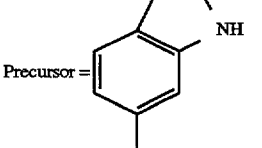<br>G. Schmidt et al. in "Recent Advances in Chemotherapy" Ed. D. Adam, H. Lode and E. Rubinstein, p.2428 et seq. Futuramed Publishers Munich, 1992. |
| XIII | 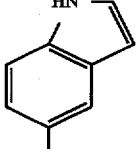 | 0.58/BABA | Precursor = 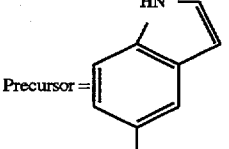<br>US 4 734 407 |

TABLE I-continued $$H_2N-\underset{L}{\overset{|}{C}}H-CO_2CH_3 \times HCl$$

| Example No. | L/hydrochloride | $R_f$/solvent | Literature/distributor of the starting material |
|---|---|---|---|
| XIV | (2-methyl-benzothiazol-yl)methanamine structure | 0.29/BABA | Precursor = benzothiazole with $H_2N$-CH-COOH; US 4 748 163 |
| XV | (methylthiophene) structure | 0.40/BABA | Precursor = $-H_2N$-CH(COOH)-thiophene; M. Hatanaka et al., J. Med. Chem. 16, 978 (1973). |

Example XVI

3-Fluorophenylglycinol

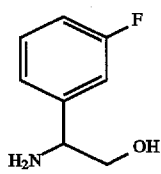

18 ml of anhydrous THF are added to 71 ml of a 1M lithium alanate solution in THF and the mixture is heated under reflux. After the heating bath has been removed, 6.0 g of 3-fluorophenylglycine (E. L. Compete Jr. D. A. Weinstein, Synthesis 1977, 852) are added in small portions, the mixture is heated under reflux for a further hour and a solution of 1.27 g of potassium hydroxide in 5.1 ml of water is then carefully added dropwise. After a further 15 minutes under reflux, the precipitate formed is filtered off hot with suction and washed several times with THF. The filtrate is concentrated substantially (vacuum/rotary evaporator), the residue is taken up in ethyl acetate, the mixture is dried with sodium sulphate and evaporated again and the residue is stirred with petroleum ether, whereupon the product slowly solidifies. After filtration with severe suction and removal of the residual solvent in vacuo, 6.0 g of product are obtained.

$R_f$=0.13 (B)

$^1$H-NMR (CD$_3$OD, 250 MHz, the solvent signal at 3.25 ppm serves as the standard): δ=3.48 (dd, 1H); 3.62 (dd, 1H); 3.89 (dd, 1H); 6.93 (m, 1H); 7.05–7.14 (m, 2H); 7.27 (m, 1H) ppm.

D,L-3-fluorophenylglycine is also commercially obtainable from K & K.

The following compounds are obtained analogously to Example XVI:

TABLE II $$H_2N-\underset{L}{\overset{|}{C}}H-CH_2-OH$$

| Example No. | L | $R_f$/solvent | Distributor of the starting material |
|---|---|---|---|
| XVII | 2-fluorophenyl | 0.18/B | Aldrich |
| XVIII | 4-fluorophenyl | 0.09/B | Fluka |
| XIX | 3-chlorophenyl | 0.23/B | K & K |
| XX | 4-chlorophenyl | 0.12/B | K & K |

Example XXI

E- and Z-(isoquinolin-1-yl)phenyl ketoxime

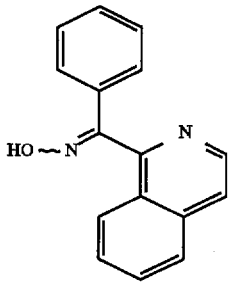

15.0 g of 1-benzoylisoquinoline (J. Knabe and A. Frie, Arch. Pharm. 306, 648 (1973).) and 8.94 g of hydroxyammonium chloride are boiled under reflux in 50 ml of pyridine for 4 hours. The cooling reaction mixture is stirred into 500 ml of water at room temperature. After the mixture has been subsequently stirred vigorously for 15 minutes, the precipitate is filtered off with suction, washed several times with water, finally filtered off under a very severe suction and then dried under a high vacuum over phosphorus pentoxide at about 80° C.

Yield: 15.9 g $R_f$=0.44 (C)

MS (Chemical ionization with $NH_3$): m/z=249 ([M+H]$^+$, 17%), 248 ($M^+$, 18%).

The following compounds are prepared analogously to the preparation instructions of Example XXI:

TABLE III

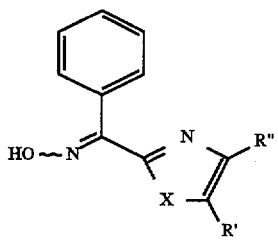

| Ex. No. | X | R' | R" | $R_f$ (solvent) | Literature for the starting material |
|---|---|---|---|---|---|
| XXII | S | $CH_3$ | $CH_3$ | 0.73/0.53 (C) | Y. Oka et al., Chem. Pharm. Bull. 18, 527 (1970) |
| XXIII | NH | H | H | 0.30/0.26 (B) | A. Sonn et al., Chem. Ber. 66, 1900 (1933) |

Example XXIV 1-(α-Aminobenzyl)-isoquinoline

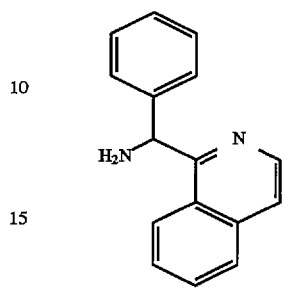

15.72 g of the compound from Example XXI and 6.05 g of ammonium acetate are suspended in 236 ml of concentrated aqueous ammonia solution, 157 ml of water and 157 ml of ethanol, and a total of 22.7 g of zinc dust are then added in portions under reflux over a period of one hour. After 3 hours under reflux, the mixture is cooled to room temperature, a pH of 14 is established with 10% strength aqueous sodium hydroxide solution (10 g of solid NaOH per 90 ml of water) and the mixture is extracted several times with ether. The organic phases are dried with sodium sulphate, evaporated and freed from the residual solvent under a high vacuum.

Yield: 12.4 g $R_f$=0.13 (B) characteristic $^1$H-NMR signal ($CDCl_3$, 250 MHz, TMS): δ=5.95 (s, 1H, C$\underline{H}$—$NH_2$) ppm.

The following compounds can be prepared analogously to the preparation of Example XXIV:

TABLE IV

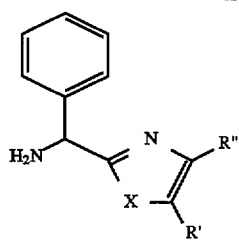

| Ex. No. | X | R' | R" | $R_f$ (solvent) | Ex. No. of the starting material |
|---|---|---|---|---|---|
| XXV | S | $CH_3$ | $CH_3$ | 0.38 (C) | XXII |
| XXVI | NH | H | H | 0.13 (B) | XXIII |

TABLE V

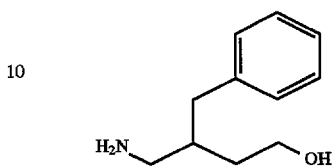

| Example No. | L | $R_f$/solvent | Literature/distributor of the starting material |
|---|---|---|---|
| XXVII | Me (4-methylphenyl) | 0.10 (B) | Precursor = Me-C6H4-CH(NH2)CO2Me; F. Rose-Munch et al., J. Organomet. Chem. 415, 223 (1991) |
| XXVIII | methylenedioxyphenyl | 0.01 (O) | Precursor = (methylenedioxyphenyl)-CH(NH2)CO2Me; G. H. Hakimelahi and G. Just, Can. J. Chem. 57, 1932 (1979) |
| XXIX | 4-biphenyl | 0.19 (U) | Precursor = Ex. No. IV |

Example XXX (R,S)-2-Benzyl-4-hydroxy-butyric acid amide

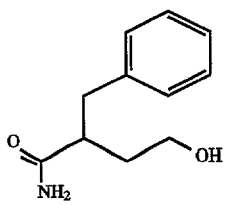

12.0 g of (R,S)-2-Benzyl-4-hydroxy-γ-butyrolactone (Z. Jedlinski et al., J. Org. Chem. 52, 4601 (1987).) are reacted in a saturated solution of ammonia in methanol at room temperature. After 20 hours, the solvent is evaporated off in vacuo with the excess reagent, the residue is taken up again in methanol and the mixture is evaporated in order to remove the excess ammonia completely. The resulting solid is subsequently dried in a desiccator over phosphorus pentoxide.

Yield: 13.5 g
$R_f$=0.39 (B)

MS (EI): m/z=193 (5%, M⁺), 176 (25%, M⁺—NH₃); 162 (9%, M⁺—CH₂OH); 148 (56%, M⁺—NH₃—CO); 91 (100%, $C_6H_5CH_2^+$).

Example XXXI

4-Amino-(R,S)-3-benzyl-butan-1-ol 11.6 g of the compound from Example XXX are reacted with 4.55 g of lithium alanate in 100 ml of THF (anhydrous) at room temperature. After 20 hours, the reaction is interrupted by addition of 45 ml of saturated aqueous sodium chloride solution, and the mixture is subsequently stirred vigorously for one hour and filtered off with suction over kieselguhr. The eluate is taken up in toluene (addition of ethanol may be necessary for complete dissolation) and the water is carried off with the organic solvent by evaporation, taking up in toluene again and renewed evaporation.

Yield: 11.3 g $R_f$=0.23 (methylene chloride: methanol: glacial acetic acid=5:1:1)

The crude product is reacted further without purification.

The synthesis of the precursor carboxylic acids are known, in this context of, for example, U.S. Pat. No. 4,929,629, U.S. Pat. No. 4,970,215, EP 509 359, U.S. Pat. No. 4,929,626, U.S. Pat. No. 5,091,392, U.S. Pat. No. 5,126,354, EP 414 078, EP 529 450).

Example XXXII and Example XXXIII 2-(R)- and 2-(S)-2-{4-[(Quinolin-2-yl)methoxy]phenyl}-2-cyclopentyl-acetic acid (R)-phenylglycinolamide

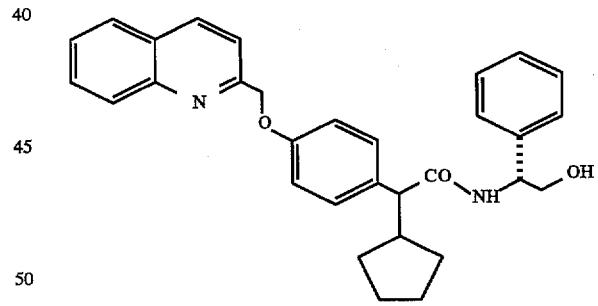

2.5g (6.9 mmol) of racemic 2-{4-[(quinolin-2-yl) methoxy]phenyl}-2-cyclopentyl acetic acid (synthesis: U.S. Pat. No. 4,970,215) are dissolved in 25 ml of anhydrous N,N-dimethylformamide, 2.88 ml (20.8 mmol) of triethylamine and 604.7 µl (7.6 mmol) of mesyl chloride are added and the mixture is subsequently stirred at −60° C. for 3 hour under argon as an meat gas. Thereafter, 1.14 g (8.3 mmol) of (R)-phenylglycinol (commercially obtainable from Aldrich) and 0.84 g (6.9 mmol) of 4-(N,N-dimethylamino)-pyridine, dissolved in 20 ml of anhydrous N,N-dimethylformamide, are added and the mixture is subsequently stirred for a total of 16 hours while slowly warning to room temperature. Ethyl acetate and water are added to the reaction mixture and the aqueous phase is brought to a pH of about 2 with 1M hydrochloric acid. The organic phase is extracted several times with dilute hydrochloric acid (pH~2), washed with water and then extracted several times with 0.1M aqueous sodium hydroxide solution. The organic phase is again washed with water and then dried with anhydrous magnesium sulphate and evaporated. Column chromatography (silica gel 60, Merck 40–63 μm, mobile phase, petroleum ether, ethyl acetate from 5:1 to 1:1) is carried out to separate the components.

Example XXXII:

$R_f$=0.12 (K)
Yield: 1.1 g

Example XXXIII:

$R_f$=0.08 (K)
Yield: 1.0 g

The absolute configuration of the enantiomercially pure carboxylic acids (starting material for Examples XXXII and XXXIII) is known (EP 509 359), so that the absolute configuration of the products (Example XXXII and XXXIII) can be deduced therefrom. The $^1$H-NMR spectra of the two diastereomeric products (200 MHz, $d_6$-DMSO, TMS for Example XXXII/250 MHz, $d_6$-DMSO, TMS for Example XXXIII) shows significant differences in the aromatic range:

the H signals of the phenyl radical of the phenylglycinolamide from Example XXXII are thus at about 7.1 ppm, and in the ease of Example XXXIII they are at about 7.3 ppm. This finding can be applied to many derivatives of this type.

Example XXXIV 2-(S)-2-{4-[(Quinolin-2-yl)methoxy]phenyl}-2-cycloheptyloacetic acid (R)-phenylglycinolamide

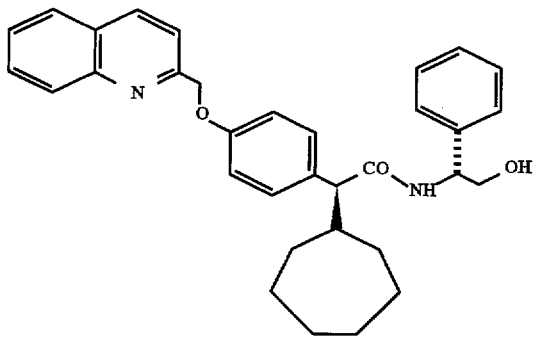

The title compound is prepared analogously to the instructions of Examples XXXII and XXXIII.

Melting point=176° C.

Example XXXV (2-Hydroxy-phenyl)-glycinol hydrochloride

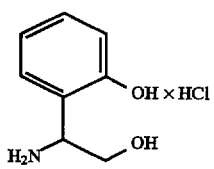

2.18 g (10 mmol) of (2-hydroxy-phenyl)-glycine methyl ester hydrochloride are dissolved in 20 ml of dry THF and reacted with 3.34 g (33 mmol) of triethylamine and 2.39 g (22 mmol) of trimethylchlorosilane at room temperature (25° C.) for 18 hours. The precipitate formed is filtered off with suction, and washed with dry THF and the filtrate is reacted with lithium alanate (0.76 g/38.0 mmol) at 25° C. Thereafter, excess reagent is filtered off with suction, the residue is rinsed with dry THF, water is added and the mixture is diluted with ether (pH~10). The aqueous phase is brought to pH=2 with 2M hydrochloric acid, washed with ether and lyophilized Yield 1.20 g (6.3 mmol)

$R_f$=0.38 (BABA)

The compounds listed in Table VI are prepared analogously to the instructions of Example XXXV.

TABLE VI

| Example No. | $R^{34}$ | $R_f$ (mobile phase) |
|---|---|---|
| XXXVI | 3-OH | 0.23 (U) |
| XXXVII | 4-OH | 0.34 (BABA) |

The compounds of Table VII are prepared analogously to the instructions of Example No. 1:

TABLE VII

| Example No. | L | m.p. [°C.] $R_f$ (solvent) |
|---|---|---|
| XXXVIII | Cl-phenyl | 0.01 (AH) |
| XXXIX | pyrrolidinyl-phenyl | 0.00 (AH) |
| XL | SO$_2$Me-phenyl | 0.01 (AH) |
| XLI | CF$_3$-phenyl | 0.01 (AH) |

TABLE VII-continued

H₂N–CH(L)–CO₂CH₃ × HCl

| Example No. | L | m.p. [°C.] R_f (solvent) |
|---|---|---|
| XLII | 2-OPh, F-phenyl | 0.01 (AH) |
| XLIII | 4-OCF₃-phenyl | 0.01 (AH) |
| XLIV | 2,3-(OH)₂-phenyl | 0.01 (AH) |

PREPARATION EXAMPLES

Example 1

(2S)-2-[4-(Quinolin-2-yl-methoxy)-phenyl]-2-cyclopentyl-acetic acid (R)-(O-acetyl)-phenylglycinolamide

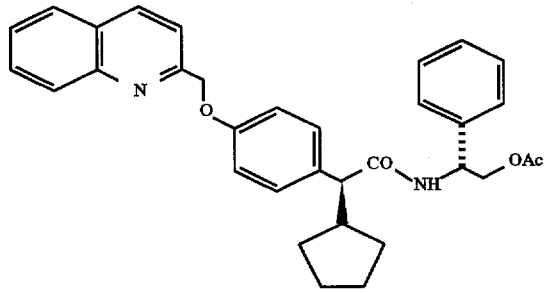

30 mg of the compound from Example XXXII are reacted with 13.4 μl of acetyl chloride and 15.1 μl of pyridine in 20 ml of methylene chloride at room temperature. After 20 hours, the mixture is poured onto 1M hydrochloric acid and the organic phase is then washed with a buffer solution of pH 2 (ready-to-use buffer solution, pH=2.00, citrate-hydrochloric acid based on SMR of NIST, Merck order No. 9433.1000). The organic phase is dried with magnesium sulphate and evaporated and the residue is freed from the residual solvent under a high vacuum.

Yield: 29 mg.

R_f=0.47 (F)

Example 2

(2S)-2-[4-(Quinolin-2-yl-methoxy)phenyl]-2-cyclopentyl-acetic acid (S)-(O-acetyl)-phenyl-glycinol-amide

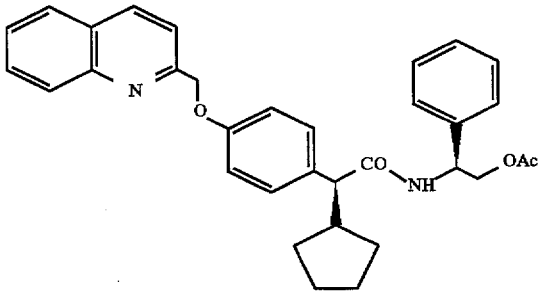

(2S)-2-[4-(Quinolin-2-yl-methoxy)phenyl]-2-cyclopentyl-acetic acid (S)-phenylglycinolamide U.S. Pat. No. 4,970,215) is reacted analogously to the instructions of Example 1 to give the title compound.

Melting point: 143° C.

The compounds from Tables 1 and 2 can be prepared analogously to Example XXXII and XXXIII:

TABLE 1

[Structure: quinoline-CH₂-O-phenyl-CH(cyclopentyl)-CO-NH-CH(R³⁵-phenyl)-CO₂CH₃, with positions 1 and 2 marked]

| Example No. | 1 | 2 | R³⁵ | R_f/solvent | Example No./literature for the precursor amine |
|---|---|---|---|---|---|
| 3 | rac | rac | 2-OH | 0.25/D | Example II |
| 4 | rac | rac | 3-OH | 0.19/D | DE 22 04 117 |
| 5 | rac | rac | 4-OH | 0.18/D | EP 530 879 |
| 6 | rac | rac | 2-OMe | 0.31/D | S. J. Daum et al., Syn. Commun. 11, 1 (1981). |
| 7 | rac | rac | 3-OMe | 0.15/G | DE 23 09 180 |
| 8 | rac | rac | 4-OMe | 0.35/D | H. E. Baumgarten et al., J. Org. Chem. 31, 3708 (1966). |
| 9 | rac | rac | 4-tBu | 0.36/H | WO 91/08 704 |
| 10 | rac | rac | 4-cPr | 0.41/I | Example III |
| 11 | rac | rac | 4-Ph | 0.53/J | Example IV |
| 12 | rac | rac | 3,4-(cyclohexenyl fused) | 0.44/I | Example V |
| 13 | rac | rac | 4-(morpholin-4-yl) | 0.63/E | Example VI |

TABLE 2

[Structure: quinoline-CH₂-O-phenyl-CH(cyclopentyl)-CO-NH-CH(R³⁵-phenyl)-CH₂OH]

| Example No. | 1 | 2 | R³⁵ | R_f/solvent | Example No. of the precursor |
|---|---|---|---|---|---|
| 14 | rac | rac | 2-F | 0.61/A | Example XVII |
| 15 | rac | rac | 3-F | 0.57/A | Example XVI |
| 16 | rac | rac | 4-F | 0.50/A | Example XVIII |
| 17 | rac | rac | 3-Cl | 0.61/B | Example XIX |
| 18 | rac | rac | 4-Cl | 0.72/B | Example XX |
| 19 | rac | rac | 3,4-OCH₂O— | 0.48/A | Example XXVIII |
| 20 | rac | rac | 4-Me | 0.60/A | Example XXVII |

Example 21

2-{4-[Quinolin-2-yl-methoxy]phenyl}-2-cyclopentyl acetic acid [4-tert-butylphenyl]glycinol-amide

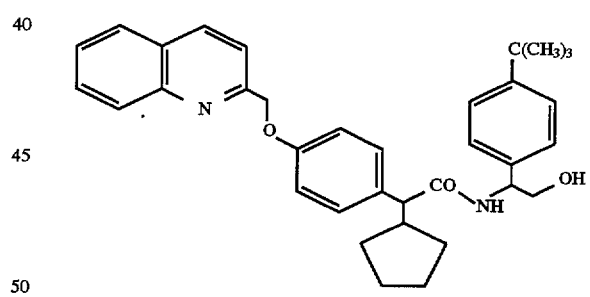

0.78 mg of the compound from Example 9 is reacted in 10 ml of anhydrous THF with 3.05 ml of a 1M solution of lithium alanate in THF at room temperature. After 100 minutes, the mixture is poured onto ethyl acetate/water, the organic phase is washed with saturated aqueous sodium chloride solution and the organic phase is dried with magnesium sulphate and evaporated to dryness. The resulting crude product is purified by column chromatography (silica gel 60, Merck 40–63 µm, first methylene chloride and then a mixture of methylene chloride:methanol of first 200:1 and then 100:1, 50:1 to 20:1 is used as the mobile phase).

Yield: 0.38 g $R_f$=0.46 (E)

The compounds from Table 3 are prepared analogously to the instructions of Example 21:

TABLE 3

| Example No. | 1 | 2 | R36 | Rf/solvent | Example No. of the precursors |
|---|---|---|---|---|---|
| 22 | rac | rac | 4-cPr | 0.33/E | Example 10 |
| 23 | rac | rac | 4-Ph | 0.27/A | Example 11 |
| 24 | rac | rac | 3,4- (fused ring) | 0.42/E | Example 12 |
| 25 | rac | rac | 4-(N-morpholinyl) | 0.63/B | Example 13 |
| 26 | rac dia A | 4-Ph | | 0.36/F | Example 11 |
| 27 | rac dia B | 4-Ph | | 0.36/F | Example 11 |
| 28 | rac | rac | 2-OH | 0.40/C | Example 3 |
| 29 | rac | rac | 3-OH | 0.40/B | Example 4 |
| 30 | rac | rac | 4-OH | 0.34/B | Example 5 |
| 31 | rac | rac | 2-OMe | 0.09/D | Example 6 |
| 32 | rac dia A | 3-OMe | | 0.29/C | Example 7 |
| 33 | rac | rac | 3-OMe | 0.29/C | Example 7 |
| 34 | rac | rac | 4-OMe | 0.36/C | Example 8 |

TABLE 4

| Example No. | 1 | 2 | Het | Rf/solvent | Example No./literature for the precursor amine |
|---|---|---|---|---|---|
| 35 | rac | rac | dimethylfuran (Me...O...Me) | 0.97/K | Example VII |

TABLE 4-continued

| Example No. | 1 | 2 | Het | Rf/solvent | Example No./literature for the precursor amine |
|---|---|---|---|---|---|
| 36 | rac | rac | benzofuran-CH2 | 0.40/O | Example VIII |
| 37 | rac | rac | pyridin-3-yl | 0.30/K | Example IX |
| 38 | rac | rac | quinolin-6-yl | 0.24/P | Example X |
| 39 | rac | rac | indol-4-yl (NH) | 0.67/C | Example XI |
| 40 | rac | rac | indol-3-yl CH2 (NH) | 0.43/B | Example XII |
| 41 | rac | rac | indol-3-yl (HN) | 0.38/C | Example XIII |
| 42 | rac | rac | benzothiazol-2-yl NH2 | 0.30/Q | Example XIV |

TABLE 4-continued

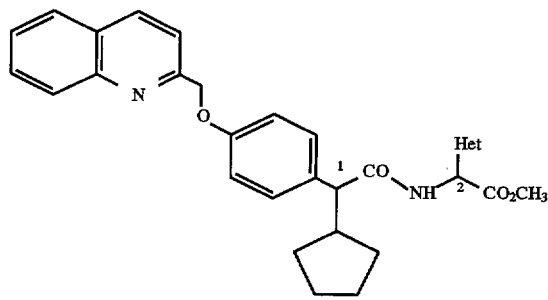

| Example No. | 1 | 2 | Het | R_f/solvent | Example No./ literature for the precursor amine |
|---|---|---|---|---|---|
| 43 | rac | rac | (thiophene) | 0.65/K | DE 22 04 117 |
| 44 | rac | rac | (thiophene) | 0.60/K | Example XV |

TABLE 4-continued

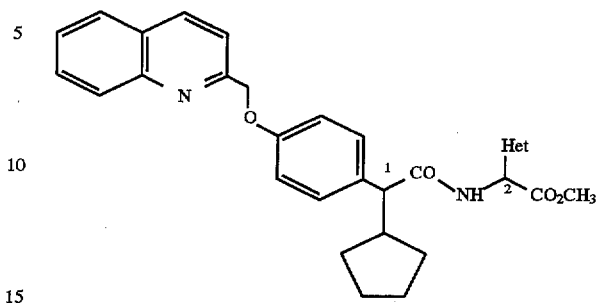

| Example No. | 1 | 2 | Het | R_f/solvent | Example No./ literature for the precursor amine |
|---|---|---|---|---|---|
| 45 | rac | rac | (dithiolane) | 0.50/R | Example I |

TABLE 5

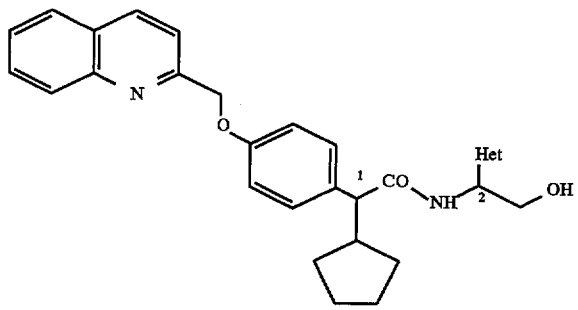

| Example No. | 1 | 2 | Het | R_f/solvent | Example No. precursor | Preparation analogously to Example No. |
|---|---|---|---|---|---|---|
| 46 | rac | rac | (2,5-dimethylfuran) | 0.2/K | Example 35 | 21 |
| 47 | rac | rac | (benzodioxole) | 0.48/A | Example XXVIII | XXXII, XXXIII |

TABLE 5-continued
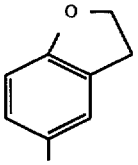
| Example No. 1 | 2 | Het | $R_f$/solvent | Example No. precursor | Preparation analogously to Example No. |
|---|---|---|---|---|---|
| 48 | rac rac | 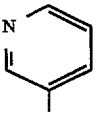 | 0.22/E | Example 36 | 21 |
| 49 | rac rac | 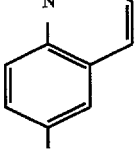 | 0.33/B | Example 37 | 21 |
| 50 | rac rac | 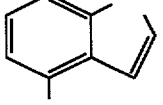 | 0.2/L | Example 38 | 21 |
| 51 | rac rac | 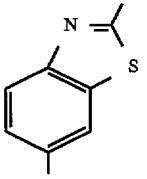 | 0.2/C | Example 39 | 21 |
| 52 | rac rac | 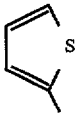 | 0.39/B | Example 42 | 21 |
| 53 | rac rac | 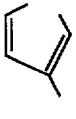 | 0.14/K | Example 43 | 21 |
| 54 | rac rac |  | 0.1/M | Example 44 | 21 |
| 55 | rac rac | | 0.36/N | Example 45 | 21 |

TABLE 6

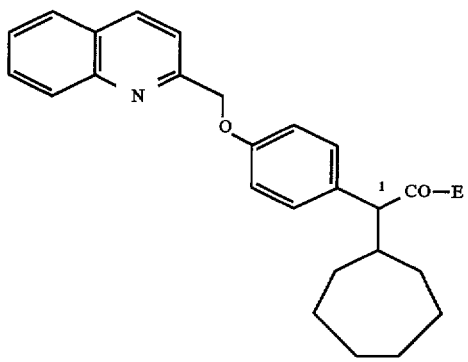

| Example No. | 1 | E | $R_f$/solvent | Distributor/literature/ Example No. of the starting material | Analogously to instructions in Example No. |
|---|---|---|---|---|---|
| 56 | S | (rac) thiophene-CH(NH-)CO₂CH₃ | 0.35/H | DE 22 04 117 | Example XXXII/ XXXIII |
| 57 | S | (rac) thiophene-CH(NH-)CO₂CH₃ | 0.33/S | Example XV | Example XXXII/ XXXIII |
| 58 | S | (rac) thiophene-CH(NH-)CH₂OH | 0.2/0.14/M | Example 56 | Example 21 |
| 59 | S | (rac) thiophene-CH(NH-)CH₂OH | 0.21/0.14/M | Example 57 | Example 21 |
| 60 | S | (rac) biphenyl-CH(NH-)CH₂OH | 0.3/0.25/D | Example XXIX | Example XXXII/ XXXIII |

TABLE 6-continued

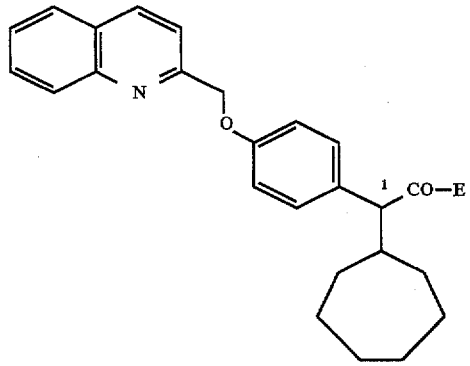

| Example No. | 1 | E | R$_f$/solvent | Distributor/literature/ Example No. of the starting material | Analogously to instructions in Example No. |
|---|---|---|---|---|---|
| 61 | S | (dia A) phenyl-biphenyl-CH(NH—)CH2OH | 0.30/D | Example XXIX | Example XXXII/ XXXIII |
| 62 | S | (dia B) phenyl-biphenyl-CH(NH—)CH2OH | 0.25/D | Example XXIX | Example XXXII/ XXXIII |

TABLE 7

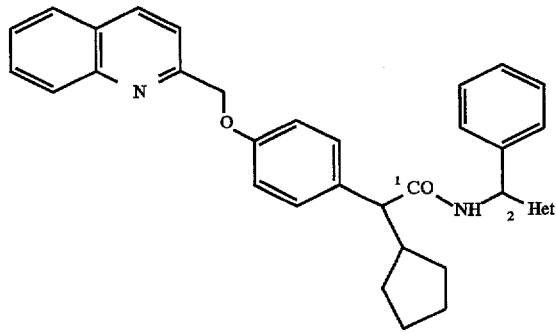

| Example No. | 1 | 2 | Het | R$_f$/solvent | Example No./Literature for the precursor amine |
|---|---|---|---|---|---|
| 63 | rac | rac | 2-pyridyl | 0.31/J | E. Niemers et al., Synthesis 1976, 593. |

TABLE 7-continued

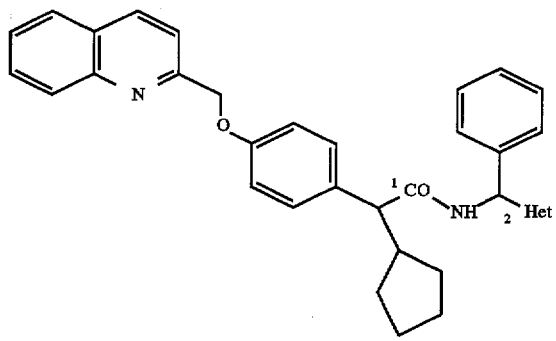

| Example No. | 1 | 2 | Het | $R_f$/solvent | Example No./Literature for the precursor amine |
|---|---|---|---|---|---|
| 64 | rac | rac | (3-pyridyl-CH2-) | 0.18/J | E. Niemers et al., Synthesis 1976, 593. |
| 65 | rac | rac | (4-pyridyl-CH2-) | 0.18/J | E. Niemers et al., Synthesis 1976, 593. |
| 66 | rac | rac | (isoquinolinyl) | 0.37/J | Example XXIV |
| 67 | rac | rac | (benzoxazol-2-yl) | 0.59/M | T.P. Sycheva et al., Chem. Heterocycl. Compounds 1966, 529. |
| 68 | rac | rac | (4,5-dimethylthiazol-2-yl) | 0.65/B | Example XXV |
| 69 | rac | rac | (benzothiazol-2-yl) | 0.61/M | US 44 25 338 |
| 70 | rac | rac | (1-methylbenzimidazol-2-yl) | 0.61/B | V. M.. Aruyzina et al., Chem. Heterocycl. Compounds 1966, 460. |
| 71 | rac | rac | (benzimidazol-2-yl) | 0.17/K | Samia M. Rida et al., Pharmazie 41, 563 (1986). |
| 72 | rac | rac | (imidazol-2-yl) | 0.25/A | Example XXVI |

Example 73

2-[4-(Quinolin-2-yl-methoxy)phenyl]-2-cycloheptyl-acetic acid (phenylglycine ethyl ester)-amide

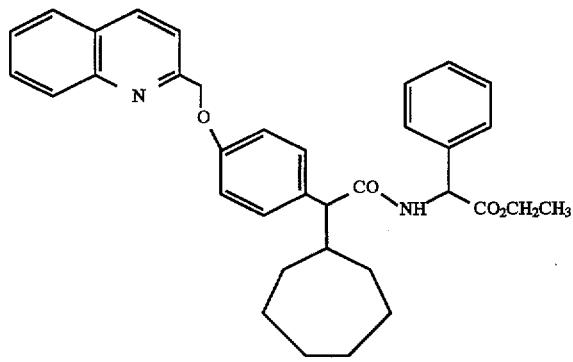

(R,S)-2-[4-(Quinolin-2-yl-methoxy)phenyl]-2-cycloheptyl-acetic acid (U.S. Pat. No. 4,970,215) and D,L-phenylglycine ethyl ester (Maybridge) are reacted with one another analogously to the preparation instructions of Examples XXXII and XXXIII $R_f$=0.12 (T)

Example 74

2-[4-(Quinolin-2-yl-methoxy)phenyl]-2-cycloheptyl-acetic acid (phenylglycine)-amide

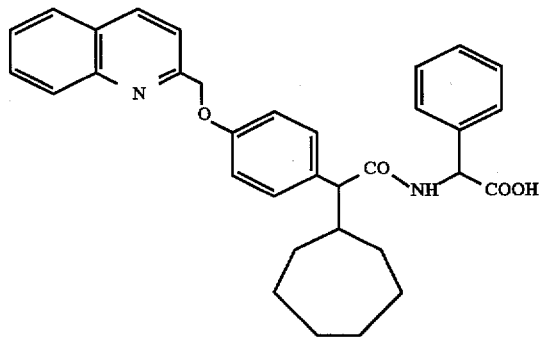

18.2 g of the compound from Example 73 are reacted with 160 ml of aqueous 2M sodium hydroxide solution in 40 ml of ethanol under reflux. After 2.5 hours, most of the ethanol content is removed in vacuo. The partly concentrated reaction mixture is diluted with water and extracted several times with ether. Thereafter, the residual content of organic solvent is stripped off from the aqueous phase in vacuo, a pH of 2 is established with 2M hydrochloric acid at 0° C. and the precipitate which is obtained is filtered off with suction, The precipitate is washed several times with water and, after the last filtration suction, is dried in vacuo over phosphorus pentoxide and solid sodium hydroxide.

Yield: 11.8 g $R_f$=0.21 (B)

Example 75

2-[4-(Quinolin-2-yl-methoxy)-phenyl]-2-cycloheptyl acetic acid N-(phenylglycinamide)amide

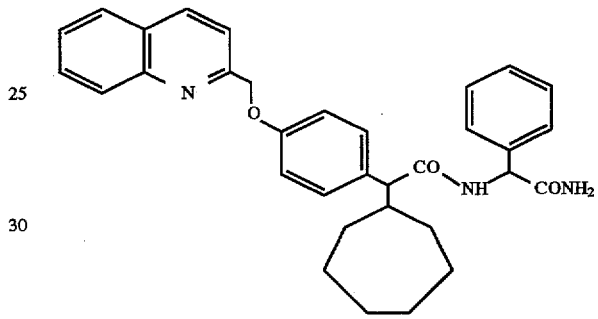

200 mg of the compound from Example 73 is dissolved in a saturated solution of ammonia in methanol and reacted under reflux for one day. The reaction mixture is evaporated in vacuo and finally dried over phosphorus pentoxide under a high vacuum.

Yield: 190 mg $R_f$=0.28 (C)

TABLE 8

[Structure: quinolin-2-yl-methoxy-phenyl-cycloheptyl-acetic acid amide core with R$^{37}$ substituent, with positions labeled 1 and 2]

| Ex. No. | 1 | 2 | R$^{37}$ | R$_f$/solvent | Literature/Ex. No. of the starting material | Preparation analogously to Ex. No. |
|---|---|---|---|---|---|---|
| 76 | rac | rac | —CONHCH$_3$ | 0.39/C | Example 73 | 75** |
| 77 | rac | rac | —CON(CH$_3$)$_2$ | 0.33/D | Example 74 | XXXII/XXXIII |
| 78 | rac | rac | —CONHnBu | 0.15/D | Example 73 | 75** |
| 79 | rac | rac | —CO—NH—CH$_2$CH$_2$—OH | 0.55/B | Example 73 | 75** |
| 80 | rac | rac | —CO—NH—CH$_2$CH$_2$—NH$_2$ | 0.3/U | Example 73 | 75*** |
| 81 | rac | rac | —CO—NH—CH$_2$—CO$_2$CH$_3$ | 0.53/C | Example 74 | XXXII/XXXIII |
| 82 | rac | rac | —CO—NH—CH$_2$—COOH | 0.2/B | Example 81 | 74 |
| 83 | rac | rac | —CO—NH—cyclohexyl | 0.38/C | Example 74 | XXXII/XXXIII |
| 84 | rac | rac | —CONH—phenyl | 0.28/D | Example 74 | XXXII/XXXIII |
| 85 | rac | rac | —CO—N(piperidinyl) | 0.18/D | Example 74 | XXXII/XXXIII |
| 86 | rac | rac | —CO—N(morpholinyl) | 0.41/D | Example 74 | XXXII/XXXIII |
| 87 | rac | rac | —CO—N(piperazinyl-N—Boc) | 0.34/D | Example 74* | XXXII/XXXIII |

*the precursor amine (tert-butyl 1-piperazinecarboxylate) is commercially obtainable from Aldrich.
**the reaction solvent is ethanol
***the amine to be reacted is the reaction solvent.

2-[4-(Quinolin-2-yl-methoxy)phenyl]-2-cycloheptyl-acetic acid N-[α-(piperazin-1-yl-carbonyl)benzyl]amide

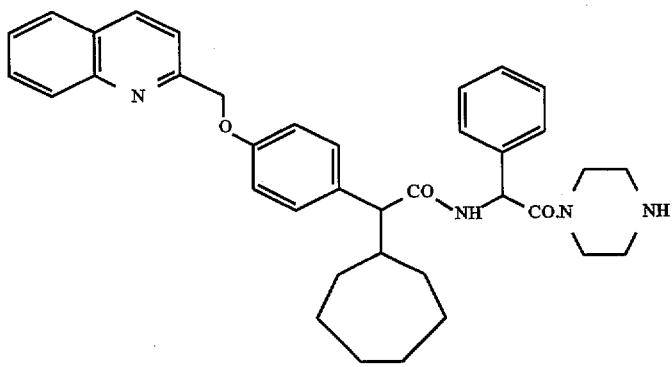

0.63 g of the compound from Example 87 is dissolved in 5 ml of ethyl acetate and reacted with 8 ml of 4M hydrochloric acid at room temperature. After 23 hours, ethyl acetate is added and the organic phase is extracted with 2M hydrochloric acid. The acid aqueous phase is freed from the organic residual solvent in vacuo and brought to pH 14 with 10% strength sodium hydroxide solution (10 g of solid NaOH in 90 ml of water) at about 10° C. The precipitate obtained is filtered off with suction, washed with water and dried in vacuo over phosphorus pentoxide.

Yield: 0.48 g $R_f$=0.19 (C)

Example 89

2-[4-(Quinolin-2-yl-methoxy)phenyl]-2-cycloheptyl-acetic acid N-[α-(4-N-acetylpiperazin-1-yl-carbonyl)benzyl]amide in 4 ml of methylene chloride at room temperature. After 1.5 hours, the mixture is extracted with a buffer of pH 4, the aqueous phase is shaken with methylene chloride and, after drying with sodium sulphate, the organic phase is evaporated. The crude product is purified by column filtration (silica gel 60, Merck 63–200 μm, methylene chloride).

Yield: 160 mg $R_f$=0.36 (methylene chloride: methanol=20:1)

Example 90

2-[4-(Quinolin-2-yl-methoxy)-phenyl]-2-cycloheptyl-acetic acid N-[α-(4N-methanesulphonyl-piperazin-1-yl-carbonyl)benzyl]amide

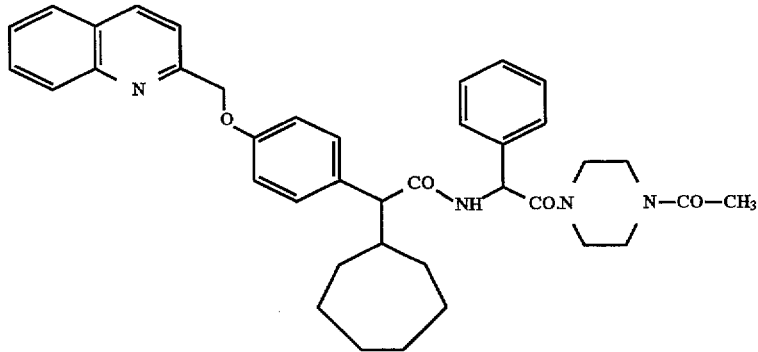

150 mg of the compound from Example 88 are reacted with 0.04 ml of triethylamine and 0.018 ml of acetyl chloride

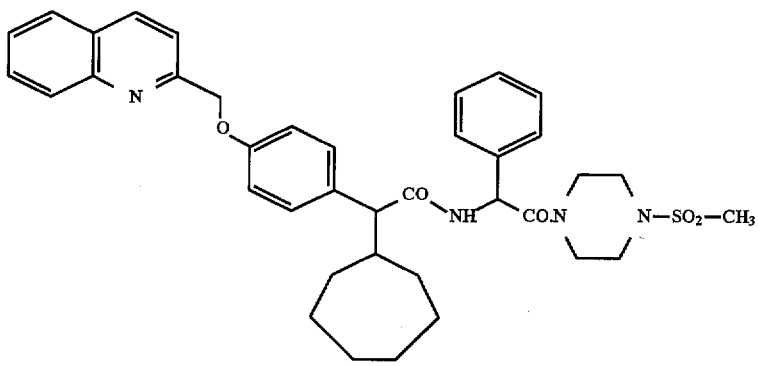

The compound from Example 88 is reacted with methanesulphonyl chloride analogously to the preparation of Example 89.

TABLE 9

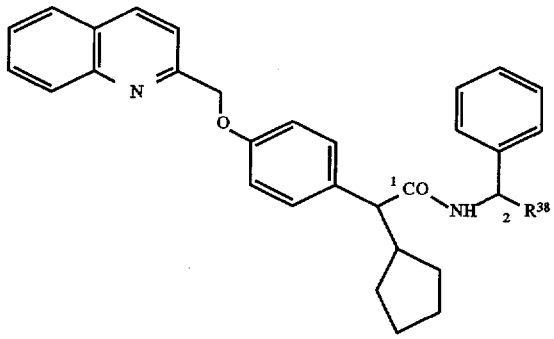

| Ex. No. | 1 | 2 | $R^{38}$ | $R_f$/solvent/ melting point | Distributor/literature of the precursor amines | Preparation analogously to Ex. No. |
|---|---|---|---|---|---|---|
| 91 | S | R | —CO$_2$CH$_3$ | 0.43/X | Nipkayaku | XXXII/XXXIII |
| 92 | S | R | —COOH | m.p. = 194–196° C. | Example 91 | Example 74 |
| 93 | rac | rac | —CO$_2$C$_2$H$_5$ | 0.5/D | Maybridge | XXXII/XXXIII |
| 94 | S | R | —CH$_3$ | m.p. = 146° | Aldrich | XXXII/XXXIII |
| 95 | rac | rac | —C$_2$H$_5$ | 0.29/D | Norse | XXXII/XXXIII |
| 96 | S | rac | —CONH$_2$ | 0.26/Z | Example 91 | Example 75 |
| 97 | rac | rac | —CONHCH$_3$ | 0.49/C | Example 93 | Example 75* |
| 98 | rac | rac | —CONH~~~OH | 0.56/B | Example 93 | Example 75* |
| 99 | rac | rac | —CN | 0.34/D | Aldrich | XXXII/XXXIII |
| 100 | rac | rac | —CF$_3$ | 0.22/T | J. R. McCarthy et al., Tetrahedron Lett. 31, 5547 (1990). | XXXII/XXXIII |
| 101 | rac | rac | —CONH~~~N(CH$_3$)$_2$ | 0.49/B | Example 93 | Example 75* |

*The reaction solvent is ethanol.

Example 102

(2S)-2-[4-(Quinolin-2-yl-methoxy)-phenyl]-2-cycloheptyl-acetic acid N-(1-phenylvinyl)amide

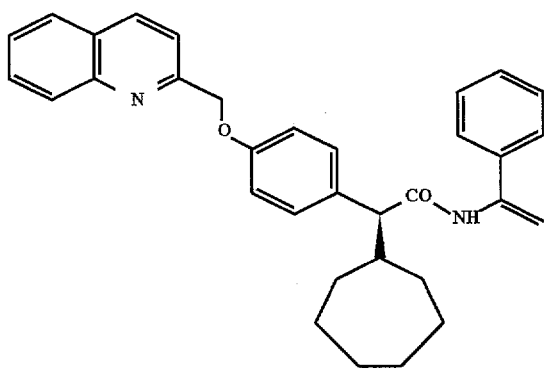

2.0 g of the compound from Example XXXIV are reacted with 0.545 ml of triethylamine and 0.304 ml of mesyl chloride in 20 ml of anhydrous DMF at −30° C. After 2 hours, a further 1.09 ml of triethylamine are added and the mixture is warmed to room temperature. After the mixture has been subsequently stirred for 20 hours, it is brought to pH 2 with 2M hydrochloric acid and extracted with an ether/ethyl acetate mixture. The organic phases are dried with magnesium sulphate and evaporated. The crude material obtained is purified by column chromatography (silica gel 60, Merck 40–63 μm, petroleum ether:ethyl acetate first 5:1 then 2:1).

Yield: 1.3 g $R_f$=0.20 (T) characteristic $^1$H-NMR signals (CDCl$_3$, 200 MHz, TMS): δ=4.55 (dd, 1H); 5.16 (dd, 1H) (vinyl protons) ppm.

The compounds of the following Table 10 are prepared analogously to the instructions for Example 102:

TABLE 10

| Example No. | 1 | R² | R$_f$/solvent |
|---|---|---|---|
| 103 | S | cyclopentyl | 0.84/O |
| 104 | rac | CH(Me)(Me) (isobutyl) | 0.90/B |
| 105 | rac | —CH$_3$ | 0.70/A |
| 106 | rac | CH$_2$-cyclohexyl | 0.97/B |
| 107 | rac | CH$_2$-(4-fluorocyclohexyl) | 0.98/B |

TABLE 11

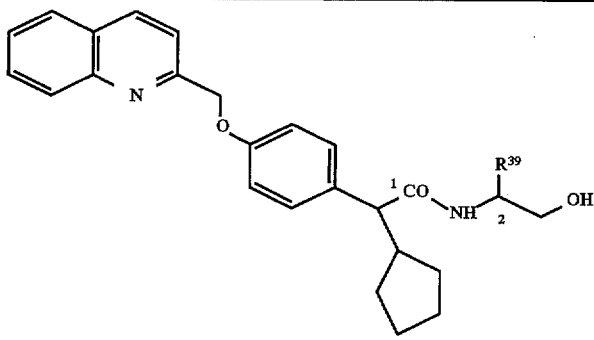

| Ex. No. 1 | 2 | R³⁹ | Rf/solvent/ melting point | Example No./ Distributor of the precursor amines | Preparation analogously to Ex. No. |
|---|---|---|---|---|---|
| 108 | S | / | H | m.p. = 143° C. | Aldrich | XXXII/XXXIII |
| 109 | S | R | Et | m.p. = 167–170° C. (toluene) | Aldrich | XXXII/XXXIII |
| 110 | S | R | iBu | m.p. = 155° C. (toluene) | Aldrich | XXXII/XXXIII |
| 111 | S | / | CH₂OH | 0.20 (W) | Aldrich | XXXII/XXXIII |
| 112 | S | S | CO₂Me | m.p. = 173–175° C. | Aldrich | XXXII/XXXIII |
| 113 | S | S | COOH | m.p. = 183–185° C. | Example 112 | Example 74 |

*Note: columns for Ex. No. 1, 2, R³⁹ shown; row 108 has R³⁹ = H.*

TABLE 12

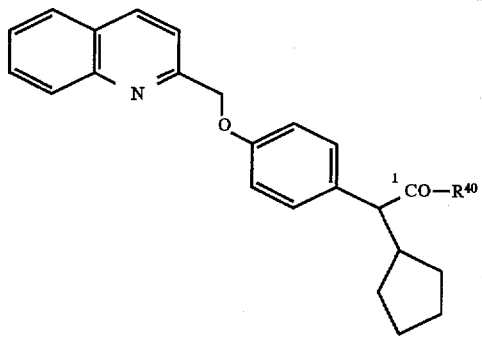

| Ex. No. 1 | R⁴⁰ | Rf/solvent | Example No./literature/ distributor of the precursor amines |
|---|---|---|---|
| 114 | rac, (R)-NH-CH(CH₂Ph)-CH₂OH | 0.26/C | Aldrich |
| 115 | S, (S)-NH-CH(CH₂Ph)-CH₂OH | m.p. = 158° C. (ethanol) | Aldrich |
| 116 | R, (S)-NH-CH(CH₂Ph)-CH₂OH | m.p. = 132° C. (toluene/ ethyl acetate) | Aldrich |

TABLE 12-continued
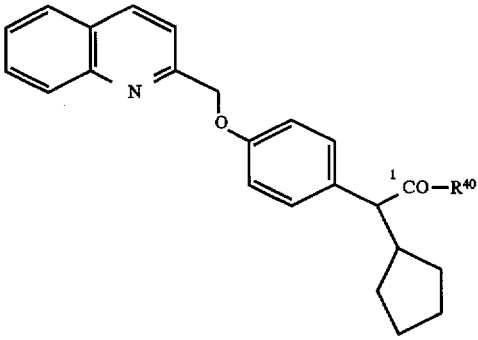
| Ex. No. 1 | R⁴⁰ | | $R_f$/solvent | Example No./literature/distributor of the precursor amines |
|---|---|---|---|---|
| 117 | rac | (structure) | 0.73/B | DE 26 28 469 |
| 118 | rac | (structure) | 0.77/B | DE 26 28 469 |
| 119 | rac | (structure) | 0.51/C | DE 26 28 469 |
| 120 | rac | (structure) | 0.21/D | H.V. Sccor et al., J. Org. Chem. 43, 2539 (1978). |
| 121 | rac | (structure) | 0.13/D | Khim. Farm. Zh. 25, 60 (1991) |
| 122 | rac | (structure) | 0.94/B | Example XXXI |

TABLE 12-continued
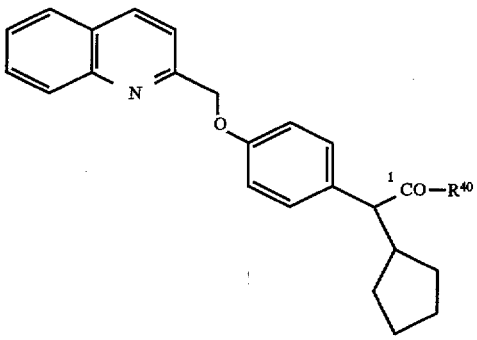
| Ex. No. 1 | R⁴⁰ | | $R_f$/solvent | Example No./literature/ distributor of the precursor amines |
|---|---|---|---|---|
| 123 | rac | 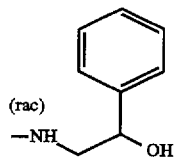 (rac) | 0.76/B | Sigma |
| 124 | rac | 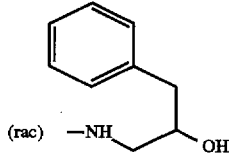 (rac) | 0.15/D | WO 91/18 897 |
| 125 | rac | 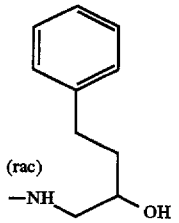 (rac) | 0.19/C | DE 36 43 012 |

TABLE 13

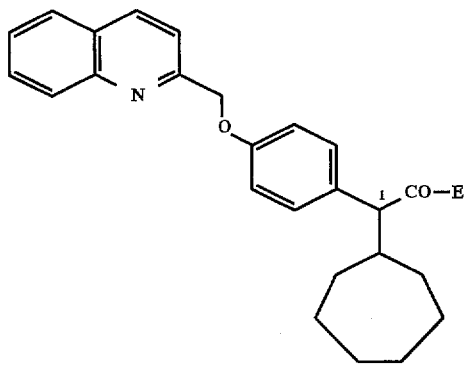

| Ex. No. | 1 | E | $R_f$/solvent | Literature/distributor of the precursor amines |
|---|---|---|---|---|
| 126 | S | —NH—CH$_2$—C$_6$H$_5$ | 0.51/D | Aldrich |
| 127 | S | —N(C$_6$H$_5$)CH$_2$CH$_2$OH | 0.80/V | Aldrich |

TABLE 13-continued

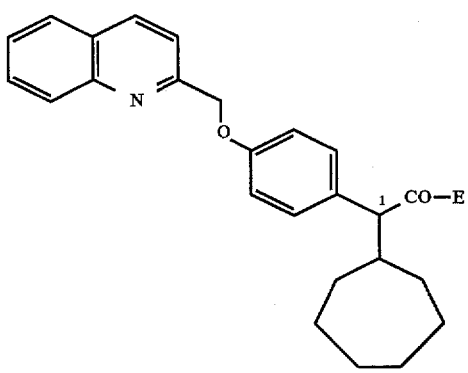

| Ex. No. | 1 | E | $R_f$/solvent | Literature/distributor of the precursor amines |
|---|---|---|---|---|
| 128 | S | indanyl-NH-OH | 0.13/D | P & B |
| 129 | S | (rac) -NH-C(CH$_3$)(C$_6$H$_5$)CH$_2$OH | 0.51/O | EP 514 267 |

TABLE 14

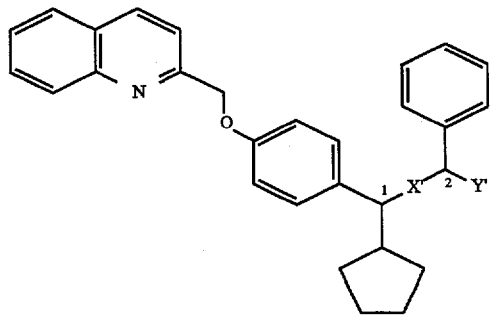

| Ex. No. | 1 | 2 | X' | Y' | $R_f$/solvent | Literature of the starting compounds |
|---|---|---|---|---|---|---|
| 130 | rac | rac | CON(CH$_3$) | CH$_2$OH | 0.89/B | GB 14 34 826. |
| 131 | rac | rac | CONH | CH$_2$OCH$_3$ | 0.17/G | A. I. Meyers et al., J. Org. Chem. 43, 892 (1978). |
| 132 | rac | rac | CON(CH$_3$) | CH$_2$OCH$_3$ | 0.19/G | B. E. Rossiter et al., Tetrahedron 49, 965 (1993). |
| 133 | rac | rac | COO | CH(OC$_2$H$_5$)$_2$ | 0.68/D | P. Tinapp, Arch. Pharm. 310, 89 (1977). |
| 134 | rac | dia A | CO—S— | CH$_2$OH | 0.42/H | Y. Gareau et al., Tetrahedron Lett. 34, 3363 (1993). |
| 135 | rac | dia B | CO—S— | CH$_2$OH | 0.39/H | Y. Gareau et al., Tetrahedron Lett. 34, 3363 (1993). |

Example 136

(α-Formyl)benzyl 2-[4-(quinolin-2-yl-methoxy)-phenyl]-2-cyclopentyl-acetate

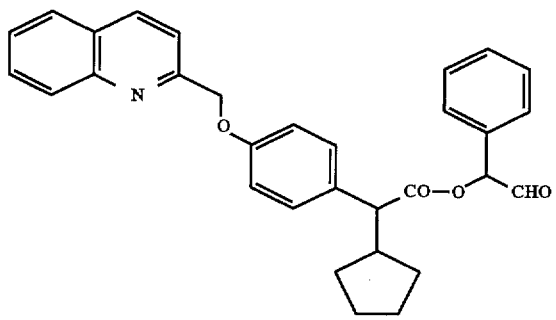

3.5 g of the compound from Example 133 are dissolved in 60 ml of dioxane and reacted with 20 ml of concentrated hydrochloric acid at room temperature for 4 hours. The mixture is then extracted with a mixture of ether and aqueous sodium carbonate solution. The organic phase is washed with water, dried with magnesium sulphate and evaporated. The crude product is purified by column chromatography (silica gel 60, Merck, 40–63 µm, petroleum ether:ethyl acetate=first 4:1, then 2:1, finally 1:1).

Yield: 1.7 g $R_f$=0.10 (V)

Example 137

(α-Hydroxymethyl)benzyl 2-[4-(quinolin-2-yl-methoxy)phenyl]-2-cyclopentyl-acetate

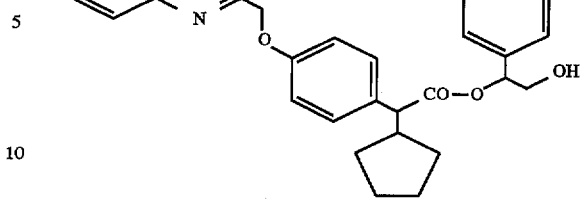

0.46 g of the compound from Example 136 is reacted with 40 mg of sodium boronate in 20 ml of ethanol at room temperature. After 30 minutes, the mixture is poured onto water and extracted with ethyl acetate. The organic phases are dried with magnesium sulphate and freed from the solvent in vacuo. The resulting crude product is purified by column chromatography (silica gel 60, Merck, 40–63 µm, petroleum ether:ethyl acetate=7:1, later 3:1).

Yield: 0.12 g $R_f$=0.41 (H)

Example 138

(α-Acetoxymethyl)-thiobenzyl 2-[4-(quinolin-2-yl-methoxy)phenyl]-2-cyclopentyl-acetate

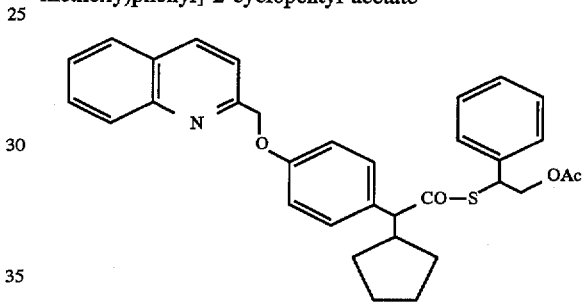

The compound (diastereomer mixture) from Example 134 and 135 can be converted into the title compound analogously to the instructions for Example 89.

$R_f$=0.28 (T)

TABLE 15

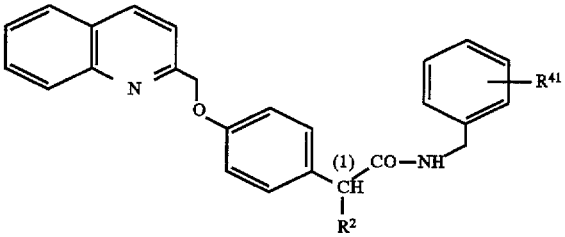

| Example No. | absolute con-figuration (1) | $R^2$ | $R^{41}$ | $R_f$(solvent)/melting point | Distributor of the benzylamines |
|---|---|---|---|---|---|
| 139 | S | cyclopentyl | H | m.p. = 138° C. | Aldrich |
| 140 | R | cyclopentyl | H | m.p. = 134° C. | Aldrich |

TABLE 15-continued

| Example No. | absolute configuration (1) | R² | R⁴¹ | R_f(solvent)/ melting point | Distributor of the benzylamines |
|---|---|---|---|---|---|
| 141 | S | cycloheptyl | H | 0.41 (D) | Aldrich |
| 142 | R | cycloheptyl | H | 0.41 (D) | Aldrich |
| 143 | S | cycloheptyl | 2-Cl | 0.31 (Y) | Aldrich |
| 144 | S | cycloheptyl | 3-Cl | 0.26 (Y) | Maybridge |
| 145 | S | cycloheptyl | 4-Cl | 0.30 (Y) | Aldrich |
| 146 | S | cycloheptyl | 4-F | 0.32 (Y) | Aldrich |

Example 147

(2R)-[4-(quinolin-2-yl-methoxy)-phenyl]-2-cyclopentyl-acetic acid (S)-(O-acetyl)phenyl-glycinol-amide

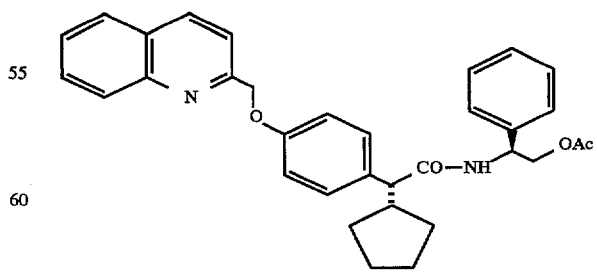

(2R)-2-[4-(quinolin-2-yl-methoxy)phenyl]-2-cyclopentyl-acetic acid (S)-phenylglycinolamide [U.S. Pat. No. 4,970,215] is reacted analogously to the instructions of Example 1 to give the title compound.

$R_f$=0.47 (ethanol:methylene chloride=1:20)

m.p.=173° C.

TABLE 16

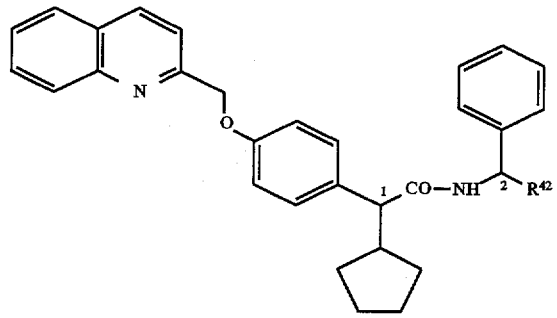

| Example No. | 1 | 2 | $R^{42}$ | Melting point [°C.] | Starting material (amine) a) Literature b) Distributing company |
|---|---|---|---|---|---|
| 148 | R | S | Me | m.p. = 157° C. | b) Aldrich |
| 149 | R | S | CH$_2$OMe | m.p. = 147° C. | a) A. I. Meyers et al., J. Org. Chem. 43, 892 (1978). |
| 150 | S | S | CH$_2$OMe | m.p. = 146° C. | a) A. I. Meyers et al., J. Org. Chem. 43, 892 (1978). |
| 151 | R | R | Me | m.p. = 145° C. | b) Aldrich |
| 152 | S | R | Me | m.p. = 163° C. | b) Aldrich |

TABLE 17

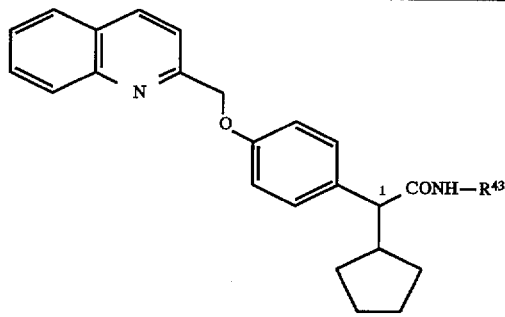

| Example No. | 1 | $R^{43}$ | $R_f$ value (solvent) Melting point [°C.] | Starting material a) Literature b) Distributing company* c) Preparation analogously to Ex. No. |
|---|---|---|---|---|
| 153 | R | Et | m.p. = 142° C. | b) Aldrich |
| 154 | S | Et | m.p. = 145° C. | b) Aldrich |
| 155 | R | CH$_2$CH$_2$OH | m.p. = 143° C. | a) Aldrich |
| 156 | rac | CH$_2$CH$_2$OH | m.p. = 130° C. | b) Aldrich |
| 157 | rac | CH$_2$COOH | m.p. = 182–185° C. | c) analogously to Ex. No. 74 (from Ex. No. 158) |
| 158 | rac | CH$_2$CO$_2$Me | m.p. = 134–136° C. | b) Aldrich |
| 159 | S | 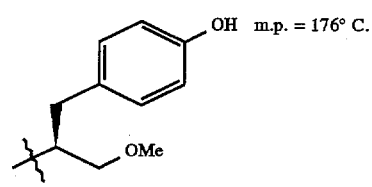 | m.p. = 176° C. | |

TABLE 17-continued
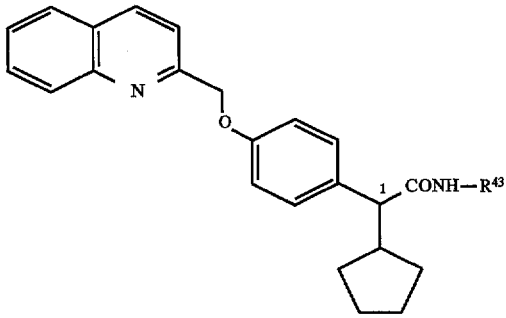
| Example No. 1 | ⫞—R43 | $R_f$ value (solvent) Melting point [°C.] | Starting material a) Literature b) Distributing company* c) Preparation analogously to Ex. No. |
|---|---|---|---|
| 160 | R 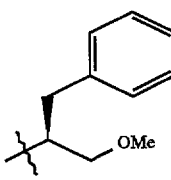 | m.p. = 123° C. | |
| 161 | S 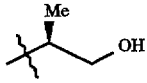 | m.p. = 134° C. | b) Aldrich |
| 162 | R 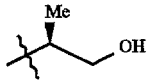 | m.p. = 184° C. | b) Aldrich |
| 163 | R 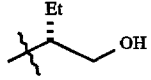 | m.p. = 168° C. | b) Aldrich |
| 164 | R 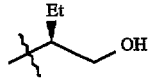 | m.p. = 170° C. | b) Aldrich |
| 165 | S 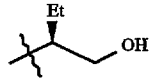 | m.p. = 142° C. | b) Aldrich |
| 166 | R 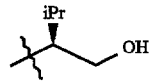 | m.p. = 158° C. | b) Sigma |
| 167 | S 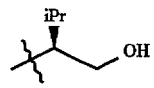 | m.p. = 186° C. | b) Sigma |
| 168 | S 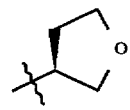 | m.p. = 160° C. | b) D-Schuchardt |
| 169 | R 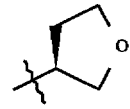 | m.p. = 137° C. | b) D-Schuchardt |

TABLE 17-continued
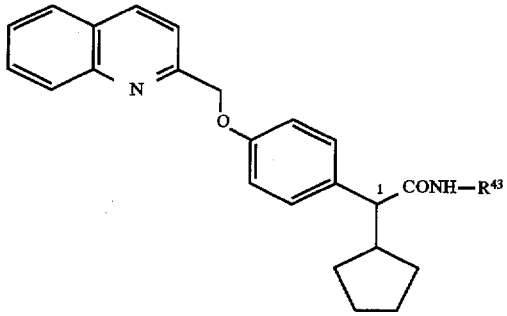
| Example No. | 1 | ⊦R⁴³ | R_f value (solvent) Melting point [°C.] | Starting material a) Literature b) Distributing company* c) Preparation analogously to Ex. No. |
|---|---|---|---|---|
| 170 | S | 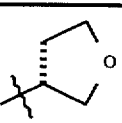 | m.p. = 139° C. | b) D-Schuchardt |
| 171 | R | 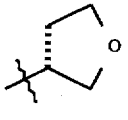 | m.p. = 160° C. | b) D-Schuchardt |
| 172 | S | 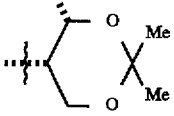 | R_f = 0.48 (AA) | b) Sigma |
| 173 | R | 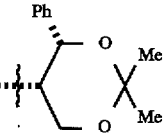 | R_f = 0.43 (AA) | b) Sigma |
| 174 | R | 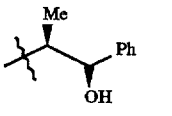 | m.p. = 233° C. | b) Sigma |
| 175 | S | 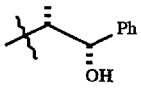 | m.p. = 234° C. | b) Sigma |
| 176 | R | 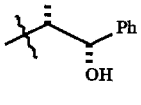 | m.p. = 219° C. | b) Sigma |
| 177 | S | 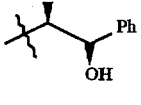 | m.p. = 214° C. | b) Sigma |
| 178 | R | 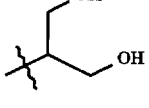 | R_f = 0.12 (W) m.p. = 161° C. | b) Aldrich |

TABLE 17-continued

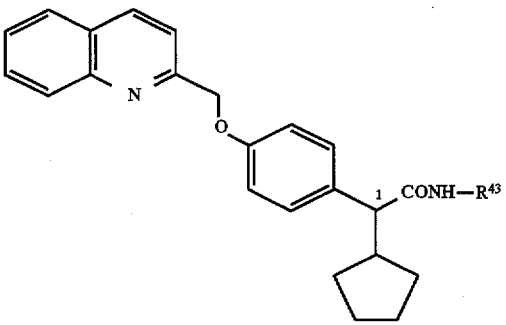

| Example No. | 1 | ⟩―R⁴³ | R_f value (solvent) Melting point [°C.] | Starting material a) Literature b) Distributing company* c) Preparation analogously to Ex. No. |
|---|---|---|---|---|
| 179 | S | iBu  OH | m.p. = 152° C. | n) Aldrich |
| 180 | R | iBu 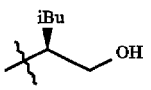 OH | m.p. = 154° C. | b) Aldrich |
| 181 | R | iBu 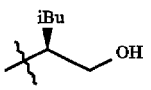 OH | m.p. = 155° C. | b) Aldrich |
| 182 | S | Me, Et 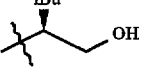 OH | m.p. = 164° C. | b) Aldrich |
| 183 | R | Me, Et 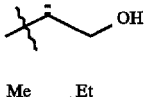 OH | m.p. = 134° C. | b) Aldrich |
| 184 | R | 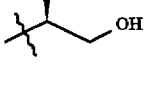 (L)- OH, OH | m.p. = 200° C. | b) Sigma |
| 185 | S | 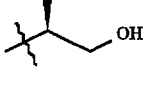 (L)- OH, OH | m.p. = 190° C. | b) Sigma |
| 186 | R | 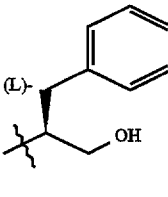 Ph OH | m.p. = 168° C. | b) Aldrich |
| 187 | R | Ph Ph 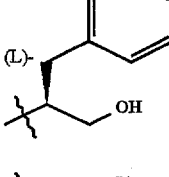 OH | $R_f$ = 0.37 (AF) | a) G. Bittner et al., Justus Liebigs Ann. Chem. 713, 1 (1968) |

TABLE 17-continued

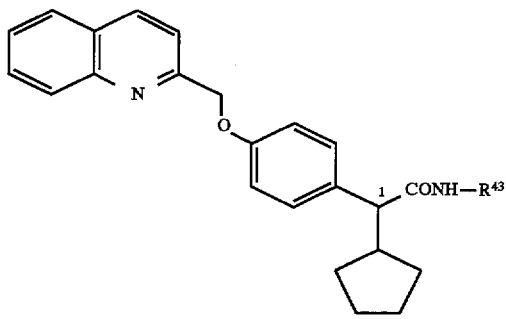

| Example No. | 1 | ⊣R⁴³ | $R_f$ value (solvent) Melting point [°C.] | Starting material a) Literature b) Distributing company* c) Preparation analogously to Ex. No. |
|---|---|---|---|---|
| 188 | R | 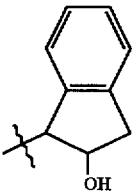 | $R_f$ = 0.18 (X) | b) P & B |
| 189 | S | 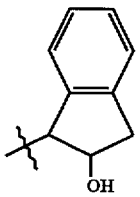 | $R_f$ = 0.45 (X) | b) P & B |
| 190 | R | 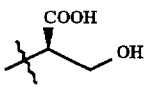 | $R_f$ = 0.01 (AH) | c) analogously to Ex. No. 74 (from Ex. No. 193) |
| 191 | S | 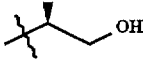 | $R_f$ = 0.02 (AH) | c) analogously to Ex. No. 74 (from Ex. No. 192) |
| 192 | S | 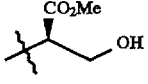 | $R_f$ = 0.14 (AH) | b) Chemalog |
| 193 | R | 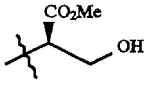 | $R_f$ = 0.21 (AH) | b) Chemalog |
| 194 | R | 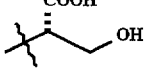 | $R_f$ = 0.01 (AE) | c) analogously to Ex. No. 74 (from Ex. No. 195) |
| 195 | R | 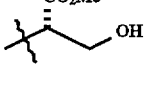 | $R_f$ = 0.21 (AH) | b) Chemalog |
| 196 | R | 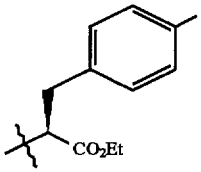 | $R_f$ = 0.38 (D) | b) Fluka |

TABLE 17-continued

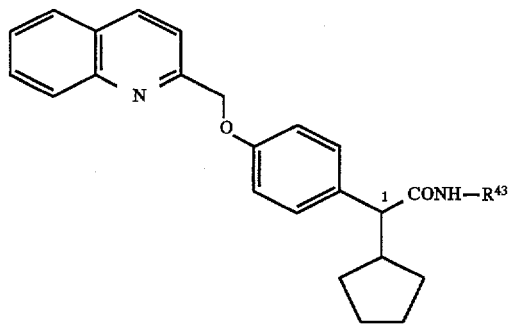

| Example No. 1 | ⊰R⁴³ | R<sub>f</sub>-value (solvent) Melting point [°C.] | Starting material a) Literature b) Distributing company* c) Preparation analogously to Ex. No. |
|---|---|---|---|
| 197 | S, ⊰CH(CH₂Ph)CO₂Me | R<sub>f</sub> = 0.50 (X) | b) Sigma |
| 198 | S, ⊰CH(CH₂Ph)COOH | R<sub>f</sub> = 0.02 (X) | c) analogously to Ex. No. 74 |
| 199 | R, ⊰CH(CH₂Ph)COOH | R<sub>f</sub> = 0.02 (X) | c) analogously to Ex. No. 74 |
| 200 | S, ⊰CH(CH₂-C₆H₄-OH)COOH | R<sub>f</sub> = 0.01 (X) | c) analogously to Ex. No. 74 |
| 201 | R, ⊰CH(CH₂-C₆H₄-OH)COOH | R<sub>f</sub> = 0.01 (X) | c) analogously to Ex. No. 74 |
| 202 | R, ⊰CH(CH₂Ph)CO₂Me | R<sub>f</sub> = 0.50 (X) | b) Sigma |

*The company stated relates to the precursor amine; the preparation proceeds analogously to the instructions for Examples XXXII and XXXIII.

TABLE 18

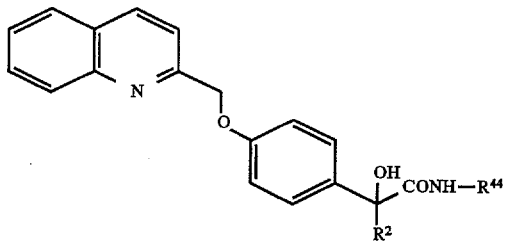

| Example No. 1 | R² | ⫫—R⁴⁴ | R_f value (solvent) Melting Point [°C.] | Starting material a) Literature b) Distributing company c) Preparation analogously to Ex. No. |
|---|---|---|---|---|
| 203 | rac | cHept —Me | m.p. = 163–166° C. | b) Aldrich |
| 204 | rac | cHept 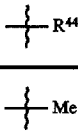 | R_f = 0.13 (AC) | b) Lancaster |
| 205 | rac | cHept 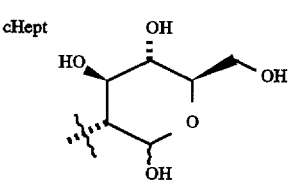 | R_f = 0.46 (AE) | b) Sigma |
| 206 | rac | cHept 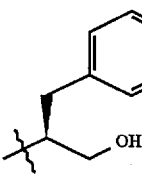 | R_f = 0.37 (AE) | b) Aldrich |
| 207 | rac | cHept 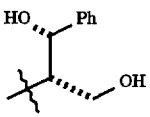 | R_f = 0.85 (AD) | a) G. Bittner et al., Justus Liebigs Ann. Chem. 713, 1 (1968). |
| 208 | rac | cHept 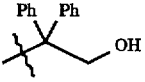 | R_f = 0.57 (AE) | b) Aldrich |
| 209 | rac | cHept 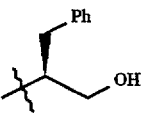 | R_f = 0.03 (AC) | b) Aldrich |
| 210 | rac | cHept 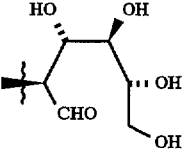 | R_f = 0.61 (AG) | b) Columbia |
| 211 | rac | cHept 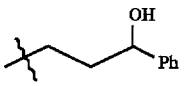 | R_f = 0.28 (H) | a) DE 2 552 196 |

TABLE 18-continued

[Structure: quinoline-CH2-O-phenyl-C(OH)(R2)-CONH-R44]

| Example No. 1 | R² | ⧸R⁴⁴ | R_f value (solvent) Melting Point [°C.] | Starting material a) Literature b) Distributing company c) Preparation analogously to Ex. No. |
|---|---|---|---|---|
| 212 | rac | cHept | R_f = 0.62 (O) | a) GB 1 129 029 |

[Structure: fluorenyl with HO and CH2CH2- attachment]

| 213 | rac | cHept | R_f = 0.64 (AF) | c) Example No. XL |

[Structure: 4-(SO2Me)-phenyl-CH(CO2Me)-]

TABLE 19

[Structure: quinoline-CH2-O-phenyl-CH(cycloheptyl)-CONH-R45]

| Example No. | 1 | R⁴⁵ | R_f value (solvent) Melting point [°C.] | Starting material a) Literature b) Distributing company c) Preparation analogously to Ex. No. |
|---|---|---|---|---|
| 214 | rac | CH₂CH₂OH | m.p. = 91–94° C. | b) Aldrich |
| 215 | R | -CH(Ph)(OH)- (CH2CH(OH)Ph) | R_f = 0.44 (O) | b) Aldrich |
| 216 | R | -CH(Ph)(COOH) | R_f = 0.11 (E) | a) Analogously to Example 74 |

TABLE 20

| Ex. No. | 1 | R² | ―R⁴⁶ | Melting point [°C.] | Starting material<br>a) Literature<br>b) Distributing company<br>c) Preparation analogously to Ex. No. |
|---|---|---|---|---|---|
| 217 | rac | nBu | 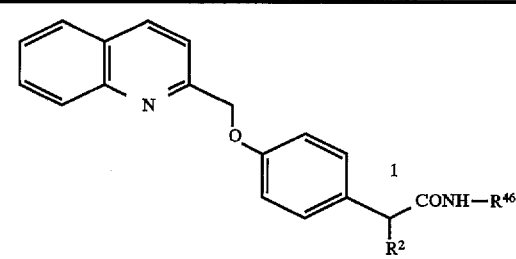 | m.p. = 174° C. | b) Aldrich |
| 218 | rac | nBu | 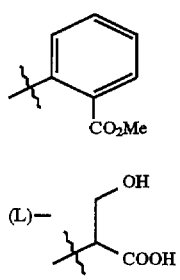 | m.p. = 165–170° C. | c) analogously to Example No. 74 (from Example No. 219) |
| 219 | rac | nBu | 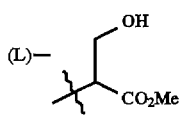 | m.p. = 157–159° C. | b) Aldrich |
| 220 | rac | nBu | CH₂COOH | m.p. = 173–175° C. | c) analogously to Example No. 74 (from Example No. 222) |
| 221 | rac | nBu | 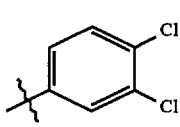 | m.p. = 187° C. | b) Aldrich |
| 222 | rac | nBu | CH₂CO₂Me | m.p. = 177° C. | b) Aldrich |
| 223 | — | H | 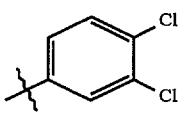 | m.p. = 193° C. | b) Aldrich |
| 224 | — | H | 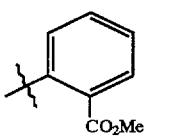 | m.p. = 187° C. | b) Aldrich |

TABLE 21

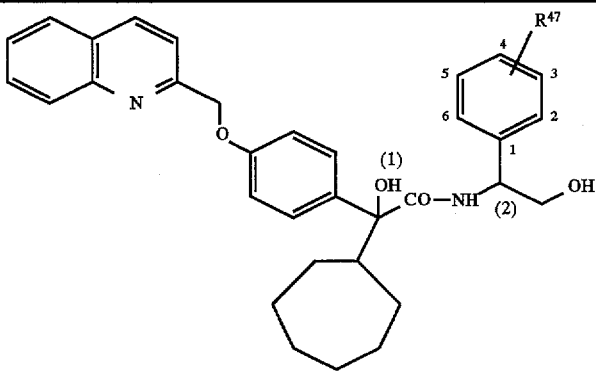

| Ex. No. | (1) | (2) | $R^{47}$ | $R_f$ value (solvent) | Starting material<br>a) Literature<br>b) Distributing company<br>c) Preparation analogously to Ex. No. |
|---|---|---|---|---|---|
| 225 | rac | rac | 4-Cl | $R_f$ = 0.52 (AD) | c) analogously to Example No. XXXII and XXXIII (from Example No. XX) |
| 226 | rac | rac | 3-Cl | $R_f$ = 0.69 (AE) | c) analogously to Example No. XXXII and XXXIII (from Example No. XIX) |
| 227 | rac | rac | 4-Me | $R_f$ = 0.67 (AE) | c) analogously to Example No. XXXII and XXXIII (from Example No. XXVII) |
| 228 | rac | rac | 2-OH | $R_f$ = 0.32 (O) | c) analogously to Example No. XXXII and XXXIII (from Example No. XXXV) |
| 229 | rac | rac | 3-OH | $R_f$ = 0.40 (B) | c) analogously to Example No. XXXII and XXXIII (from Example No. XXXVI) |
| 230 | rac | rac | 3-OSO$_2$Me | $R_f$ = 0.49 (B) | c) analogously to Example No. 90 (from Example No. 229) |
| 231 | rac | dia B | 4-OH | $R_f$ = 0.51 (C) | c) analogously to Example No. XXXII and XXXIII (from Example No. XXXVII) |
| 232 | rac | dia A | 4-OH | $R_f$ = 0.60 (C) | c) analogously to Example No. XXXII and XXXIII (from Example No. XXXVII) |
| 233 | dia A | R | H | $R_f$ = 0.43 (C) | b) Aldrich |
| 234 | dia B | R | H | $R_f$ = 0.42 (C) | b) Aldrich |

TABLE 22

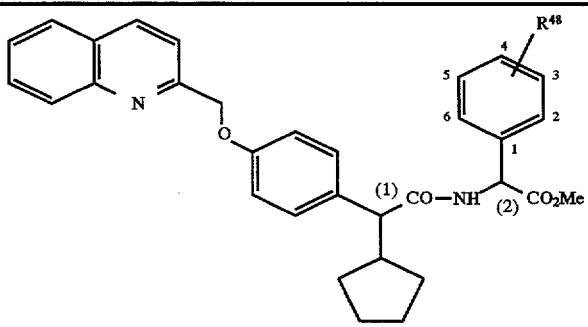

| Ex. No. | (1) | (2) | $R^{48}$ | $R_f$ value (solvent) | Starting material<br>a) Literature<br>b) Distributing company<br>c) Preparation from Example. No. |
|---|---|---|---|---|---|
| 235 | R | dia A | 4-cPr | $R_f$ = 0.24 (V) | c) III |
| 236 | R | dia B | 4-cPr | $R_f$ = 0.21 (V) | c) III |
| 237 | R | dia A | 4-tBu | $R_f$ = 0.25 (V) | a) WO 91 08 704 |
| 238 | R | dia B | 4-tBu | $R_f$ = 0.22 (V) | a) WO 91 08 704 |
| 239 | R | rac | 4-Ph | $R_f$ = 0.50 (X) | c) IV |
| 240 | R | R | 4-Cl | $R_f$ = 0.43 (AF) | c) XXXVIII |
| 241 | R | S | 4-Cl | $R_f$ = 0.47 (X) | c) XXXVIII |
| 242 | R | dia A | 2-OH | $R_f$ = 0.36 (X) | c) II |
| 243 | R | dia B | 2-OH | $R_f$ = 0.28 (X) | c) II |
| 244 | R | rac | 3-OH | $R_f$ = 0.35 (X) | a) DE 22 04 117 |
| 245 | R | rac | 4-OH | $R_f$ = 0.23 (AF) | a) EP 530 879 |
| 246 | R | rac | 4-Me | $R_f$ = 0.53 (X) | a) F. Rose — Munch et al., |

TABLE 22-continued

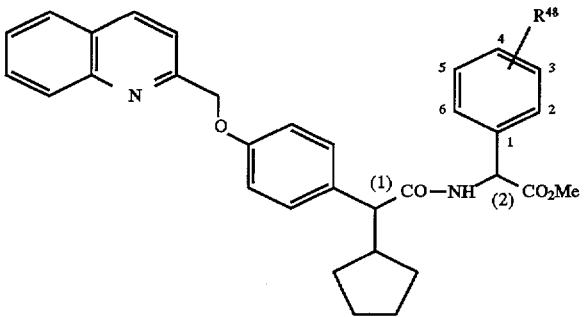

| Ex. No. | (1) | (2) | R⁴⁸ | $R_f$ value (solvent) | Starting material<br>a) Literature<br>b) Distributing company<br>c) Preparation from Example. No. |
|---|---|---|---|---|---|
| | | | | | J. Organomet. Chem. 415, 223 (1991). |
| 247 | R | rac | 4-SO₂Me | $R_f$ = 0.56 (AH) | c) XL |
| 248 | R | R | 4-OH | $R_f$ = 0.51 (AH) | a) EP 530 879 |
| 249 | R | rac | 4-N(morpholino) | $R_f$ = 0.23 (O) | c) VI |
| 250 | R | rac | 4-N(pyrrolidino) | $R_f$ = 0.22 (AF) | c) XXXIX |
| 251 | R | dia A | 3-CF₃ | $R_f$ = 0.25 (AF) | c) XLI |
| 252 | R | dia B | 3-CF₃ | $R_f$ = 0.21 (AF) | c) XLI |
| 253 | R | dia A | 4-F, 3-OPh | $R_f$ = 0.26 (AF) | c) XLII |
| 254 | R | dia B | 4-F, 3-OPh | $R_f$ = 0.23 (AF) | c) XLII |
| 255 | R | S | H | $R_f$ = 0.55 (X) | b) Aldrich |
| 256 | S | S | H | $R_f$ = 0.53 (X) | b) Aldrich |
| 257 | R | dia A | 4-OCF₃ | $R_f$ = 0.33 (Af) | c) XLIII |
| 258 | R | dia B | 4-OCF₃ | $R_f$ = 0.28 (AF) | c) XLIII |
| 259 | R | R | H | $R_f$ = 0.50 (X) | b) Aldrich |
| 260 | R | rac | 3,4-(OH)₂ | $R_f$ = 0.29 (A) | c) XLIV |

TABLE 23

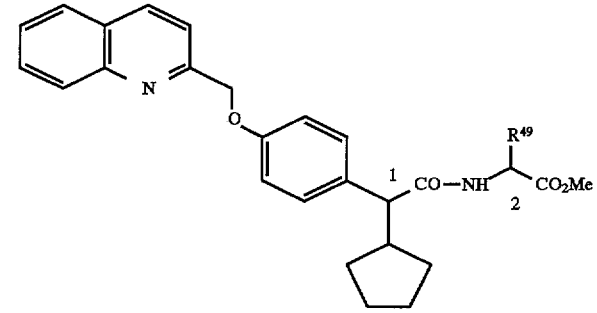

| Example No. | 1 | 2 | R⁴⁹ | $R_f$ value (solvent) | Starting material<br>a) Literature<br>b) Distributing company<br>c) Preparation from Example No. |
|---|---|---|---|---|---|
| 261 | R | rac | pyridyl | $R_f$ = 0.31 (AE) | c) IX |

TABLE 23-continued
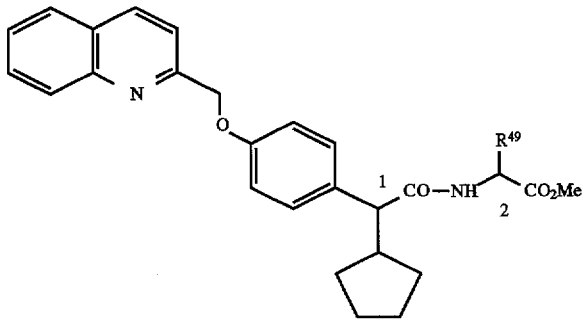
| Example No. | 1 | 2 | R49 | $R_f$ value (solvent) | Starting material<br>a) Literature<br>b) Distributing company<br>c) Preparation from Example No. |
|---|---|---|---|---|---|
| 262 | R | rac | 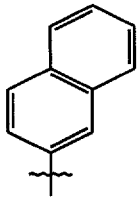 | $R_f$ = 0.66 (X) | c) V |
| 263 | R | rac | 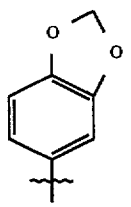 | $R_f$ = 0.43 (X) | a) G. H. Hakimelahi and G. Just, Can. J. Chem. 57, 1932 (1979). |
| 264 | S | rac | 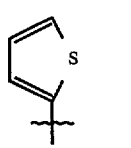 | $R_f$ = 0.38 (X) | a) DE 22 04 117 |
| 265 | R | rac | 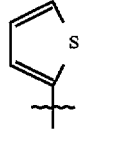 | $R_f$ = 0.26 (AF) | a) DE 22 04 117 |
| 266 | S | S | 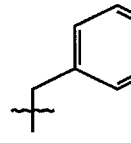 | $R_f$ = 0.34 (D) | b) Aldrich |

TABLE 24

Structure: Quinoline-2-CH$_2$-O-(4-phenyl)-CH(cyclopentyl)-CO(1)-NH(2)-CH(Ar)-CH$_2$OH, where Ar is a phenyl bearing R$^{50}$ (positions 1-6 as labeled).

Starting material
a) Literature
b) Distributing company
c) Preparation analogously to Example.

| Ex. No. | (1) | (2) | R$^{50}$ | R$_f$ value (solvent) | | No. |
|---|---|---|---|---|---|---|
| 267 | R | R | 4-Cl | R$_f$ = 0.35 (O) | c) | analogously to Example No. 21 (from Example No. 240) |
| 268 | R | rac | 4-Ph | R$_f$ = 0.22 (O) | c) | analogously to Example No. 21 (from Example No. 239) |
| 269 | R | S | 4-Cl | R$_f$ = 0.33 (O) | c) | analogously to Example No. 21 (from Example No. 241) |
| 270 | R | dia B | 2-OH | R$_f$ = 0.28 (AH) | c) | analogously to Example No. 21 (from Example No. 243) |
| 271 | R | dia A | 2-OH | R$_f$ = 0.29 (AH) | c) | analogously to Example No. 21 (from Example No. 242) |
| 272 | R | dia B | 4-cPr | R$_f$ = 0.26 (O) | c) | analogously to Example No. 21 (from Example No. 236) |
| 273 | R | dia A | 4-cPr | R$_f$ = 0.26 (O) | c) | analogously to Example No. 21 (from Example No. 235) |
| 274 | R | rac | 4-OH | R$_f$ = 0.24 (AE) | c) | analogously to Example No. 21 (from Example No. 245) |
| 275 | R | dia A | 4-tBu | R$_f$ = 0.35 (O) | c) | analogously to Example No. 21 (from Example No. 237) |
| 276 | R | dia B | 4-tBu | R$_f$ = 0.32 (O) | c) | analogously to Example No. 21 (from Example No. 238) |
| 277 | R | R | 4-OH | R$_f$ = 0.46 (AI) | c) | analogously to Example No. 21 (from Example No. 248) |
| 278 | R | rac | 4-SO$_2$Me | R$_f$ = 0.31 (AI) | c) | analogously to Example No. 21 (from Example No. 247) |
| 279 | R | rac | 4-N(pyrrolidinyl) | R$_f$ = 0.33 (O) | c) | analogously to Example No. 21 (from Example No. 250) |
| 280 | S | Dia B | 2-OH | R$_f$ = 0.50 (AH) | c) | analogously to Example No. XXXII and XXXIII (from Example No. XXXV) |
| 281 | S | S | 4-Cl | R$_f$ = 0.21 (O) | c) | analogously to Example No. XXXII and XXXIII |
| 282 | S | dia A | 2-OH | R$_f$ = 0.37 (AH) | c) | analogously to Example No. XXXII and XXXIII (from Example No. XXXV) |
| 283 | R | dia A | 2-OH, 3-I | R$_f$ = 0.30 (O) | c) | analogously to Example No. XXXII and XXXIII |
| 284 | R | dia B | 2-OH, 3-I | R$_f$ = 0.29 (O) | c) | analogously to Example No. XXXII and XXXIII |
| 285 | S | R | 4-Cl | R$_f$ = 0.23 (O) | c) | analogously to Example No. XXXII and XXXIII |
| 286 | S | rac | 4-F | R$_f$ = 0.34 (O) | c) | analogously to Example No. XXXII and XXXIII (from Example No. XVIII) |
| 287 | S | rac | 3-OH | R$_f$ = 0.25 (AH) | c) | analogously to Example No. XXXII and XXXIII (from Example No. XXXVI) |
| 288 | S | rac | 2-F | R$_f$ = 0.37 (O) | c) | analogously to Example No. XXXII and XXXIII (from Example No. XVII) |
| 289 | R | rac | 2-F | R$_f$ = 0.39 (O) | c) | analogously to Example No. XXXII and XXXIII (from Example No. XVII) |

TABLE 24-continued

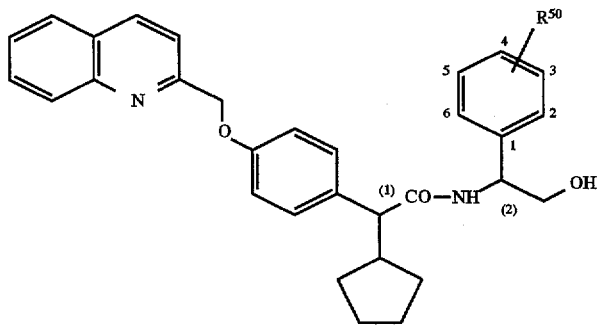

Starting material
a) Literature
b) Distributing company
c) Preparation analogously to Example.

| Ex. No. | (1) | (2) | $R^{50}$ | $R_f$ value (solvent) | No. | |
|---|---|---|---|---|---|---|
| 290 | R | rac | ![morpholine] +N⟨O⟩ | $R_f = 0.13$ (AE) | c) | analogously to Example No. 21 (from Example No. 249) |
| 291 | R | dia B | 3-CF$_3$ | $R_f = 0.39$ (O) | c) | analogously to Example No. 21 (from Example 251) |
| 292 | R | dia A | 3-CF$_3$ | $R_f = 0.28$ (O) | c) | analogously to Example No. 21 (from Example No. 251) |
| 293 | R | dia A | 4-OCF$_3$ | $R_f = 0.13$ (X) | c) | analogously to Example No. 21 (from Example No. 257) |
| 294 | R | dia B | 4-OCF$_3$ | $R_f = 0.29$ (O) | c) | analogously to Example No. 21 (from Example No. 258) |
| 295 | R | dia B | 4-F, 2-OPh | $R_f = 0.13$ (O) | c) | analogously to Example No. 21 (from Example No. 254) |
| 296 | R | dia A | 4-F, 3-OPh | $R_f = 0.22$ (O) | c) | analogously to Example No. 21 (from Example No. 253) |
| 297 | R | rac | 3-OH | $R_f = 0.26$ (AE) | c) | analogously to Example No. XXXII and XXXIII (from Example No. XXXVI) |
| 298 | R | rac | 4-Me | $R_f = 0.53$ (O) | c) | analogously to Example No. 21 (from Example No. 246) |
| 299 | R | rac | 4-CH$_2$OH | $R_f = 0.27$ (AE) | c) | analogously to Example No. XXXII and XXXIII |

TABLE 25
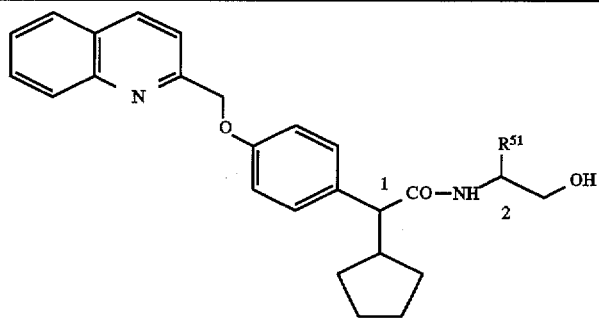
| Example No. | 1 | 2 | ⊣R51 | R_f value (solvent) | Starting material Preparation from Example No. |
|---|---|---|---|---|---|
| 300 | R | rac | 2-naphthyl | R_f = 0.20 (O) | 262 |
| 301 | R | rac | 3,4-methylenedioxyphenyl | R_f = 0.32 (AH) | 263 |
| 302 | R | rac | 3-pyridyl | R_f = 0.06 (W) | 261 |
| 303 | R | S | 2-thienyl | R_f = 0.40 (O) | 265 |
| 304 | S | rac | 2-thienyl | R_f = 0.28/0.38 (O) | 264 |
| 305 | S | S | 2-thienyl | R_f = 0.36 (O) | 264 |
| 306 | R | R | 2-thienyl | R_f = 0.32 (O) | 265 |

TABLE 26

| Ex. No. | (1) | (2) | R52 | Rf value (solvent) Melting point [°C.] | Starting material a) Literature b) Distributing company c) Preparation analogously to Ex. No. |
|---|---|---|---|---|---|
| 307 | R | dia A | 4-N(pyrrolidinyl) | Rf = 0.26 (O) | c) analogously to Example No. XXXII and XXXIII |
| 308 | R | dia B | 4-N(pyrrolidinyl) | Rf = 0.21 (O) | c) analogously to Example No. XXXII and XXXIII |
| 309 | R | dia A | 4-OCF3 | Rf = 0.33 (O) | c) analogously to Example No. XXXII and XXXIII |
| 310 | R | dia B | 4-OCF3 | Rf = 0.26 (O) | c) analogously to Example No. XXXII and XXXIII |
| 311 | R | dia A | 2-OH | Rf = 0.39 (O) | c) analogously to Example No. XXXII and XXXIII (from Example No. XXXV) |
| 312 | R | dia B | 2-OH | Rf = 0.26 (O) | c) analogously to Example No. XXXII and XXXIII (from Example No. XXXV) |
| 313 | R | S | 4-Cl | Rf = 0.32 (O) | c) analogously to Example No. 21 |
| 314 | R | dia A | 4-Ph | Rf = 0.40 (O) | c) analogously to Example No. XXXII and XXXIII (from Example No. IV) |
| 315 | R | dia B | 4-Ph | Rf = 0.35 (O) | c) analogously to Example No. XXXII and XXXIII (from Example No. IV) |
| 316 | R | dia A | 4-N(morpholinyl) | Rf = 0.09 (AH) | c) analogously to Example No. XXXII and XXXIII (from Example No. VI) |
| 317 | R | dia B | 4-N(morpholinyl) | Rf = 0.09 (AH) | c) analogously to Example No. XXXII and XXXIII (from Example No. VI) |
| 318 | R | dia A | 3-CF3 | Rf = 0.48 (O) | c) analogously to Example No. XXXII and XXXIII |
| 319 | R | rac | 3-OH | Rf = 0.21 (AH) | c) analogously to Example No. XXXII and XXXIII (from Example No. XXXVI) |
| 320 | R | dia B | 3-CF3 | Rf = 0.41 (O) | c) analogously to Example No. XXXII and XXXIII |
| 321 | R | rac | 4-OH | Rf = 0.21 (AH) | c) analogously to Example No. XXXII and XXXIII (from Example No. XXXVII) |

TABLE 27

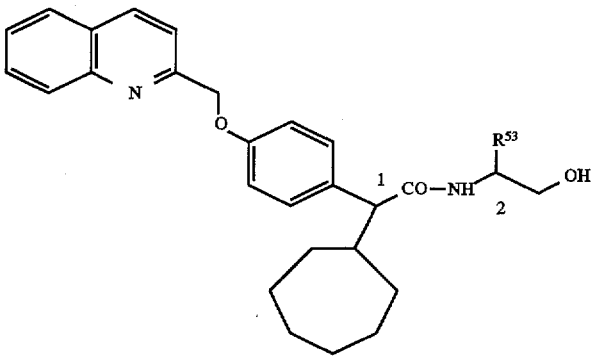

| Example No. | 1 | 2 | R⁵³ | $R_f$ value (solvent) | Starting material Preparation from Example No. |
|---|---|---|---|---|---|
| 322 | R | dia B | (2-naphthyl) | $R_f$ = 0.36 (O) | V |
| 323 | R | dia A | (2-naphthyl) | $R_f$ = 0.40 (O) | V |

TABLE 28

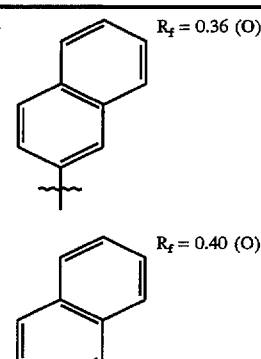

| Example No. | 1 | 2 | R⁵⁴ | $R_f$ value (solvent) | Starting material Preparation from Example No. |
|---|---|---|---|---|---|
| 324 | R | dia A | 3-CF₃ | $R_f$ = 0.02 (AH) | 251 |
| 325 | R | dia B | 3-CF₃ | $R_f$ = 0.02 (AH) | 252 |
| 326 | R | dia A | 4-OCF₃ | $R_f$ = 0.02 (AH) | 257 |
| 327 | R | dia B | 4-OCF₃ | $R_f$ = 0.02 (AH) | 258 |
| 328 | R | dia B | 4-F, 3-OPh | $R_f$ = 0.02 (AH) | 254 |
| 329 | R | S | H | $R_f$ = 0.01 (AH) | 255 |
| 330 | R | R | H | $R_f$ = 0.01 (AH) | 259 |
| 331 | S | S | H | $R_f$ = 0.01 (AH) | 256 |
| 332 | R | dia A | 4-F, 3-OPh | $R_f$ = 0.02 (AH) | 253 |

TABLE 29

| Example No. | 1 | 2 | R⁵⁵ | $R_f$ value (solvent) | Starting material Preparation from Example No. |
|---|---|---|---|---|---|
| 333 | R | rac | naphthalen-2-yl | $R_f$ = 0.69 (AJ) | 262 |
| 334 | R | rac | pyridin-3-yl | $R_f$ = 0.55 (AE) | 261 |
| 335 | rac | rac | 1,3-benzodioxol-5-yl | $R_f$ = 0.31 (C) | 263 |
| 336 | S | rac | thiophen-2-yl | $R_f$ = 0.56 (C) | 264 |
| 337 | R | rac | thiophen-2-yl | $R_f$ = 0.53 (C) | 265 |

TABLE 30

Structure: Quinoline-CH2-O-C6H4-C(R1)(R2)-CO-NH-CH(Ph)-CONH2 with positions 1 and 2 indicated.

| Example No. | 1 | 2 | R¹ | R² | $R_f$ value (solvent) |
|---|---|---|---|---|---|
| 338 | rac | S | OH | cHex | $R_f$ = 0.52 (AE) |
| 339 | R | S | H | cPent | $R_f$ = 0.61 (AJ) |
| 340 | S | S | H | cPent | $R_f$ = 0.48 (AJ) |
| 341 | R | R | H | cPent | $R_f$ = 0.38 (Z) |
| 342 | rac | rac | OH | 2-indanyl | $R_f$ = 0.48 (AE) |
| 343 | rac | rac | H | cDodec | $R_f$ 0.34 (F) |
| 344 | rac | rac | H | cOct | $R_f$ = 0.30 (F) |

D,L-Phenylglycincamide is commercially obtainable from Bader.

TABLE 31

Structure: Quinoline-CH2-O-C6H4-CH(cPentyl)-CO-NH-CH(Ar-R56)-CONH2 with phenyl positions 2-6 shown.

| Example No. | (1) | (2) | R⁵⁶ | $R_f$ value (solvent) | Starting material Preparation from Example No. |
|---|---|---|---|---|---|
| 345 | R | rac | 4-Cl | $R_f$ = 0.47 (AD) | 240 |
| 346 | R | S | 4-Cl | $R_f$ = 0.48 (AE) | 241 |
| 347 | S | S | 4-Cl | $R_f$ = 0.61 (AJ) | 240/241 |
| 348 | S | R | 4-Cl | $R_f$ = 0.45 (AD) | 240/241 |
| 349 | R | rac | 4-OCF₃ | $R_f$ = 0.35 (Z) | 257 |
| 350 | R | rac | 4-Ph | $R_f$ = 0.51 (AJ) | 239 |
| 351 | R | rac | 4-cPr | $R_f$ = 0.48 (AJ) | 235 |
| 352 | R | rac | 4-cPr | $R_f$ = 0.47 (AJ) | 236 |
| 353 | R | rac | 4-tBu | $R_f$ = 0.55/0.50 (Z) | 237/238 |
| 354 | R | rac | 4-OCF₃ | $R_f$ = 0.28 (AJ) | 258 |
| 355 | R | rac | 4-morpholino | $R_f$ = 0.33 (AE) | 249 |
| 356 | rac | rac | 2-OH | $R_f$ = 0.38 (AG) | 242/243 |
| 357 | rac | rac | 4-OH | $R_f$ = 0.30 (C) | 245 |

TABLE 31-continued

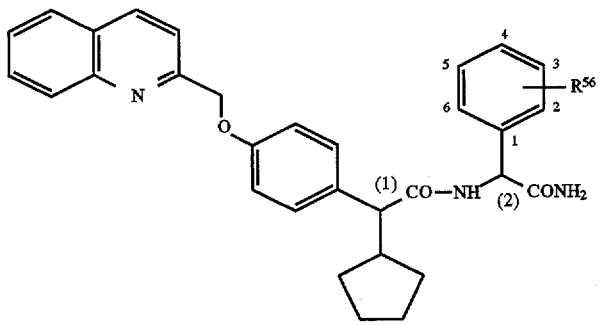

| Example No. | (1) | (2) | $R^{56}$ | $R_f$ value (solvent) | Starting material Preparation from Example No. |
|---|---|---|---|---|---|
| 358 | | rac dia A | 4-OH | $R_f = 0.27$ (C) | 245 |
| 359 | rac | rac | 3-OH | $R_f = 0.31$ (C) | 244 |
| 360 | rac | rac | 4-F, 3-OPh | $R_f = 0.52$ (C) | 253/254 |
| 361 | rac | rac | 4-$SO_2$Ph | $R_f = 0.47$ (C) | 247 |
| 362 | R | rac | 3-$CF_3$ | $R_f = 0.33$ (F) | 251/252 |

TABLE 32

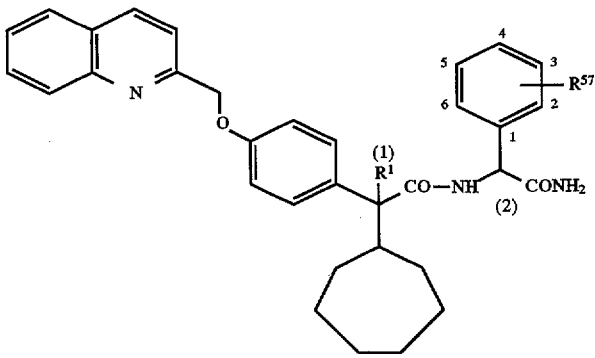

| Example No. | (1) | (2) | $R^1$ | $R^{57}$ | $R_f$ value (solvent) | Starting material Preparation from Example No. |
|---|---|---|---|---|---|---|
| 363 | rac dia A | | H | H | $R_f = 0.19$ (O) | analogously to Example No. XXXII and XXXIII* |
| 364 | rac dia B | | H | H | $R_f = 0.19$ (O) | analogously to Example No. XXXII and XXXIII* |
| 365 | R | rac | H | 4-morpholinyl | $R_f = 0.30$ (Z) | analogously to Example No. 76 |
| 366 | rac dia A | | OH | H | $R_f = 0.16$ (O) | analogously to Example No. XXXII and XXXIII* |
| 367 | rac dia B | | OH | H | $R_f = 0.16$ (O) | analogously to Example No. XXXII and XXXIII* |
| 368 | rac | rac | H | 2-OH | $R_f = 0.14$ (O) | analogously to Example No. 76 |
| 369 | rac | rac | H | 3-OH | $R_f = 0.30$ (AG) | analogously to Example No. 76 |
| 370 | rac | rac | H | 4-pyrrolidinyl | $R_f = 0.28$ (O) | analogously to Example No. 76 |

TABLE 32-continued

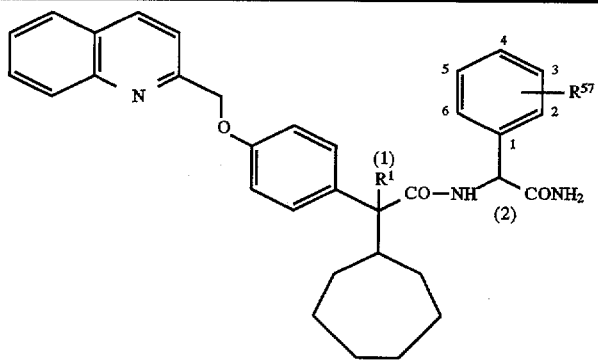

| Example No. | (1) | (2) | $R^1$ | $R^{57}$ | $R_f$ value (solvent) | Starting material Preparation from Example No. |
|---|---|---|---|---|---|---|
| 371 | rac | dia A | H | 4- ⌐N⌐ | $R_f = 0.28$ (O) | analogously to Example No. 76 |
| 372 | R | dia A | H | H | $R_f = 0.17$ (O) | analogously to Example No. XXXII and XXXIII* |
| 373 | R | dia B | H | H | $R_f = 0.17$ (O) | analogously to Example No. XXXII and XXXIII* |
| 374 | S | dia A | H | H | $R_f = 0.26$ (O) | analogously to Example No. XXXII and XXXIII* |
| 375 | S | dia B | H | H | $R_f = 0.26$ (O) | analogously to Example No. XXXII and XXXIII* |

*D,L-Phenylglycineamide is commercially obtainable from Bader.

TABLE 33

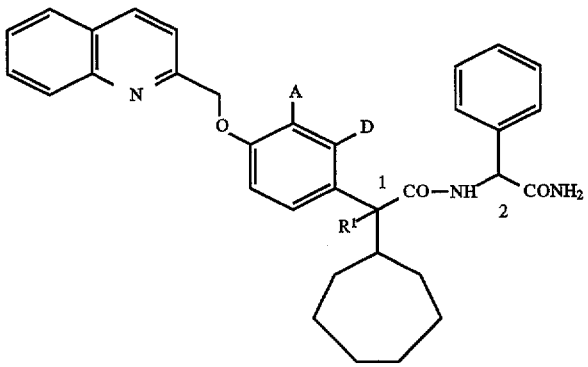

| Example No. | 1 | 2 | A | D | R¹ | $R_f$ value (solvent) |
|---|---|---|---|---|---|---|
| 376 | rac | rac | H | —CH$_2$=CH$_2$ | H | $R_f$ = 0.56 (AE) |
| 377 | rac | rac | H | iBu | H | $R_f$ = 0.67/061 (AE) |
| 378 | rac | rac | iBu | H | H | $R_f$ = 0.35 (F) |
| 379 | rac | rac | pyrrolyl | H | H | $R_f$ = 0.33 (F) |
| 380 | rac | rac | OMe | H | OH | $R_f$ = 0.28 (F) |
| 381 | rac | rac | iBu | H | OH | $R_f$ = 0.30 (F) |
| 382 | rac | rac | F | H | H | $R_f$ = 0.30 (F) |

D,L-Phenylglycinamide is commercially obtainable from Bader.

TABLE 34

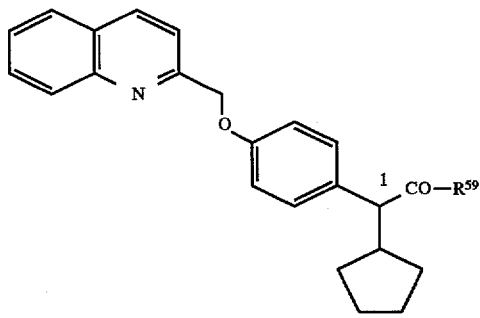

| Example | 1 | —R⁵⁹ | $R_f$ value (solvent) Melting point [°C.] | Starting material<br>a) Literature<br>b) Distributing company<br>c) Synthesis anologously to/from Example No. |
|---|---|---|---|---|
| 383 | S | N(Me)(Me)-CH(Me)-CH(OH)Ph | $R_f$ = 0.49 (AK) | b) Aldrich |
| 384 | R | N(Me)(Me)-CH(Me)-CH(OH)Ph | m.p = 109° C. | b) Aldrich |
| 385 | S | N(Me)(Me)-CH(Me)-CH(OH)Ph | $R_f$ = 0.49 (AK) | b) Aldrich |

TABLE 34-continued

[Structure: quinoline-CH2-O-phenyl-CH(1)(CO-R^59)-cyclopentyl]

| Example | 1 | −R^59 | R_f value (solvent) Melting point [°C.] | Starting material a) Literature b) Distributing company c) Synthesis anologously to/from Example No. |
|---|---|---|---|---|
| 386 | S | [structure: Me-CH(NMe2)-CH(OH)-Ph] | R = 0.48 (AK) | b) Aldrich |
| 387 | S | [structure: NH-CH2-CH(OH)-Ph] | m.p. = 173° C. | b) Aldrich |
| 388 | R | [structure: NH-CH2-CH(OH)-Ph] | m.p. = 161° C. | b) Aldrich |
| 389 | R | [structure: NH-CH2-CH(OH)-2-pyridyl] | $R_f$ = 0.43 (AL) | a) F. Zymalkowski Arch. Pharm. 291, 12 (1958). |
| 390 | S | [structure: NH-CH2-CH(OH)-2-pyridyl] | $R_f$ = 0.42 (AL) | a) F. Zymalkowski Arch. Pharm. 291, 12 (1958). |
| 391 | R | [structure: NH-CH2-CH(OH)-CH2-NEt2] | $R_f$ = 0.39 (B) | b) K & K |
| 392 | S | [structure: NH-CH2-CH(OH)-CH2-NEt2] | $R_f$ = 0.39 (B) | b) K & K |
| 393 | S | [structure: NH-CH2-CH(OH)-CH2-O-CH2-CH=CH2] | m.p. = 118° C. | b) K & K |
| 394 | R | [structure: NH-CH2-CH(OH)-CH2-O-CH2-CH=CH2] | m.p. = 120° C. | b) K & K |
| 395 | S | [structure: NH-CH2-CH(OH)-(3-OBn-phenyl)] | $R_f$ = 0.53 (AK) | a) J. Millen et al., J. Med. Chem. 28, 12 (1985). |

TABLE 34-continued

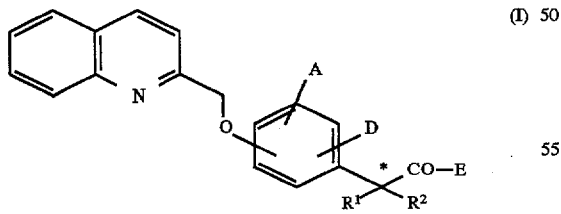

| Example | 1 | —R⁵⁹ | $R_f$ value (solvent) Melting point [°C.] | Starting material a) Literature b) Distributing company c) Synthesis anologously to/from Example No. |
|---|---|---|---|---|
| 396 | R | (NH-CH₂-CH(OH)-phenyl-OBn, meta) | $R_f$ = 0.53 (AK) | a) J. Millen et al., J. Med. Chem. 28, 12 (1985). |
| 397 | S | (NH-CH₂-CH(OH)-norbornyl) | $R_f$ = 0.58 (AK) | a) D. P. Davis et al., J. Med. Chem. 24, 12 (1981) |
| 398 | R | (NH-CH₂-CH(OH)-norbornyl) | $R_f$ = 0.57 (AK) | a) D. P. Davis et al., J. Med. Chem. 24, 12 (1981) |
| 399 | S | NH-CH₂-CH(OH)-nBu | $R_f$ = 0.60 (AK) | a) EP 518 672 |
| 400 | R | NH-CH₂-CH(OH)-nBu | $R_f$ = 0.60 (AK) | a) EP 518 672 |

We claim:

1. 4-(Quinolin-2-yl-methoxy)-phenyl-acetic acid derivatives of the general formula (I)

in which

A and D are identical or different and represent hydrogen, cycloalkyl having 3 to 8 carbon atoms, azido, hydroxyl, halogen, straight-chain or branched alkyl, alkoxy or alkenyl having in each case up to 6 carbon atoms, or a 5- to 6- membered unsaturated or saturated heterocyclic radical having up to 3 heteroatoms from the series consisting of S, N and/or O, $R^1$ represents hydrogen or hydroxyl, or represents straight-chain or branched alkyl having up to 4 carbon atoms, $R^2$ represents hydrogen, hydroxyl, halogen, straight-chain or branched alkenyl or alkoxy having in each case up to 8 carbon atoms or cycloalkyl having 3 to 14 carbon atoms, or represents straight-chain or branched alkyl having up to 8 carbon atoms, which is optionally substituted by cycloalkyl having 3 to 14 carbon atoms, phenyl or tetrahydropyranyl, which in their turn can be substituted by halogen, or represents the indanyl radical, or $R^1$ and $R^2$ together with the carbon atom form a saturated carbocyclic ring having 5 to 7 carbon atoms, or $R^1$ and $R^2$ together represent a double bond radical of the formula

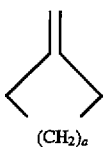

wherein
a denotes the number 2, 3, 4, 5, or 6,
E represents a radical of the formula

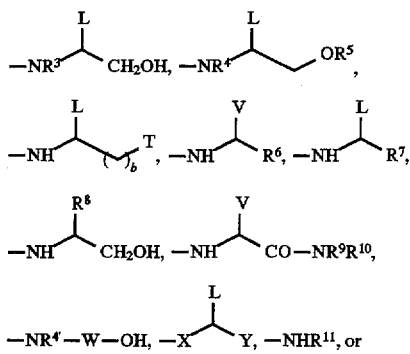

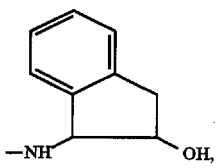

in which
R$^3$ denotes phenyl, methyl or a typical amino-protective group,
R$^4$ and R$^4$ are identical or different and have the above-mentioned meaning of R$^3$ or denote hydrogen,
R$^5$ denotes straight-chain or branched acyl or alkyl having in each case up to 4 carbon atoms,
L denotes phenyl, benzyl or naphthyl, which is optionally substituted up to twice in an identical or different manner by halogen, hydroxyl, pyrrolidinyl, morpholino, amino, trifluoromethyl, trifluoromethoxy, cycloalkyl having 3 to 6 carbon atoms or straight-chain or branched alkyl or alkoxy having in each case up to 6 carbon atoms, which in their turn can be substituted by hydroxyl, or are optionally substituted by phenyl or phenoxy, which in their turn can be substituted up to twice in an identical or different manner by halogen or by straight-chain or branched alkyl having up to 4 carbon atoms, and/or are optionally substituted by a group of the formula —(O)$_c$—SO$_2$R$^{12}$,
wherein
c denotes the number 0 or 1 and
R$^{12}$ denotes straight-chain or branched alkyl having up to 4 carbon atoms or phenyl,
b denotes the number 0, 1 or 2,
T denotes a 5 to 7-membered, optionally benzo-fused, saturated, partially unsaturated or unsaturated heterocyclic radical having up to 3 heteroatoms from the series consisting of S, N and/or O, wherein both rings are optionally substituted up to three times in an identical or different manner by halogen, hydroxyl, morpholino, amino, cycloalkyl having 3 to 6 carbon atoms, straight-chain or branched alkyl or alkoxy having in each case up to 6 carbon atoms or phenyl, V has the abovementioned meaning of L or T or denotes a radical of the formula

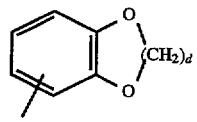

wherein
d denotes the number 1, 2 or 3,
R$^6$ denotes a radical of the formula —(CH$_2$)$_e$—R$^{13}$,
wherein
e denotes the number 0 or 1,
R$^{13}$ denotes hydroxyl, carboxyl or straight-chain or branched alkoxycarbonyl having up to 4 carbon atoms,
R$^7$ denotes hydrogen, cyano, trifluoromethyl or straight-chain or branched alkenyl or alkyl having up to 7 carbon atoms, which is optionally substituted up to twice in an identical or different manner by straight-chain or branched alkoxy having up to 4 carbon atoms, or denotes alkoxy having up to 6 carbon atoms, or denotes a group of the formula —CO—NH—(CH$_2$)$_f$—NR$^{14}$R$^{15}$,
wherein
f denotes the number 1, 2 or 3,
R$^{14}$ and R$^{15}$ are identical or different and
denote hydrogen, phenyl or straight-chain or branched alkyl having up to 4 carbon atoms,
R$^8$ denotes hydrogen, carboxyl, straight-chain or branched alkoxycarbonyl having up to 4 carbon atoms or straight-chain or branched alkyl having up to 5 carbon atoms, which is optionally substituted by hydroxyl, carboxyl or by straight-chain or branched alkoxycarbonyl having in each case up to 4 carbon atoms or phenyl,
R$^9$ and R$^{10}$ are identical or different and
denote hydrogen, cycloalkyl having 3 to 6 carbon atoms or phenyl, or
denote straight-chain or branched alkyl having up to 6 carbon atoms, which is optionally substituted by phenyl, cycloalkyl having 3 to 6 carbon atoms, hydroxyl, carboxyl, by straight-chain or branched alkoxy or alkoxycarbonyl having in each case up to 4 carbon atoms or by a group of the formula —NR$^{16}$R$^{17}$ wherein
R$^{16}$ and R$^{17}$ are identical or different and denote hydrogen, phenyl
or straight-chain or branched alkyl having up to 4 carbon atoms,
or
R$^9$ and R$^{10}$ together with the nitrogen atom form a heterocyclic radical of the formula

wherein
Z denotes an oxygen atom or the group —NR$^{18}$ or —CH,
wherein
R$^{18}$ denotes hydrogen, acetyl, a typical amino-protective group or a radical of the formula —SO$_2$R$^{19}$.

wherein

R$^{19}$ denotes straight-chain or branched alkyl having up to 4 carbon atoms, benzyl or phenyl, which is optionally substituted by phenyl or tolyl, W denotes straight-chain or branched alkyl having 2 to 7 carbon atoms, which is substituted one to three times in an identical or different manner by hydroxyl, pyridyl, norbornyl or phenyl, which in its turn can be substituted by hydroxyl or benzyloxy, or is substituted by a group of the formula —OR$^{20}$ or —NR$^{21}$R$^{22}$, wherein R$^{20}$ denotes straight-chain or branched alkyl having up to 6 carbon atoms and R$^{21}$ and R$^{22}$ are identical or different and have the abovementioned meaning of R$^{16}$ and R$^{17}$, X denotes an oxygen or sulphur atom, Y denotes formyl or the group —CHR$^{23}$R$^{24}$, wherein R$^{23}$ denotes hydrogen and R$^{24}$ denotes hydroxyl or straight-chain or branched alkoxy or acyl having in each case up to 4 carbon atoms, or R$^{23}$ and R$^{24}$ are identical or different and denote straight-chain or branched alkoxy having up to 4 carbon atoms, R$^{11}$ denotes a radical of the formula

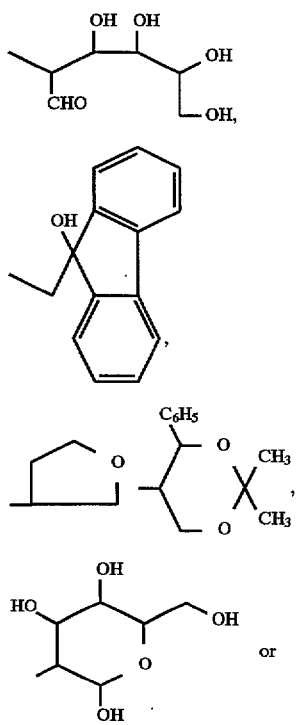

or phenyl which is optionally substituted up to twice in an identical or different manner by halogen, carboxyl or straight-chain or branched alkoxycarbonyl having up to 5 carbon atoms, or denotes straight-chain or branched alkyl having up to 6 carbon atoms, which is optionally substituted up to twice in an identical or different manner by hydroxyl, carboxyl, halogen or by straight-chain or branched alkoxycarbonyl having up to 5 carbon atoms, and salts thereof, wherein 2-[4-(quinolin-2-yl-methoxy)-phenyl]-2-cyclopentylacetic acid [(L)-2-hydroxy-1-phenylethyl] amide 2-[4-(quinolin-2-yl-methoxy)phenyl]-2-cyclopentyl-acetic acid methyloxycarbonylmethylamide, 2-[4-(quinolin-2-yl-methoxy)phenyl]-2-cyclopentyl-acetic acid carboxymethylamide, N-methyl-2-[3-isobutyl-4-(quinolin-2-yl-methoxy)phenyl]-2-cycloheptylacetamide, N-methyl-2-[4-(quinolin-2-yl-methoxy)phenyl]-2-cycloheptyl-acetic acid amide, N-ethyl-2-[4-(quinolin-2-yl-methoxy)phenyl]-2-cyclopentyl-acetic acid amide and N-ethyl-2-[4-(quinolin-2-yl-methoxy)phenyl]-2-cyclohexyl-acetic acid amide are excluded.

2. 4-(Quinolin-2-yl-methoxy)-phenyl-acetic acid derivatives according to claim 1, wherein A and D are identical or different and represent hydrogen, cyclopropyl, cyclopentyl, cyclohexyl, azido, hydroxyl, fluorine, chlorine, bromine, straight-chain or branched alkyl, alkoxy or alkenyl having in each case up to 5 carbon atoms, pyrryl or imidazolyl, R$^1$ represents hydrogen or hydroxyl or represents straight-chain or branched alkyl having up to 3 carbon atoms, R$^2$ represents hydrogen, hydroxy, fluorine, chlorine, bromine, straight-chain or branched alkenyl or alkoxy having in each case up to 7 carbon atoms, cyclopentyl, cyclohexyl, cycloheptyl, cyclooctyl, cyclononyl, cyclodecyl, cycloundecyl or cyclododecyl, or represents straight-chain or branched alkyl having up to 7 carbon atoms, which is optionally substituted by cyclopentyl, cyclohexyl, cycloheptyl, cyclooctyl, cyclononyl, cyclodecyl, cycloundecyl or cyclododecyl, phenyl or tetrahydropyranyl, which in their turn can be substituted by fluorine, chlorine or bromine, or represents the indanyl radical, or R$^1$ and R$^2$ together with the carbon atom form a cyclopentyl, cyclohexyl or cycloheptyl ring, or R$^1$ and R$^2$ together represent a double bond radical of the formula

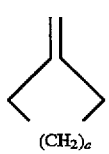

wherein a denotes the number 2, 3, 4 or 5,

E represents a radical of the formula

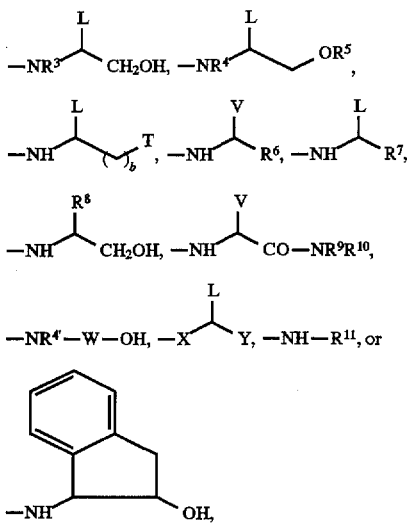

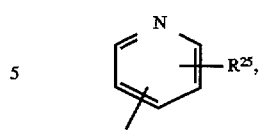

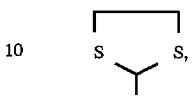

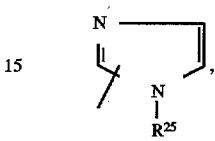

in which

R³ denotes phenyl, methyl, acetyl or tert-butoxycarbonyl (Boc),

R⁴ and R⁴' are identical or different and have the above-mentioned meaning of R³ or denote hydrogen, R⁵ denotes straight-chain or branched acyl or alkyl having in each case up to 3 carbon atoms, L denotes phenyl, benzyl or naphthyl, which are optionally substituted up to twice in an identical or different manner by fluorine, chlorine, bromine, iodine, hydroxyl, pyrrolidinyl, morpholino, amino, trifluoromethyl, trifluoromethoxy, cyclopropyl, cyclopentyl, cyclohexyl or straight-chain or branched alkyl or alkoxy having in each case up to 6 carbon atoms, which in their turn can be substituted by hydroxyl or are optionally substituted by phenyl or phenoxy, which in their turn can be substituted up to twice in an identical or different manner by fluorine, chlorine, bromine or by straight-chain or branched alkyl having up to 3 carbon atoms, and/or are optionally substituted by a group of the formula —(O)$_c$SO$_2$—R¹², wherein c denotes the number 0 or 1, and R¹² denotes straight-chain or branched alkyl having up to 4 carbon atoms or phenyl, b denotes the number 0 or 1, T denotes a heterocyclic radical of the formula

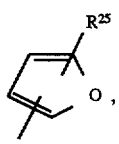

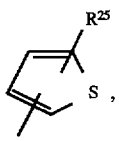

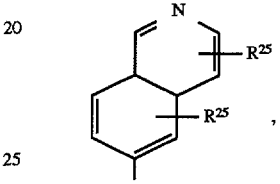

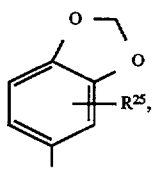

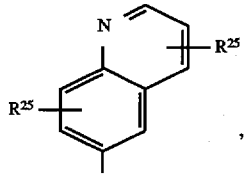

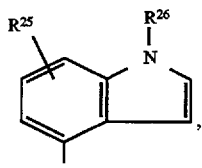

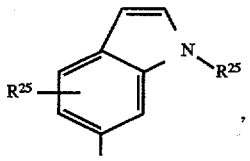

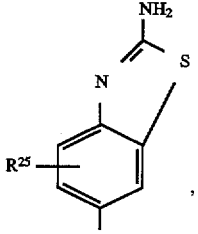

-continued

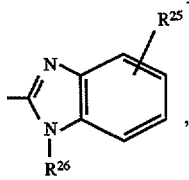

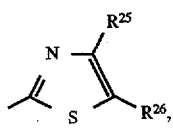

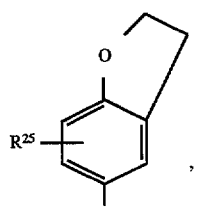

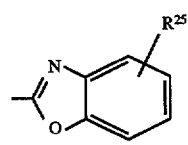

or

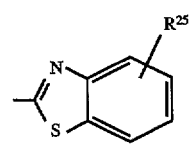

wherein
R$^{25}$ and R$^{26}$ are identical or different and denote hydrogen, straight-chain or branched alkyl having up to 4 carbon atoms or amino,
V has the abovementioned meaning of L or T or denotes a radical of the formula

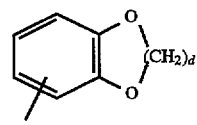

wherein
denotes the number 1 or 2,
R$^6$ denotes a radical of the formula —(CH$_2$)$_e$—R$^{13}$,
wherein
e denotes the number 0 or 1,
R$^{13}$ denotes hydroxyl, carboxyl or straight-chain or branched alkoxycarbonyl having up to 3 carbon atoms,
R$^7$ denotes hydrogen, cyano, trifluoromethyl, vinyl or straight-chain or branched alkyl having up to 6 carbon atoms, which is optionally substituted up to twice in an identical or different manner by straight-chain or branched alkoxy having up to 3 carbon atoms, or denotes alkoxy having up to 5 carbon atoms, or denotes a group of the formula —CO—NH—(CH$_2$)$_f$—NR$^{14}$R$^{15}$
wherein
f denotes the number 1, 2 or 3,
R$^{14}$ and R$^{15}$ are identical or different and denote hydrogen, phenyl or straight-chain or branched alkyl having up to 3 carbon atoms,
R$^8$ denotes hydrogen, carboxyl, straight-chain or branched alkoxycarbonyl having up to 3 carbon atoms or straight-chain or branched alkyl having up to 5 carbon atoms, which is optionally substituted by hydroxyl, carboxyl or by straight-chain or branched alkoxycarbonyl having in each case up to 3 carbon atoms or phenyl,
R$^9$ and R$^{10}$ are identical or different and
denote hydrogen, cyclopropyl, cyclopentyl, cyclohexyl or phenyl, or
denote straight-chain or branched alkyl having up to 5 carbon atoms, which is optionally substituted by phenyl, cyclopropyl, cyclopentyl, cyclohexyl, hydroxyl, carboxyl, by straight-chain or branched alkoxy or alkoxycarbonyl having in each case up to 3 carbon atoms or by a group of the formula —NR$^{16}$R$^{17}$,
wherein
R$^{16}$ and R$^{17}$ are identical or different and denote hydrogen, phenyl or straight-chain or branched alkyl having up to 3 carbon atoms,
or
R$^9$ and R$^{10}$ together with the nitrogen atom form a heterocyclic radical of the formula

wherein
Z denotes an oxygen atom or the group —NR$^{18}$ or —CH,
wherein
R$^{18}$ denotes hydrogen, acetyl, tert-butoxycarbonyl or a radical of the formula —SO$_2$R$^{19}$,
wherein
R$^{19}$ denotes straight-chain or branched alkyl having up to 3 carbon atoms, benzyl or phenyl, which is optionally substituted by phenyl or tolyl,
W denotes straight-chain or branch alkyl having 2 to 7 carbon atoms, which is substituted 1 to 3 times in an identical or different manner by hydroxyl, pyridyl, norbornyl or phenyl, which in its turn can be substituted by hydroxyl or benzyloxy, or is substituted by a group of the formula —OR$^{20}$ or —NR$^{21}$R$^{22}$,
wherein
R$^{20}$ denotes straight-chain or branched alkyl having up to 5 carbon atoms and
R$^{21}$ and R$^{22}$ are identical or different and have the abovementioned meaning of R$^{16}$ and R$^{17}$,
X denotes an oxygen or sulphur atom,
Y denotes formyl or the group —CHR$^{23}$R$^{24}$,
wherein
R$^{23}$ denotes hydrogen,
R$^{24}$ denotes hydroxyl or straight-chain or branched alkoxy or acyl having in each case up to 3 carbon atoms,
or
R$^{23}$ and R$^{24}$ are identical or different and denote straight-chain or branched alkoxy having up to 3 carbon atoms, $R^{11}$ denotes a radical of the formula

[chemical structure: pentose-like chain with CHO, OH groups]

[chemical structure: fluorene with OH and ethyl substituents]

[chemical structure: cyclic acetal with C₆H₅ and two CH₃ groups]

[chemical structure: cyclic sugar with HO, OH groups]

or phenyl, which is optionally substituted up to twice in an identical or different manner by fluorine, chlorine, bromine, carboxyl or straight-chain or branched alkoxycarbonyl having up to 4 carbon atoms, or denotes straight-chain or branched alkyl having up to 5 carbon atoms, which is optionally substituted up to twice in an identical or different manner by hydroxyl, carboxyl, fluorine, chlorine, bromine or by straight-chain or branched alkoxycarbonyl having up to 4 carbon atoms, and salts thereof, wherein 2-[4-(quinolin-2-yl-methoxy)-phenyl]-2-cyclopentylacetic acid [(L)-2-hydroxy-1-phenylethyl] amide 2-[4-(quinolin-2-yl-methoxy)phenyl]-2-cyclopentyl-acetic acid methyloxycarbonylmethylamide, 2-[4-(quinolin-2-yl-methoxy)phenyl]-2-cyclopentyl-acetic acid carboxymethylamide, N-methyl-2-[3-isobutyl-4-(quinolin-2-yl-methoxy) phenyl]- 2-cycloheptylacetamide, N-methyl-2-[4-(quinolin-2-yl-methoxy)phenyl]-2-cycloheptyl-acetic acid amide, N-ethyl-2-[4-(quinolin-2-yl-methoxy)phenyl]-2-cyclopentyl-acetic acid amide and N-ethyl-2-[4-(quinolin-2-yl-methoxy)phenyl]-2-cyclohexyl-acetic acid amide are excluded.

3. 4-(Quinolin-2-yl-methoxy)-phenyl-acetic acid derivatives according to claim 1, wherein A and D are identical or different and
represent hydrogen, cyclopropyl, cyclopentyl, cyclohexyl, azido, hydroxyl, fluorine, chlorine, bromine, straight-chain or branched alkyl, alkoxy or alkenyl having in each case up to 4 carbon atoms, imidazolyl or pyrryl, $R^1$ represents hydrogen, hydroxyl or straight-chain or branched alkyl having up to 3 carbon atoms, $R^2$ represents hydrogen, hydroxyl, fluorine, chlorine, straight-chain or branched alkenyl or alkoxy having in each case up to 5 carbon atoms, cyclopentyl, cyclohexyl, cycloheptyl, cyclooctyl, cyclononyl, cyclodecyl or cycloundecyl or represents straight-chain or branched alkyl having up to 6 carbon atoms, which is optionally substituted by cyclopentyl, cyclohexyl, cycloheptyl, cyclooctyl, cyclononyl, cycloundecyl, phenyl or tetrahydropyranyl, which in their turn can be substituted by fluorine, chlorine or bromine, or represents the indanyl radical, $R^1$ and $R^2$ together with the carbon atom form a cyclopentyl, cyclohexyl or cycloheptyl ring, E represents a radical of the formula

[chemical structures showing various E substituents with L, V, T, R⁵–R¹¹, W, X, Y groups]

$-NR^3 \overset{L}{\frown} CH_2OH$, $-NR^4 \overset{L}{\frown} OR^5$, $-NH \overset{L}{\frown} T$, $-NH \overset{V}{\frown} R^6$, $-NH \overset{L}{\frown} R^7$, $-NH \overset{R^8}{\frown} CH_2OH$, $-NH \overset{V}{\frown} CO-NR^9R^{10}$, $-NR^{4'}-W-OH$, $-X \overset{L}{\frown} Y$, $-NHR^{11}$, or

[indanyl structure with -NH and OH]

in which $R^3$ denotes phenyl, methyl, acetyl or tert-butoxycarbonyl (Boc), $R^4$ and $R^{4'}$ are identical or different and have the above-mentioned meaning of $R^3$ or denote hydrogen, $R^5$ denotes straight-chain or branched acyl or alkyl having in each case up to 3 carbon atoms, L denotes phenyl, benzyl or naphthyl, which are optionally substituted up to twice in an identical or different manner by fluorine, chlorine, bromine, iodine, hydroxyl, pyrrolidinyl, morpholino, trifluoromethoxy, trifluoromethyl, amino, cyclopropyl, cyclopentyl, cyclohexyl or straight-chain or branched alkyl or alkoxy having in each case up to 6 carbon atoms, which in their turn can be substituted by hydroxyl, or are optionally substituted by phenyl or phenoxy, which in their turn can be substituted up to twice in an identical or different manner by fluorine, chlorine or by straight-chain or branched alkyl having up to 3 carbon atoms, and/or are optionally substituted by a group of the formula $-(O)_cSO_2-R^{12}$, wherein denotes the number 0 or 1, and $R^{12}$ denotes straight-chain or branched alkyl having up to 3 carbon atoms or phenyl, b denotes the number 0 or 1, T denotes a heterocyclic radical of the formula

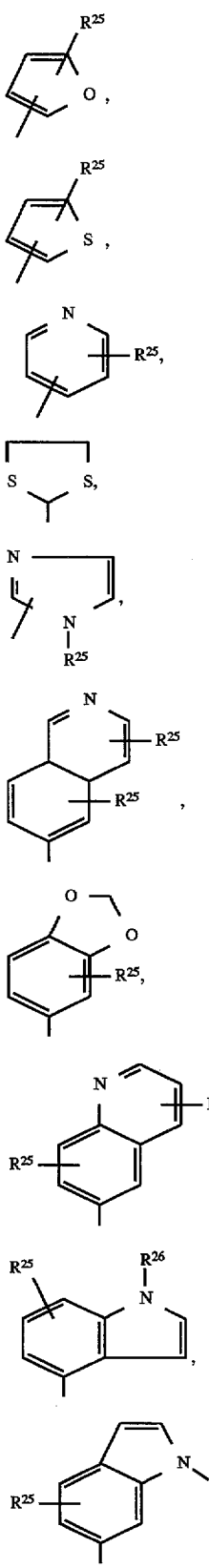

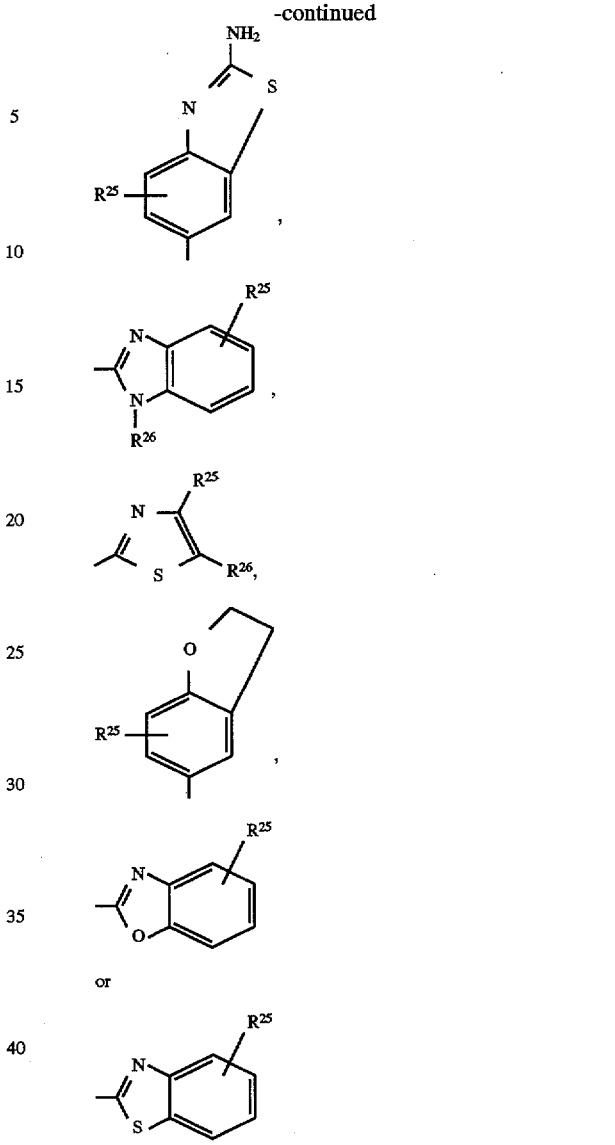

wherein
$R^{25}$ and $R^{26}$ are identical or different and denote hydrogen, straight-chain or branched alkyl having up to 4 carbon atoms or amino, V has the abovementioned meaning of L or T or denotes a radical of the formula

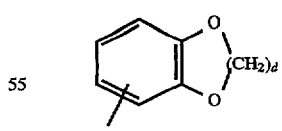

wherein
d denotes the number 1 or 2, $R^6$ denotes a radical of the formula —$(CH_2)_e$—$R^{13}$,
wherein
e denotes the number 0 or 1,
$R^{13}$ denotes hydroxyl, carboxyl or straight-chain or branched alkoxycarbonyl having up to 3 carbon atoms,
wherein $R^7$ denotes hydrogen, cyano, trifluoromethyl, vinyl or straight-chain or branched alkyl having up to 5 carbon atoms, which is optionally substituted up to twice in an identical or different manner by straight-chain or branched alkoxy having up to 3 carbon atoms, or denotes alkoxy having up to 3 carbon atoms, or denotes a group of the formula —CO—NH—$(CH_2)_f$—$NR^{14}R^{15}$, wherein f denotes the number 1, 2 or 3, $R^{14}$ and $R^{15}$ are identical or different and denote hydrogen, phenyl or straight-chain or branched alkyl having up to 3 carbon atoms, $R^8$ denotes hydrogen, carboxyl, straight-chain or branched alkoxycarbonyl having up to 3 carbon atoms or straight-chain or branched alkyl having up to 4 carbon atoms, which is optionally substituted by hydroxyl, carboxyl or by straight-chain or branched alkoxycarbonyl having in each case up to 3 carbon atoms or phenyl, $R^9$ and $R^{10}$ are identical or different and denote hydrogen, cyclopropyl, cyclopentyl, cyclohexyl or phenyl, or denote straight-chain or branched alkyl having up to 5 carbon atoms, which is optionally substituted by phenyl, cyclopropyl, cyclopentyl, cyclohexyl, hydroxyl, carboxyl, by straight-chain or branched alkoxy or alkoxycarbonyl having in each case up to 3 carbon atoms or by a group of the formula —$NR^{16}R^{17}$, wherein $R^{16}$ and $R^{17}$ are identical or different and denote hydrogen, phenyl or straight-chain or branched alkyl having up to 3 carbon atoms, or $R^9$ and $R^{10}$ together with the nitrogen atom form a heterocyclic radical of the formula

wherein

Z denotes an oxygen atom or the group —$NR^{18}$ or —CH, wherein $R^{18}$ denotes hydrogen, acetyl, tert-butoxycarbonyl or a radical of the formula —$SO_2R^{19}$, wherein $R^{19}$ denotes straight-chain or branched alkyl having up to 3 carbon atoms, benzyl or phenyl, which is optionally substituted by phenyl or tolyl, W denotes straight-chain or branched alkyl having 2 to 7 carbon atoms, which is substituted 1 to 3 times in an identical or different manner by hydroxyl, pyridyl, norbornyl or phenyl, which in its turn can be substituted by hydroxyl or benzyloxy, or is substituted by a group of the formula —$OR^{20}$ or —$NR^{21}R^{22}$, wherein $R^{20}$ denotes straight-chain or branched alkyl having up to 4 carbon atoms and $R^{21}$ and $R^{22}$ are identical or different and have the abovementioned meaning of $R^{16}$ and $R^{17}$, X denotes an oxygen or sulphur atom, Y denotes formyl or the group —$CHR^{23}R^{24}$, wherein $R^{23}$ denotes hydrogen, $R^{24}$ denotes hydroxyl or straight-chain or branched alkoxy or acyl having in each case up to 3 carbon atoms, or $R^{23}$ and $R^{24}$ are identical or different and denote straight-chain or branched alkoxy having up to 3 carbon atoms, $R^{11}$ denotes a radical of the formula

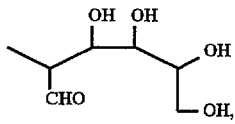

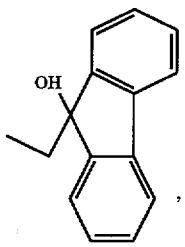

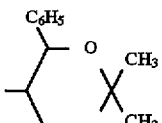

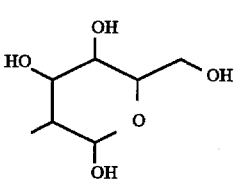

or phenyl, which is optionally substituted up to twice in an identical or different manner by fluorine, chlorine, bromine, carboxyl or straight-chain or branched alkoxycarbonyl having up to 3 carbon atoms, or denotes straight-chain or branched alkyl having up to 5 carbon atoms, which is optionally substituted up to twice in an identical or different manner by hydroxyl, carboxyl, fluorine, chlorine, bromine or by straight-chain or branched alkoxycarbonyl having up to 3 carbon atoms, and salts thereof, wherein 2-[4-(quinolin-2-yl-methoxy)-phenyl]-2-cyclopentylacetic acid [(L)-2-hydroxy-1-phenylethyl] amide 2-[4-(quinolin-2-yl-methoxy)phenyl]-2-cyclopentyl-acetic acid methyloxycarbonylmethylamide, 2-[4-(quinolin-2-yl-methoxy)phenyl]-2-cyclopentyl-acetic acid carboxymethylamide, N-methyl-2-[3-isobutyl-4-(quinolin-2-yl-methoxy) phenyl]-2-cycloheptyl-acetic acid amide, N-methyl-2-[4-(quinolin-2-yl-methoxy)phenyl]-2-cycloheptyl-acetic acid amide, N-ethyl-2-[4-(quinolin-2-yl-methoxy)phenyl]-2-cyclopentyl-acetic acid amide and N-ethyl-2-[4-(quinolin-2-yl-methoxy)phenyl]-2-cyclohexyl-acetic acid amide are excluded.

4. A compound according to claim 1 wherein such compound is (2S)-2-[4-(Quinolin-2-yl-methoxy)-phenyl]-2-cyclopentyl-acetic acid (R)-(O-acetyl)-phenylglycinolamide of the formula

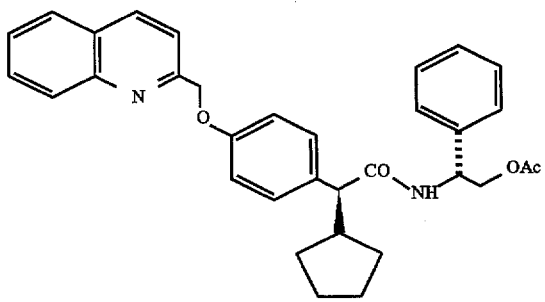

and a salt thereof.

5. A compound according to claim 1 wherein such compound is 2-{4-[Quinolin-2-yl-methoxy]phenyl}-2-cyclopentyl acetic acid [4-tert-butylphenyl]glycinol-amide of the formula

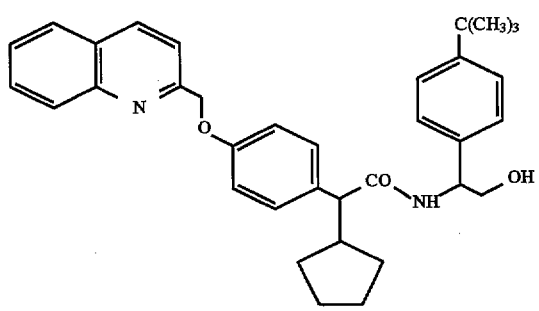

and a salt thereof.

6. A compound according to claim 1 wherein such compound is 2-[4-(Quinolin-2-yl-methoxy)phenyl]-2-cycloheptyl-acetic acid (phenylglycine ethyl ester)-amide of the formula

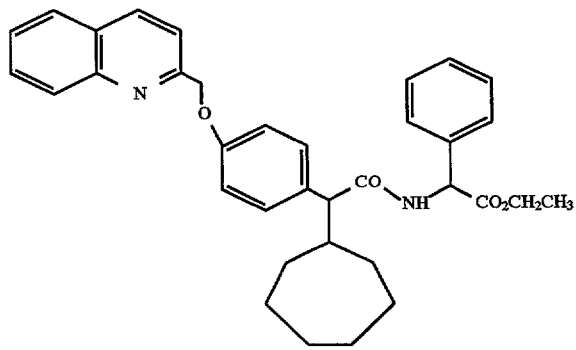

and a salt thereof.

7. A compound according to claim 1 wherein such compound is (2S)-2-[4-(Quinolin-2-yl-methoxy)-phenyl]-2-cycloheptyl-acetic acid N-(1-phenyl-vinyl)amide of the formula

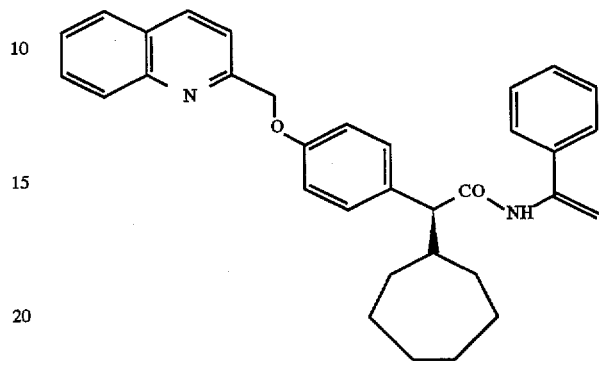

and a salt thereof.

8. A compound according to claim 1 wherein such compound is (α-Hydroxymethyl)benzyl 2-[4-quinolin-2-yl-methoxy)phenyl]-2-cyclopentyl-acetate of the formula

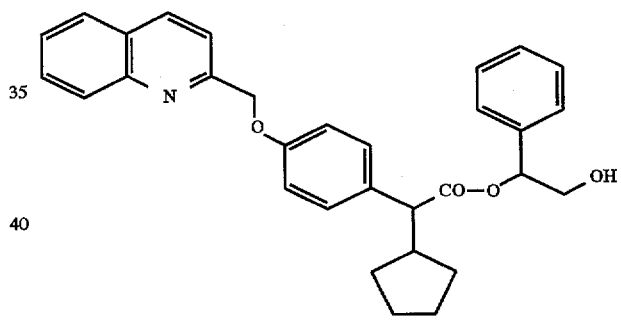

and a salt thereof.

9. A composition for the treatment of atherosclerosis comprising an amount effective therefor of a compound or salt thereof according to claim 1 and a pharmacologically acceptable diluent.

10. A method of treating atherosclerosis in a patient in need thereof which comprises a compound or a salt thereof according to claim 1.

* * * * *